(12) United States Patent
Baum et al.

(10) Patent No.: US 9,896,698 B2
(45) Date of Patent: Feb. 20, 2018

(54) MIRNA396 AND GROWTH REGULATING FACTORS FOR CYST NEMATODE TOLERANCE IN PLANTS

(71) Applicant: Iowa State University Research Foundation, Inc., Ames, IA (US)

(72) Inventors: Thomas J. Baum, Ames, IA (US); Tarek Hewezi, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 95 days.

(21) Appl. No.: 14/793,870

(22) Filed: Jul. 8, 2015

(65) Prior Publication Data

US 2016/0040183 A1 Feb. 11, 2016

Related U.S. Application Data

(63) Continuation of application No. 13/457,775, filed on Apr. 27, 2012, now abandoned.

(60) Provisional application No. 61/480,093, filed on Apr. 28, 2011.

(51) Int. Cl.
*C12N 15/82* (2006.01)

(52) U.S. Cl.
CPC ..... *C12N 15/8285* (2013.01); *C12N 15/8218* (2013.01)

(58) Field of Classification Search
None
See application file for complete search history.

(56) References Cited

U.S. PATENT DOCUMENTS

2006/0174380 A1* 8/2006 Carrington ............ C12N 15/111 800/285
2009/0012029 A1 1/2009 Hussey et al.
2010/0192237 A1 7/2010 Ren et al.
2011/0296555 A1 12/2011 Ivashuta et al.

FOREIGN PATENT DOCUMENTS

WO 2010002984 1/2010

OTHER PUBLICATIONS

Hewezi et al, 2012, Plant Phys., 159:321-335.*
Liu et al, 2009, Physiologica Plantarum, 136:223-236.*
Hewezi et al, 2008, MPMI, 21:1622-1634.*
Mazarei et al (2004, Mol. Plant Path., 5:409-423.*
Hewzi, Tarek et al., "*Arabidopsis* Small RNAs and Their Targets During Cyst Nematode Parasitism," MPMI vol. 21, No. 12, 2008, pp. 1622-1634.
Kim, Jeong Hoe et al., "The AtGRF family of putative transcription factors is involved in leaf and cotyledon growth in *Arabidopsis*," The Plant Journal (2003) 36, 94-104.
Liu Dongmei et al., "Ectopic expression of miR396 suppresses GRF target gene expression and alters leaf growth in *Arabidopsis*," Physiologia Plantarum 136: 223-236, 2009.
Rodriguez, Ramiro E. et al., "Control of cell proliferation in *Arabidopsis thaliana* by microRNA miR396," Development 137, 103-112 (2010).
Zhang, Baohong et al., "Conservation and divergence of plant microRNA genes," The Plant Journal (2006) 46, 243-259.
International Searching Authority, "The International Search Report and the Written Opinion" issued in connection to International Application No. PCT/US2012/035453 dated Nov. 30, 2012.
Hewezi et al., 2012, Plant Phys., 159:321-335.
Liu et al., 2009 Physiologica Plantarum, 136:223-236.
Mazarei et al., 2004, Mol. Plant Path., 5:409-423.
Hewezi et al., 2008, MPMI, 21:1622-1634.

* cited by examiner

Primary Examiner — Jason Deveau Rosen
(74) Attorney, Agent, or Firm — McKee, Voorhees & Sease, PLC

(57) ABSTRACT

The present invention presents methods to alter the genetic composition of crop plants susceptible to nematode infection to improve tolerance to the same. Methods and compositions for modulating key pathways involved in the syncytial event of nematode infection and for preventing the cascade of differential gene expression caused by the same as disclosed. Applicants have found that the microRNA miR396 acts as a master switch of syncytial gene expression changes in plants after infection, and further that miR396 and certain growth regulating transcription factors (GRF) are connected through feedback interaction in syncytium initiation and maintenance.

6 Claims, 12 Drawing Sheets

Figure 1:
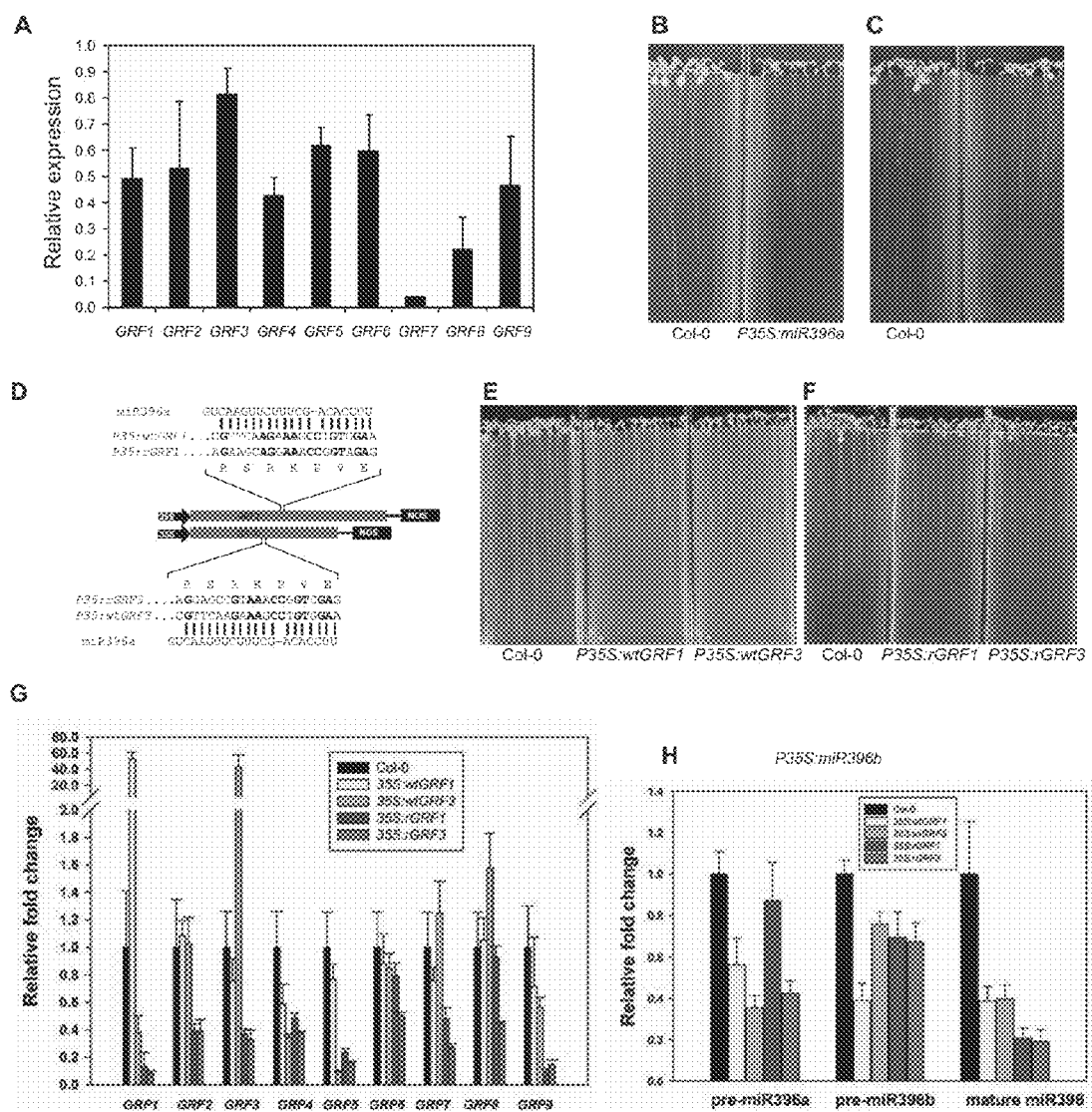

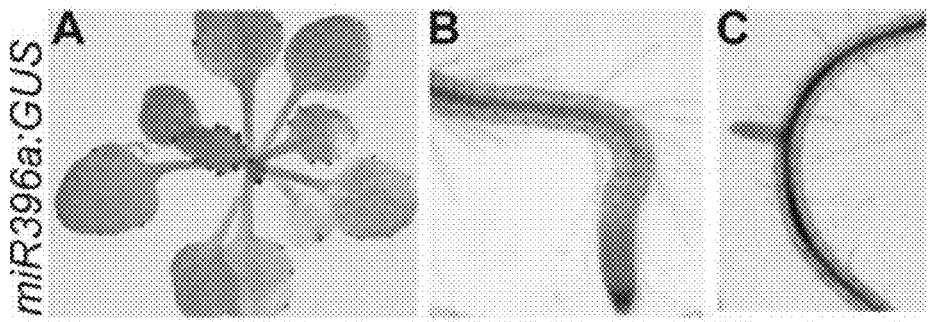
*FIG. 8A*  *FIG. 8B*  *FIG. 8C*
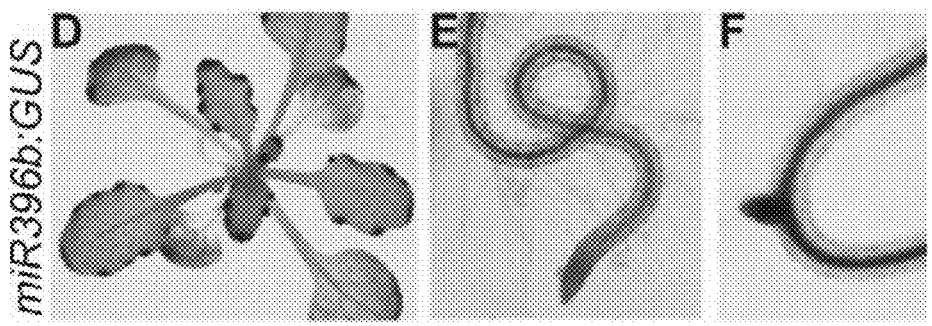
*FIG. 8D*  *FIG. 8E*  *FIG. 8F*
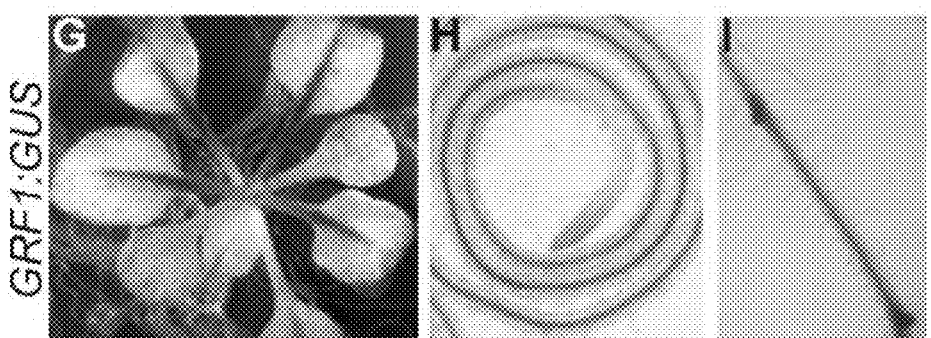
*FIG. 8G*  *FIG. 8H*  *FIG. 8I*
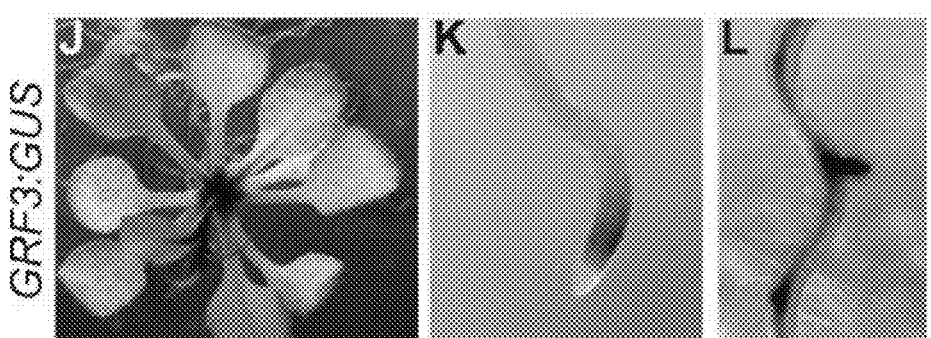
*FIG. 8J*  *FIG. 8K*  *FIG. 8L*

MIRNA396 AND GROWTH REGULATING FACTORS FOR CYST NEMATODE TOLERANCE IN PLANTS

CROSS-REFERENCE TO RELATED APPLICATIONS

This is a Continuation Application of U.S. Ser. No. 13/457,775 filed Apr. 27, 2012, which application claims priority under 35 U.S.C. § 119 to provisional application Ser. No. 61/480,093 filed Apr. 28, 2011, both are herein incorporated by reference in their entirety.

GRANT REFERENCE

This invention was made with government support under Contract No. 2008-35302-18824 awarded by USDA. The government has certain rights in the invention.

FIELD OF THE INVENTION

The invention relates generally to the field of plant molecular biology.

BACKGROUND OF THE INVENTION

Nematodes are a very large group of invertebrate animals generally referred to as roundworms, threadworms, eelworms, or nemas. Some nematodes are plant parasites and can feed on stems, buds, leaves, and in particular on roots. Cyst nematodes (principally *Heterodera* and *Globodera* spp.) are key pests of major crops. Cyst nematodes are known to infect tobacco, cereals, sugar beets, potato, rice, corn, soybeans and many other crops. *Heterodera schachtii* principally attacks sugar beets, and *Heterodera avenae* has cereals as hosts. *Heterodera zeae* feeds on corn, and *Globodera rostochiensis* and *G. pallida* feed on potatoes. The soybean cyst nematode (*Heterodera glycines*) infests every soybean-producing state in the U.S., with total soybean yield loss estimates approaching $1 billion per year.

Plant-parasitic nematodes change shape as they go through their life cycle. In its juvenile form, the animals penetrate plant roots. The number of juveniles entering the plant root soon after plant emergence can have a dramatic effect on plant growth and development. Plant damage occurs from juvenile feeding which removes cell materials and disrupts the vascular tissue by inducing the formation of novel plant cell types that are associated in a unique feeding organ, the syncytium. Due to the sedentary nature of their parasitism, cyst nematodes need to obtain all their nourishment from one location, in fact, through the contact with the initial feeding cell.

Cyst nematodes infect as second-stage juveniles (J2), which initiate the induction/formation of the syncytium. During this phase, J2s begin feeding on the growing syncytium and then develop into third-stage (J3) and fourth-stage juveniles (J4) followed by the adult stage. Syncytium formation encompasses reprogramming of differentiated plant root cells, and these redifferentiations are accompanied and mediated by massive gene expression changes, which have been documented in diverse research approaches using soybean and the soybean cyst nematode *Heterodera glycines* (Alkharouf et al., 2006; Ithal et al., 2007; Klink et al., 2009) and probably most extensively in *Arabidopsis* infected by the sugar beet cyst nematode *H. schachtii* (Szakasits et al., 2009). Regulatory networks governing gene expression patterns in nematode-infected roots and particularly in the developing syncytium are very poorly understood.

Existing methods for treating or preventing nematode disease include the use of chemicals, pesticides, and fumigants. The use of pre-plant soil fumigants is highly effective in controlling cyst nematodes and other plant-parasitic nematodes. However, the majority of the fumigant-type nematicides is no longer available and is also costly and difficult to apply properly under the prevailing conditions.

Crop rotation has also been used to control nematode disease. Rotating non-host plants can be effective in controlling nematode disease. Unfortunately, these non-host crops are often less valuable. Cover crops grown between the main crops is another alternative management strategy. Ryegrain, barley, oats, sudangrass, tall fescue, and annual ryegrass have been shown to be non- or poor hosts for some nematodes. Using cover crops, however, can be costly because the cover crops occupy space that could be used to grow more valuable crops.

Biological control organisms have also been used to try to control nematode disease in crops. Commercially available preparations of biological control organisms are limited in their use to regions that can support the growth of the control organism. Moreover, the outcome of using one organism to control another is unpredictable and subject to a variety of factors such as weather and climate.

As can be seen, a continuing need exists for the development of methods and strategies to control and inhibit plant nematode invasion.

It is an object of the present invention to develop plants, seeds, varieties and lines that have improved tolerance to nematode infection and resultant effects on plants.

It is another object of the invention to provide methods for controlling nematode infection that are environmentally friendly and do not rely on chemicals, biological control organisms, or crop rotation.

It is yet another object of the invention to provide novel plant genetic engineering strategies to ascertain more about the mechanism and plant response to nematode infection, to develop resistant varieties and to modulate expression of key components of regulatory pathways that inhibit nematode infection and its affects in the plant.

SUMMARY OF THE INVENTION

The present invention includes methods to alter the genetic composition of crop plants, particularly those that are susceptible to nematode infection, thereby improving tolerance to nematode infection and reducing the effects thereof in plants. This invention provides methods and compositions for modulating key pathways involved in the syncytial event of nematode infection and for preventing the cascade of differential gene expression caused by the same. Applicants have found that the microRNA miR396 acts as a master switch of syncytial gene expression changes in plants after infection, and further that miR396 and growth regulating transcription factors (GRF) with miRNA396 binding sites are connected through a negative feedback loop to establish an irreversible plant gene regulatory switch from syncytium initiation and maintenance.

This invention in one embodiment relates to modulation of expression of miRNA396 and GRFs with miRNA396 binding sites to engineer improved tolerance to cyst nematode infection in plants as well as the hinder the development and maintenance of the syncytium, essential for plant pathogen survival.

According to the invention, miR396 and GRF1/GRF3 are connected through a negative feedback loop from a low miR396 high GRF1/3 state during syncytium initiation, to high miR396 low GFR1/3 during maintenance. Modulated expression of this interaction alters the outcome of the plant pathogen interaction and alters plant susceptibility. In particular, overexpression of miRNA396 reduces plant susceptibility to nematode infection by more than half. Other methods of interfering with this miRNA396 and GRF interaction would also be included within the scope of this invention, whether by increasing activity of the same, through such mechanisms as overexpression, inhibition of activity, such as through inhibition of translation or transcription, or introduction of heterologous interfering or competing proteins.

Thus the invention contemplates the regulation of miRNA396 and the pathway of regulatory transcription factors associated with the same to engineer tolerance to nematode infection in plants, preferably by modulation of miRNA sequences or activity in plants.

As used herein the term "miRNA396" or "miR396" shall be interpreted to include genes such as miR396a (*Arabdopsis* ATG10606, *Glycine max* MI0001785, MIMAT0001687); miR396b (*Arabidopsis* AT5G35407, *Glycine max* MI0001786, MIMAT0001688); miR396c (*Glycine max* MI0010572, MIMAT0010079); and miR396e (*Glycine max* MI0016586, MIMAT0018345) which regulate expression of growth regulating transcription factor genes that have an miR396-binding site such as GRF 1 through 4 and 7 through 9 in *Arabidopsis*, See Jones-Rhoades and Bartel, 2004, "Computational identification of plant microRNAs and their targets, including a stress-induced miRNA" Mol. Cell 14, 787-799. Soybean GRFs include GRF8, 9, 12, 13, 15, 16, and 19, Mi396 is a highly conserved micro RNA as many are, and has been found in many other nematode susceptible plants including *Citrus unshiu, Glycine max* (soybean), *Lactuca sativa* (lettuce), *Lotus japonicus, Medicago truncatula, Nicotiana benthaminiana* (tobacco), *Oryza sativa* (rice), and *Populus euphratica*. See, Zhang et al., "Conservation and Divergence of Plant MicroRNA Genes" The Plant Journal (2006) 46 243-259. Additionally, other miRNA396 homologs may be identified thought databases such as Genbank, and the mircoRNA database, at world wide web mirbase.org.

Similarly, other growth regulatory transcription factor genes are known and easily identifiable by one of skill in the art through similar databases. Kim, J. H., Choi, D., Kende, H. (2003) "The AtGRF Family of Putative Transcription Factors is Involved in Leaf and Cotyledon Growth in *Arabidopsis*" The Plant Journal 36. These include, for example *Arabidopsis*, At2g22840 AtGRF1 transcription activator (GRF1), At2g36400 AtGRF3 transcription activator (GRF3), At3g52910 AtGRF4 expressed protein, growth-regulating factor, At3g13960 AtGRF5 transcription activator (GRF5), At2g06200 AtGRF6 expressed protein, At5g53660 AtGRF7 hypothetical protein At4g24150 AtGRF8 hypothetical protein. From soybean these include but are not limited to: GmGRF8 (Glyma10g07790); GRF9 (XM_003537618); GmGRF12 (Glyma13g16920); GmGRF13 (Glyma13g21630); GmGRF15 (XM_003547454); GmGRF16 (Glyma16g00970) and GmGRF19 (XM_003553541). All GFR transcription factors useful for the invention, will have an miRNA396 sequence (CAAGUUCUUUCGNACACCUU) (SEQ ID NO:27) binding site AAGGUGUNCGAAAGAACUUGC (SEQ ID NO:28) in common. Thus, although the invention is exemplified herein with specific *Arabidopsis* and soybean genes, the invention is not so limited and has applicability to any plant susceptible to nematode or other plant pathogen infection by interaction with miRNA396 and corresponding GRF transcription factors.

The invention provides methods for improving plant tolerance to cyst nematode infection by modulating miRNA 396 interacting pathway, such as, for example, increasing/modulating the activity of at least one miRNA396. In other embodiments, other steps along the signaling pathway could be modulated, such as the miRNA396 binding sites including GRF1, GRF 3 and other GRFs.

According to the invention, the methods for modulation include modification of a plant cell by introducing at least one polynucleotide sequence comprising a plant miRNA396 or plant GRF nucleic acid sequence, or subsequence thereof, into said plant cell, such that the polynucleotide sequence is operably linked to a promoter functional in said plant cell. In another embodiment, the method of modulating the production of miRNA396 or a GRF protein by increasing/modulating includes a miRNA396 or GRF gene which comprises, e.g., at least about 70%, at least about 75%, at least about 80%, at least about 85%, at least about 90%, at least about 95%, at least about 99%, at least about 99.5% or more sequence identity to miR396a (*Arabidopsis* AT2G10606 (SEQ ID NO:1), *Glycine max* MI0001785 (SEQ ID NO:12), or MIMAT0001687 (SEQ ID NO:13); miR396b (*Arabidopsis* AT5G35407 (SEQ ID NO:2), *Glycine max* MI0001786 (SEQ ID NO:14), MIMAT0001688) (SEQ ID NO:15); or miR396c (*Glycine max* MI0010572 (SEQ ID NO:16), MIMAT0010079 (SEQ ID NO:17); or miR396e (*Glycine max* MI0016586 (SEQ ID NO:18), MIMAT0018345 (SEQ ID NO:10) or to corresponding GRFs including GRF1 (At2g22840) (SEQ ID NO:3), GRF2 (At4g37740) (SEQ ID NO:4), GRF3 (At2g36400) (SEQ ID NO:5), GRF4 (At3g52910) (SEQ ID NO:6), GRF7 (At5g53660) (SEQ ID NO:9), GRF8 (At4g24150) (SEQ ID NO:10), GRF9 (At2g45480) (SEQ ID NO:11), GmGRF8 (Glyma10g07790) (SEQ ID NO:20); GRF9 (XM_003537618) (SEQ ID NO:21); GmGRF12 (Glyma13g16920) (SEQ ID NO:22); GmGRF13 (Glyma13g21630) (SEQ ID NO:23); GmGRF15 (XM_003547454) (SEQ ID NO:24); GmGRF16 (Glyma16g00970) (SEQ ID NO:25) and GmGRF19 (XM_003553541) (SEQ ID NO:26).

Many plant miRNA396s and GRFs are known to those of skill in the art such as those from rice, *Arabidopsis* and soybean and are readily available through sources such as GENBANK and the like.

In another embodiment, the invention relates to methods for improving plant tolerance to cyst nematode infection by providing an isolated or recombinant modified plant cell comprising at least one modification that increases, decreases or otherwise modulates miRNA396 or GRF activity. In certain embodiments, a plant cell resulting from the methods of the invention is from a dicot or monocot. In another aspect, the plant cell is in a plant comprising a sterility phenotype, e.g., a male sterility phenotype.

The methods of the invention are practiced with an isolated or recombinant polynucleotide comprising a member selected from the group consisting of: (a) a polynucleotide, or a complement thereof, comprising, e.g., at least about 70%, at least about 75%, at least about 80%, at least about 85%, at least about 90%, at least about 95%, at least about 99%, about 99.5% or more sequence identity to an miRNA396 or GRF transcription factor or a subsequence thereof, or a conservative variation thereof; (b) a polynucleotide, or a complement thereof, encoding a polypeptide sequence of a (c) a polynucleotide, or a complement thereof, that hybridizes under stringent conditions over substantially the entire length of a polynucleotide subsequence comprising at least 100 contiguous nucleotides of SEQ a, or that hybridizes to a polynucleotide sequence of (a) or (b); and, (d) a polynucleotide that is at least about 85% identical to a polynucleotide sequence of (a), (b) or (c).

Such polynucleotides for practice of the methods of the invention can comprise or be contained within an expression cassette or a vector (e.g., a viral vector). The vector or expression cassette can comprise a promoter (e.g., a constitutive, tissue-specific, or inducible promoter) operably linked to the polynucleotide. In a preferred embodiment, the promoter is a root specific promoter.

Detection of expression products is performed either qualitatively (by detecting presence or absence of one or more product of interest) or quantitatively (by monitoring the level of expression of one or more product of interest). Aspects of the invention optionally include monitoring an expression level of a nucleic acid, polypeptide or chemical as noted herein for detection of the same in a plant or in a population of plants.

In yet another embodiment, the present invention is directed to a transgenic plant or plant cells with improved performance under nematode infecting conditions, containing the nucleic acids described herein. Preferred plants containing the polynucleotides of the present invention include but are not limited to soybean, sunflower, maize, sorghum, canola, wheat, alfalfa, cotton, oat, rice, barley, tomato, cacao and millet. In another embodiment, the transgenic plant is a soybean plant or plant cells. Plants produced according to the invention can have at least one of the following phenotypes in nematode infecting conditions as compared to a non-modified control plant, including but not limited to: increased root mass, increased plant survival, increased root length, increased leaf size, increased ear size, increased seed size, absence of syncytia, smaller or decreased syncytia, or increased plant size when compared to a non-modified plant under conditions of nematode infection.

In yet another embodiment, levels of miRNA396 or GRF proteins or mutant polynucleotide or polypeptide (where appropriate) sequences may be used as markers or selection traits to identify and select nematode tolerant plants even in the absence of transformation for breeding of tolerant lines, plants seeds, varieties and the like. Marker assisted selection protocols are thus included herein.

DETAILED DESCRIPTION OF THE FIGURES

FIG. 1: Characterization of transgenic plants overexpressing miR396 or the target genes GRF1 and GRF3. (A) Overexpression of miR396 reduces GRF gene expression. The mRNA expression level of GRF1-9 was measured by quantitative real-time RT-PCR in the root tissues of 10 d-old wild-type (Col-0) and transgenic plants overexpressing miR396b (line 16-4). The expression levels were normalized using Actin8 as an internal control. The relative fold-change values represent changes of mRNA levels in the transgenic plants relative to the wild-type control. Data are averages of three biologically independent experiments±SE. (B) and (C) Transgenic plants overexpressing miR396a (line 22-5) (B) or miR396b (line 15-1) (C) develop shorter roots than the wild-type (Col-0). Homozygous T3 plants were planted on modified Knop's medium along with the wild type (Col-0), and root lengths were measured 10 days after planting. Root length values are averages of at least 50 plants. Differences between miR396 overexpression lines and the wild type were statistically significant as determined by unadjusted paired t tests (P<0.01). (D) Schematic representation of wild-type and miR396-resistant versions of GRF1 and GRF3 transcripts. Nucleotide pairing of miR396 with the corresponding wild-type binding sites of GRF1 (wtGRF1) and GRF3 (wtGRF3) show 19 nucleotide matches, whereas in the miR396-resistant version of GRF1 (rGRF1) and GRF3 (rGRF3) the miR396 binding site contains 10 mismatches. Conserved nucleotides between wild-type and modified miR396 binding sites are in bold. (E) and (F): Transgenic plants overexpressing wtGRF1 or wtGRF3 (E) and rGRF1 or rGRF3 (F) develop shorter roots than the wild type (Col-0). Homozygous T3 plants were planted on modified Knop's medium along with the wild type, and root lengths were measured as indicated above. Differences between overexpression lines and the wild type were statistically significant as determined by unadjusted paired t tests (P<0.01). (G) Overexpression of GRF1 or GRF3 negatively regulates GRF gene expression. The mRNA expression levels of GRF1 through 9 were quantified in the root tissues of the transgenic plants overexpressing the wild-type forms of GRF1 and GRF3 (35S:wtGRF1 and 35S:wtGRF3) or the miR396-resistant forms (35S:rGRF1 and 35S:rGRF3) using qPCR. The expression levels were normalized using Actin8 as an internal control. The relative fold-change values represent changes of GRF expression levels in the transgenic plants relative to the wild-type control. Data are averages of three biologically independent experiments±SE. Note that the expression levels of GRF1 and GRF3 in the 35S:rGRF1 and 35S:rGRF3 plants include the endogenous transcripts. (H) Overexpression of GRF1 or GRF3 negatively regulates miR396 expression. The levels of pre-miR396a, pre-miR396b and mature miR396 were quantified in root tissues of the transgenic plants described in (G) using qPCR. The expression levels were normalized using U6 snRNA as an internal control. The relative fold-change values represent changes of miRNA abundance in the transgenic plant relative to the wild-type control. Data are averages of three biologically independent experiments±SE. The expression levels of the transgenes are provided in Figure S3.

Figure 2:
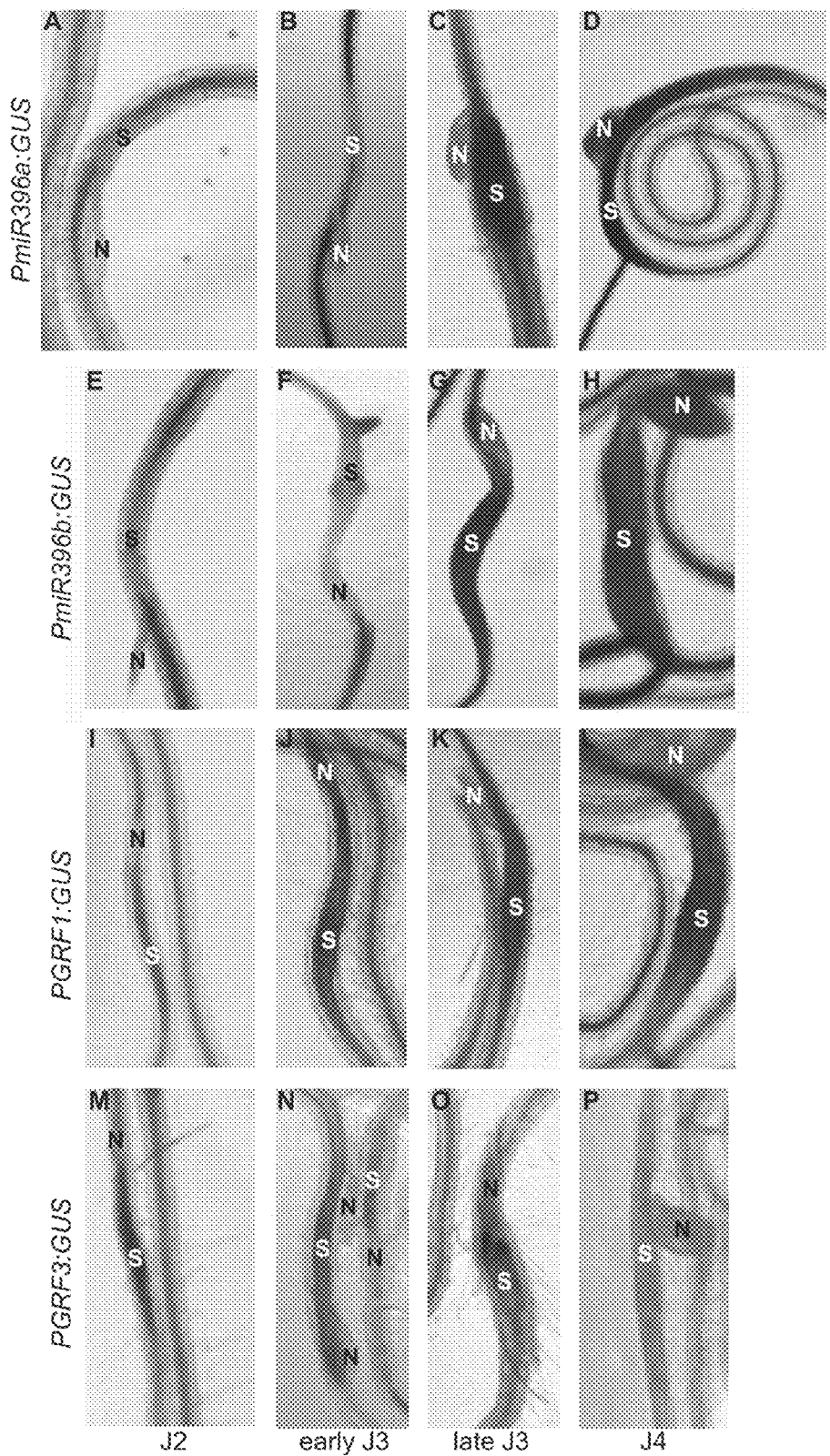

FIG. 2: Promoter activity of miR396a, miR396b and the target genes GRF1 and GRF3 during *Heterodera schachtii* infection. Time course experiments comparing the expression of miR396a:GUS (A-D), miR396b:GUS (E-H), GRF1:GUS (I-L), and GRF3:GUS (M-P) transgenic plants at the second-stage (J2), early and late third-stage (J3), and fourth-stage juvenile (J4) time points. N indicates nematode and S indicates syncytium. See also Figure S2.

Figure 3:
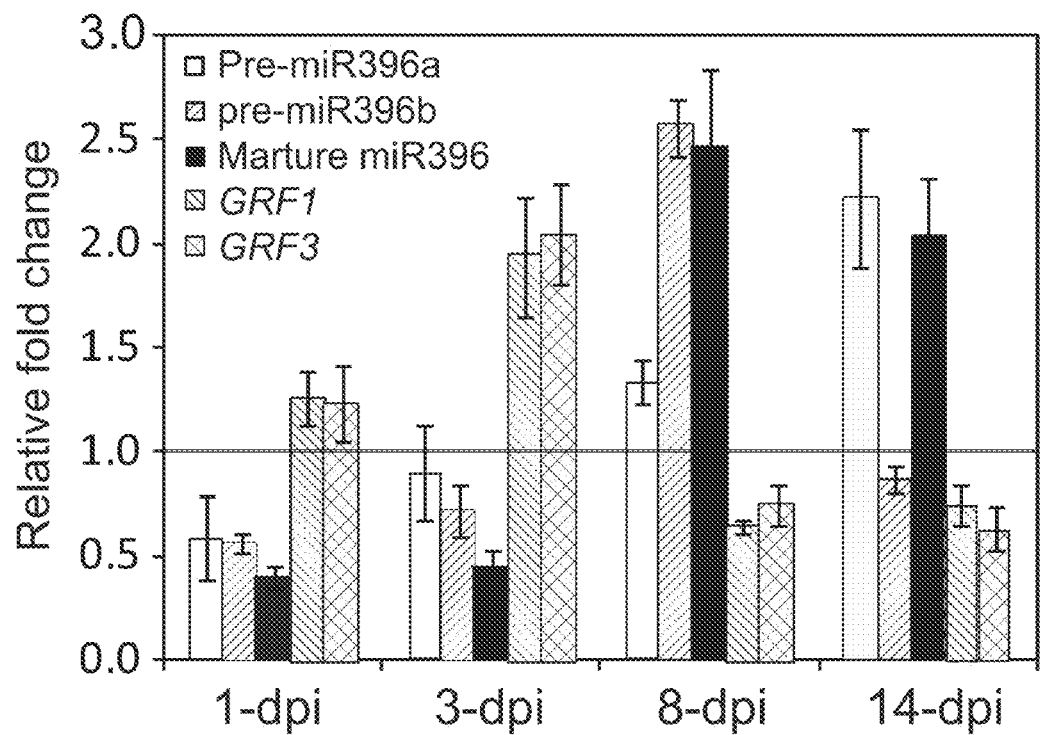

FIG. 3: Post-transcriptional regulation of GRF1 and GRF3 by miR396 in response to *H. schachtii* infection. The expression level of pre-miR396a, pre-miR396b, mature miR396, GRF1 and GRF3 was measured by qPCR in wild-type (Col-0) root tissues. Infected and noninfected tissues were collected at 1, 3, 8, and 14 days after inoculation (dpi). Down regulation of miR396 at 1 and 3 dpi was associated with up regulation of both GRF1 and GRF3. In contrast, up regulation of miR396 at 8 and 14 dpi activated the cleavage of GRF1 and GRF3 resulting in low transcript accumulation of GRF1 and GRF3. U6 snRNA was used as an internal control to normalize the expression levels of miR396, whereas Actin8 was used to normalize the expression levels of GRF1 and 3. The relative fold-change values represent changes of the expression levels in infected tissues relative to noninfected controls. Data are averages of three biologically independent experiments±SE.

Figure 4:
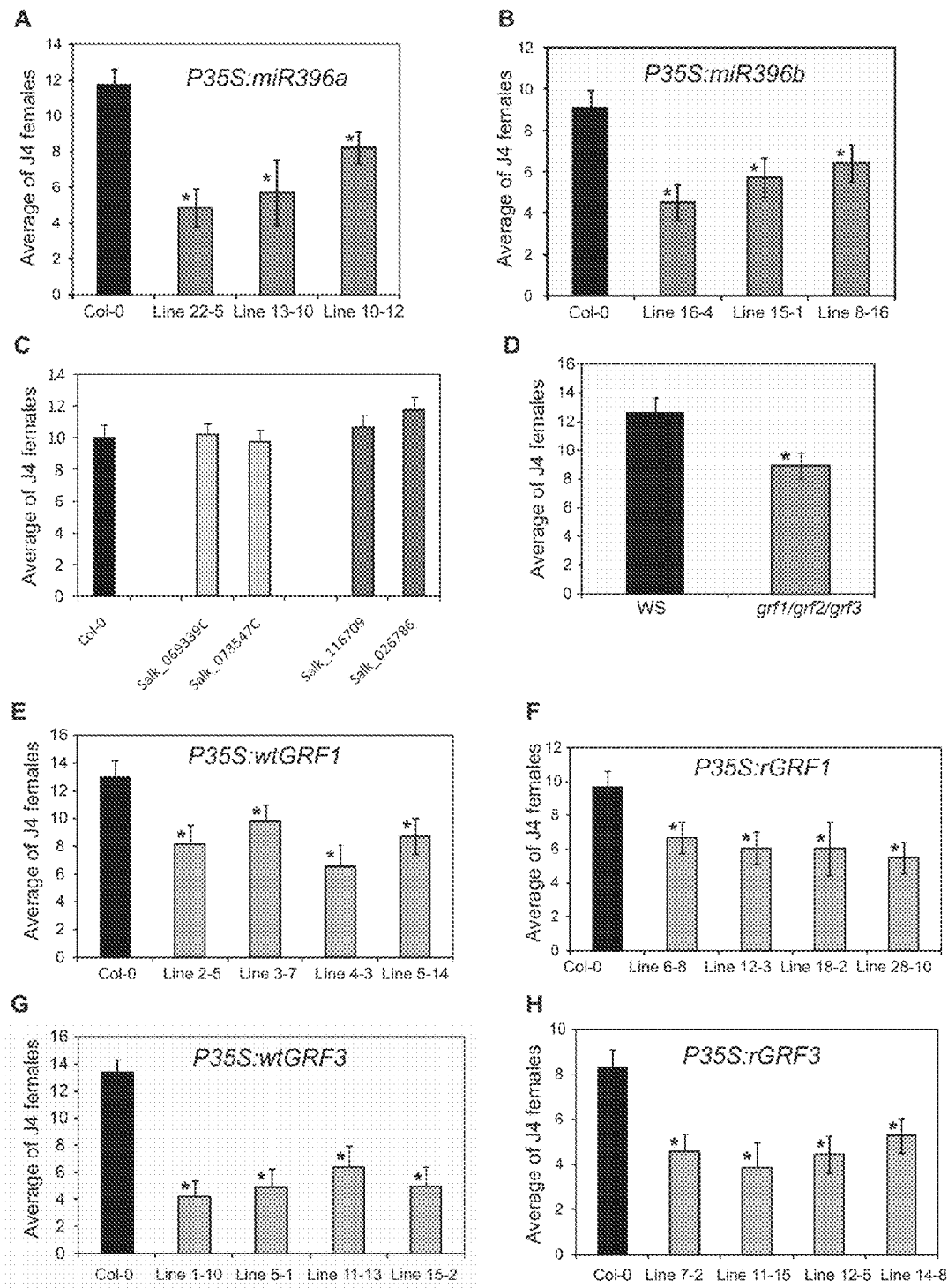

FIG. 4: Nematode susceptibility assays of miR396 overexpression lines and GRF mutants (A) and (B) Nematode susceptibility assays of miR396 overexpression lines. Transgenic plants overexpressing miR396a (A) or miR396b (B) exhibited reduced susceptibility to *H. schachtii*. Homozygous T3 lines overexpressing miR396a (lines 22-5, 13-10, and 10-12) or miR396b (lines 16-4, 15-1 and 8-16) were planted on modified Knop's medium, and 10-d-old seedlings were inoculated with ~200 surface-sterilized J2 *H. schachtii* nematodes. Three weeks after inoculation, the number of J4 female nematodes per root system was determined Data are presented as the mean±SE. Mean values significantly different from the wild type (Col-0) were determined by unadjusted paired t tests (P<0.05) and indicated by an asterisk. Identical results were obtained from at least two independent experiments. (C) Nematode susceptibility is not significantly altered in grf1 or grf3 single mutant. The mutant alleles of grf1 (Salk069339C and Salk0785 47C) and gfr3 (salk116709 and salk026786) along with wild-type Col-0 plants were planted on modified Knop's medium and assayed for nematode susceptibility. No statistically significant differences between these mutant lines and wild type were observed. Data are presented as means±SE. Similar results were obtained from at least three independent experiments. (D) The grf1/grf2/grf3 triple mutant exhibited reduced susceptibility to *H. schachtii*. Seeds of the grf1/grf2/grf3 triple mutant and wild type (WS) were planted on modified Knop's medium and assayed for nematode susceptibility. Data are presented as means±SE and the statistically significant difference between the grf1/grf2/grf3 mutant and the wild type (WS) is denoted by asterisk as determined by unadjusted paired t tests (P<0.05). Identical results were obtained from two independent experiments. (E-H). Transgenic plants overexpressing wtGRF1 (E), rGRF1 (F), wtGRF3 (G) or rGRF3 (H) revealed reduced susceptibility to *H. schachtii*. Four independent homozygous T3 lines for each construct were assayed for nematode susceptibility. All lines showed significantly reduced susceptibility compared with wild-type plants. Data are presented as the mean±SE. Mean values significantly different from the wild-type (Col-0) were determined by unadjusted paired t tests (P<0.05) and indicated by an asterisk. Identical results were obtained from at least two independent experiments.

Figure 5:
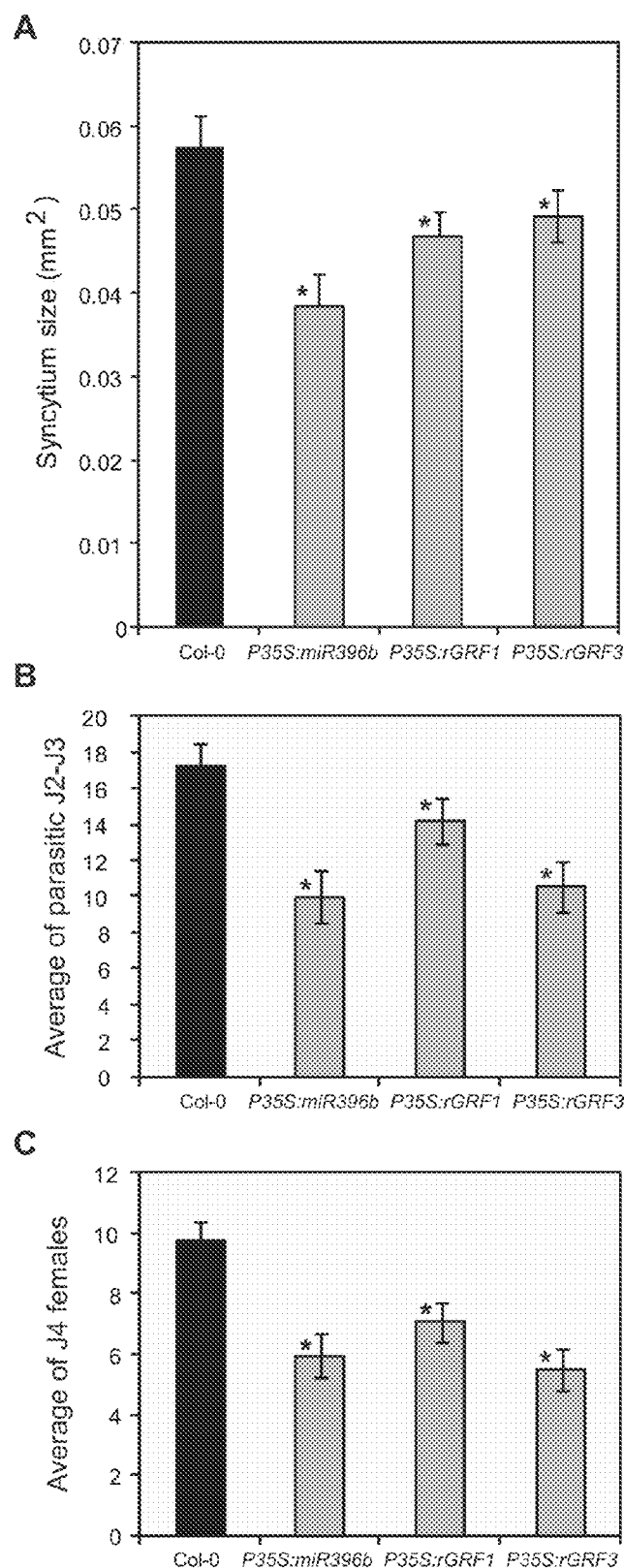

FIG. 5: Overexpression of miR396, GRF1 or GRF3 negatively impacts syncytium size and nematode development. (A) Transgenic plants overexpressing miR396, rGRF1 or rGRF3 developed smaller syncytia than the wild type. Homozygous T3 lines overexpressing miR396b (line 16-4), rGRF1 (lines 12-3) or rGRF3 (line 12-5) as well as wild-type (Col-0) were planted on modified Knop's medium, and 10-d-old seedlings were inoculated with ~200 surface-sterilized J2 *H. schachtii* nematodes. Two weeks post-inoculation, at least 20 single-nematode syncytia were randomly selected and measured. Data are presented as means±SE. The asterisk indicates a statistically significance difference from wild-type plants at P<0.05. (B) and (C) Overexpression of miR396, rGRF1 or rGRF3 negatively impacts nematode development. Seeds of the above-indicated lines along with wild-type (Col-0) were planted and inoculated as described in (A). After inoculation, the number of parasitic J2/J3 (B) and J4 females (C) was counted in the same plants. Data are presented as means±SE. The asterisk indicates a statistically significance difference from wild-type plants at P<0.05.

Figure 6:
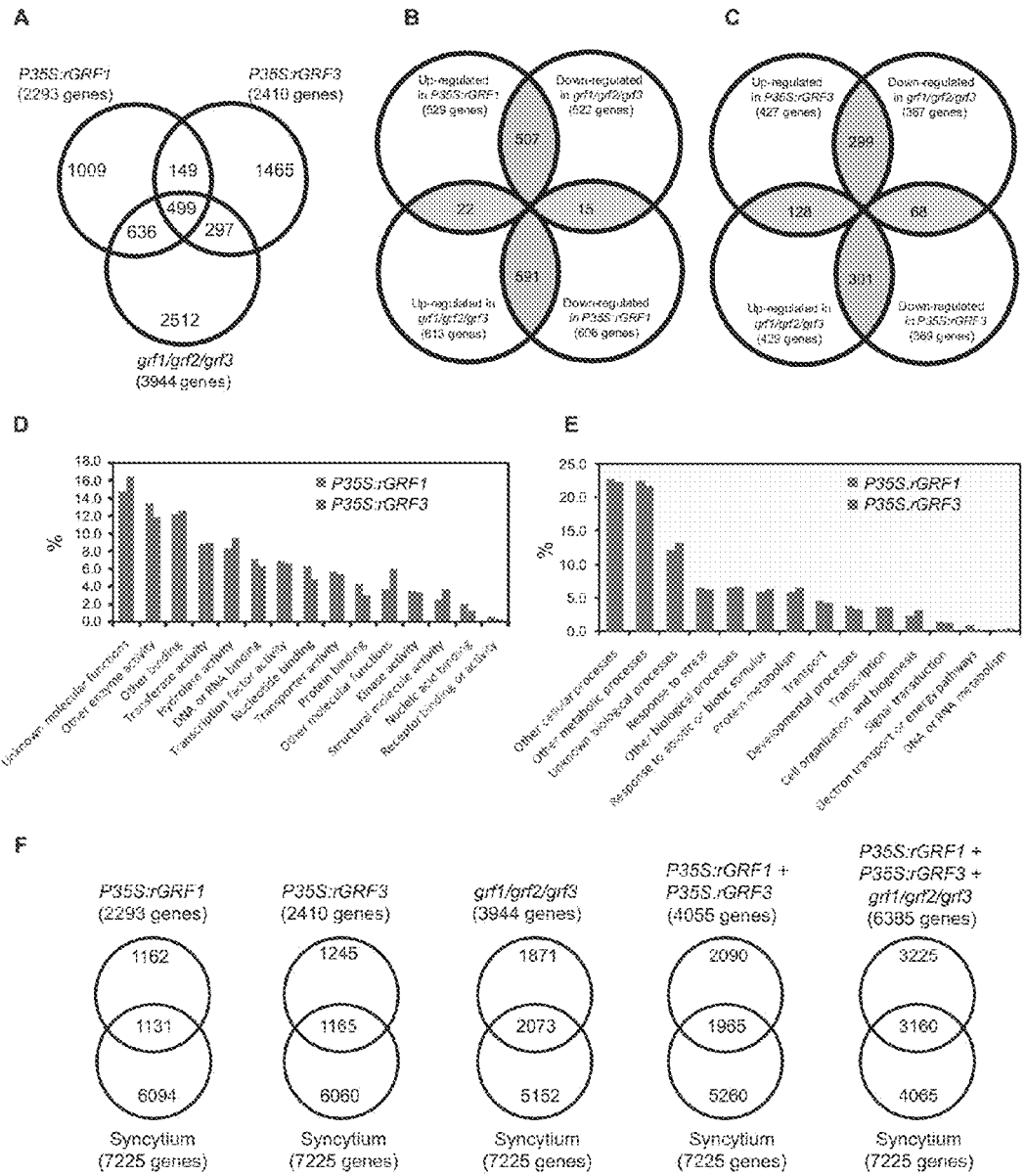

FIG. 6: Functional classification of the differentially expressed genes identified in 35S:rGRF1, 35S:rGRF1 and grf1/grf2/grf3 mutants. (A) Venn diagram showing overlaps between differentially expressed genes in 35S:rGRF1, 35S:rGRF3 and grf1/grf2/grf3 mutants. The total number of differentially expressed genes in each set is shown in parentheses. Genes are listed in Table S1A-C. (B) and (C) Venn diagram comparing the overlapping differentially expressed genes between 35S:rGRF1 and grf1/grf2/grf3 (B) or 35S:rGRF1 and grf1/grf2/grf3 (C). Numbers in the areas highlighted in red indicate differentially expressed genes that exhibit opposite expression whereas overlapping areas highlighted in blue indicate the number of the differentially expressed genes that exhibited similar expression. (Genes are listed in Table S1D and E). (D) and (E) Gene ontology categorization of the molecular functions (D) or the biological processes (E) of the candidate target genes of GRF1 or GRF3. (Genes used for this categorization are listed in Table S1D and E). (F) Venn diagram showing overlaps between differentially expressed genes in the syncytium and those identified in 35S:rGRF1, 35S:rGRF1 and grf1/grf2/grf3 mutants. The total number of differentially expressed genes in each set is shown in parentheses.

Figure 7:
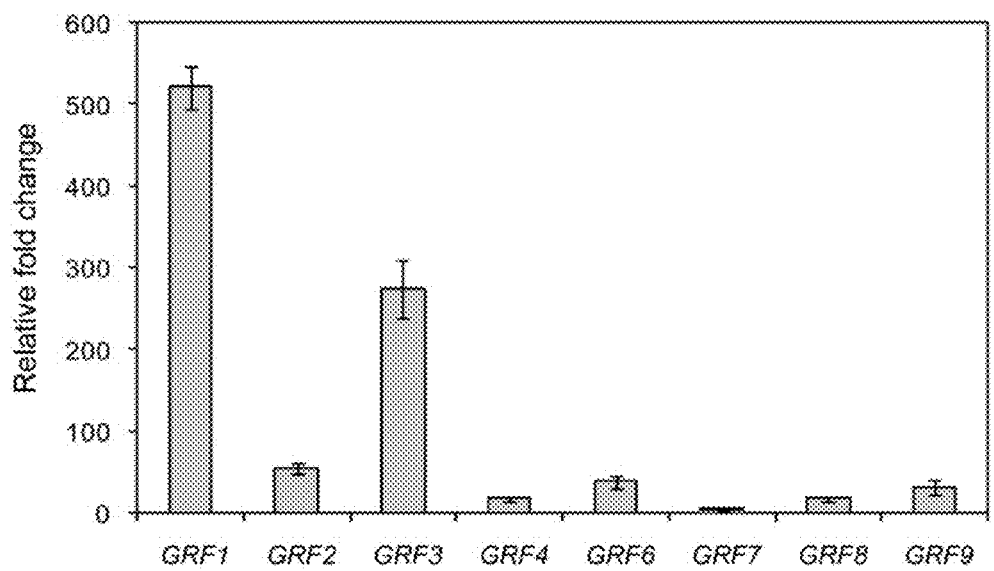

FIG. 7: Expression profiles of GRF gene family members in *Arabidopsis* roots.

FIG. 8 (A-L): Spatial expression patterns of miR396a and miR396b and the target genes GRF1 and GRF3.

FIG. 9 (A-F): Quantification of transgene expression levels in the transgenic *Arabidopsis* lines described in this study using qPCR.

Figure 10A:
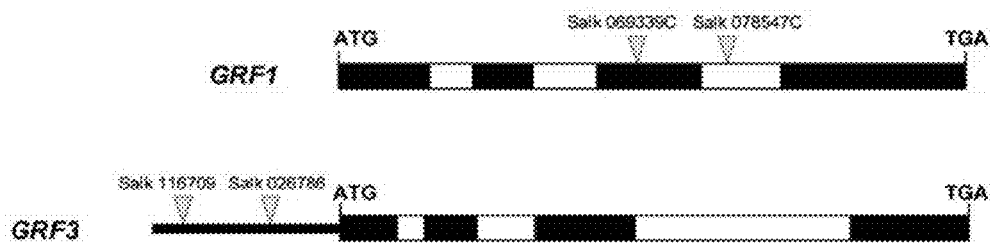
Figure 10B:
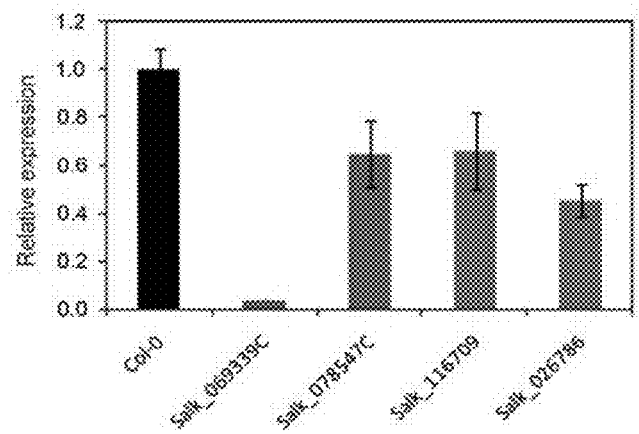
Figure 10C:
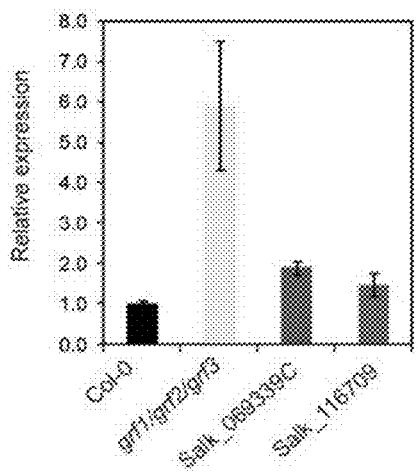

FIG. 10 (A-C): Characterization of *Arabidopsis* grf1 and grf3 mutants.

Figures 11A, 11B, 11C, 11D:
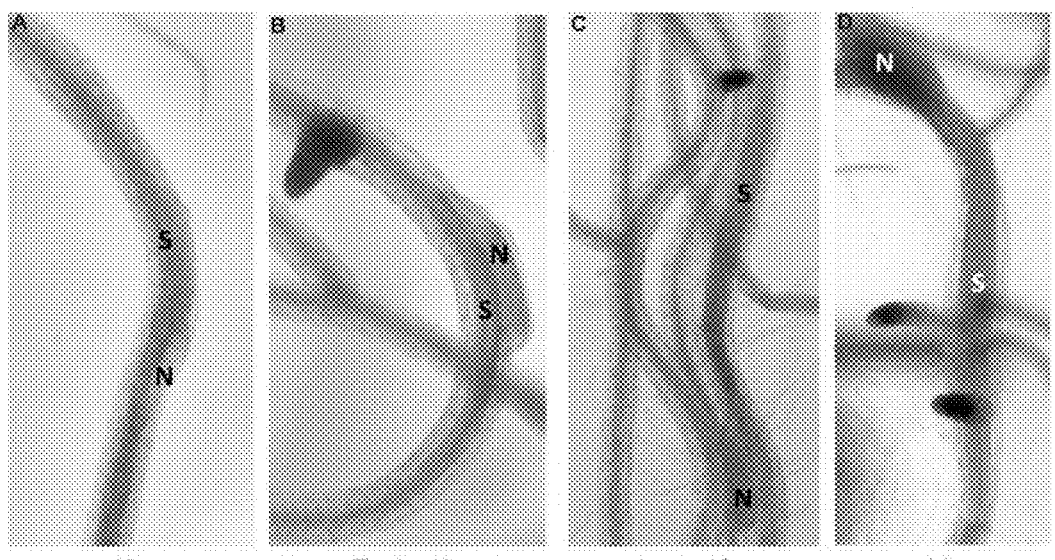

FIG. 11 (A-D): GRF2 promoter activity during *Heterodera schachtii* infection.

Figure 12:
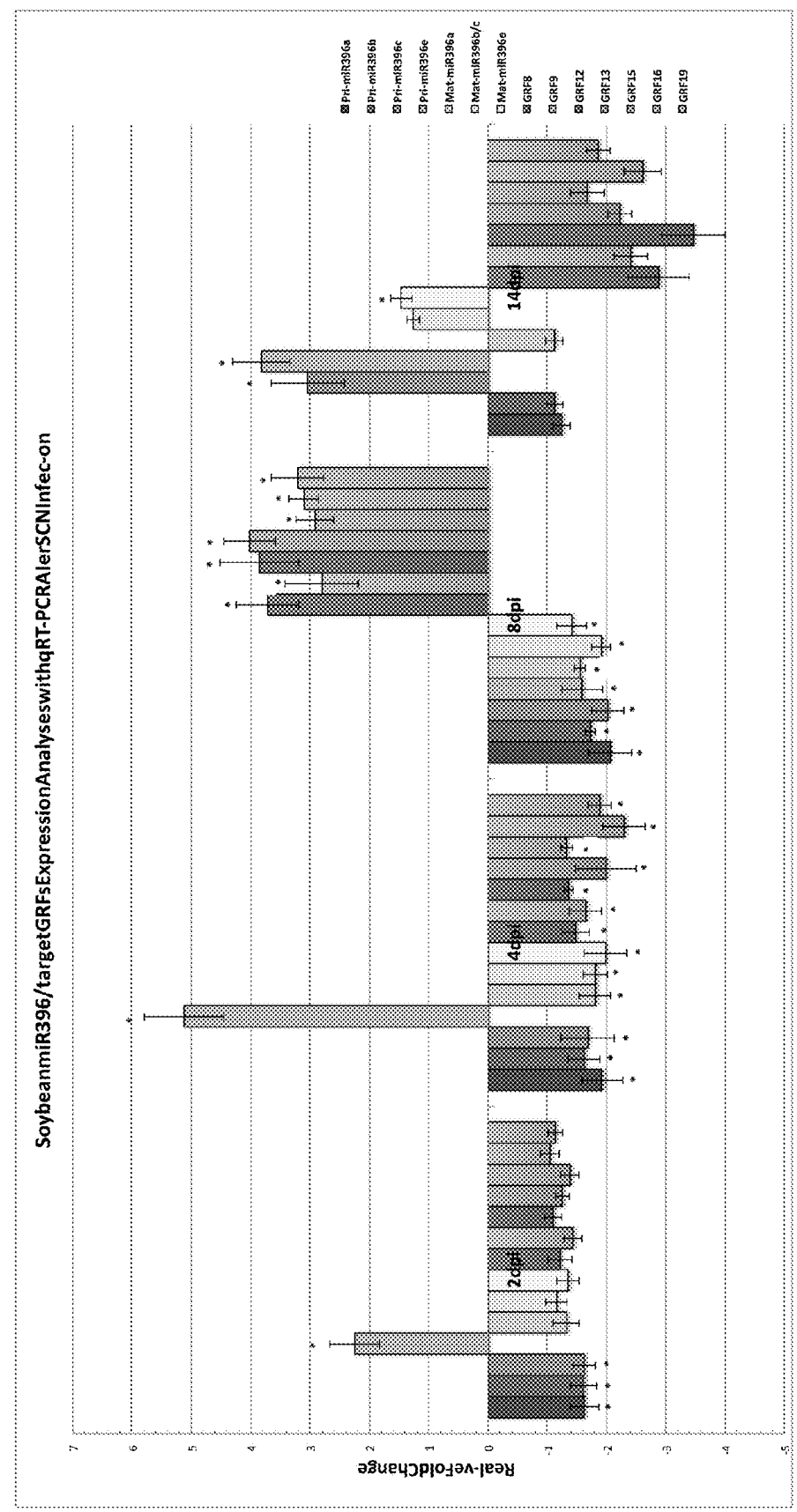

FIG. 12: Soybean miR396/target GRFs Expression Analyses with qRT-PCR after SCN Infection.

DETAILED DESCRIPTION OF THE INVENTION

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) Botany: Plant Biology and Its Relation to Human Affairs, John Wiley; Cell Culture and Somatic Cell Genetics of Plants, vol. 1, Vasil, ed. (1984); Stanier, et al., (1986) The Microbial World, 5$^{th}$ ed., Prentice-Hall; Dhringra and Sinclair, (1985) Basic Plant Pathology Methods, CRC Press; Maniatis, et al., (1982) Molecular Cloning: A Laboratory Manual; DNA Cloning, vols. I and II, Glover, ed. (1985); Oligonucleotide Synthesis, Gait, ed. (1984); Nucleic Acid Hybridization, Hames and Higgins, eds. (1984); and the series Methods in Enzymology, Colowick and Kaplan, eds, Academic Press, Inc., San Diego, Calif.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole. In describing the present invention, the following terms will be employed, and are intended to be defined as indicated below.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) J. Gen. Microbiol. 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, Proteins, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) Proc. Natl. Acad. Sci. USA 82:2306-9), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "control plant" is a plant without recombinant DNA disclosed herein. A control plant is used to measure and compare trait improvement in a transgenic plant with such recombinant DNA. A suitable control plant may be a non-transgenic plant of the parental line used to generate a transgenic plant herein. Alternatively, a control plant may be a transgenic plant that comprises an empty vector or marker gene, but does not contain the recombinant DNA that produces the trait improvement. A control plant may also be a negative segregant progeny of hemizygous transgenic plant.

As used herein, "gene" refers to chromosomal DNA, plasmid DNA, cDNA, synthetic DNA, or other DNA that encodes a peptide, polypeptide, protein, or RNA molecule, and regions flanking the coding sequences involved in the regulation of expression.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, lawn grass, barley, millet, and tomato. A particularly preferred monocotyledonous host cell is a soybean host cell.

The term "hybridization complex" includes reference to a duplex nucleic acid structure formed by two single-stranded nucleic acid sequences selectively hybridized with each other.

As used herein, "improved trait" refers to a trait with a detectable improvement in a transgenic plant relative to a control plant or a reference. In some cases, the trait improvement can be measured quantitatively. For example, the trait improvement can entail at least a 2% desirable difference in an observed trait, at least a 5% desirable difference, at least about a 10% desirable difference, at least about a 20% desirable difference, at least about a 30% desirable difference, at least about a 50% desirable difference, at least about a 70% desirable difference, or at least about a 100% difference, or an even greater desirable difference. In other cases, the trait improvement is only measured qualitatively. It is known that there can be a natural variation in a trait. Therefore, the trait improvement observed entails a change of the normal distribution of the trait in the transgenic plant compared with the trait distribution observed in a control plant or a reference, which is evaluated by statistical methods provided herein. Trait improvement includes, but not limited to, yield increase, including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" or "isolated nucleic acid" or "isolated protein" refer to material, such as a nucleic acid or a protein, which is substantially or essentially free from components which normally accompany or interact with it as found in its naturally occurring environment. The isolated material optionally comprises material not found with the material in its natural environment. Nucleic acids which are "isolated", as defined herein, are also referred to as "heterologous" nucleic acids.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) Guide To Molecular Cloning Techniques, from the series Methods in Enzymology, vol. 152, Academic Press, Inc., San Diego, Calif.; Sambrook, et al., (1989) Molecular Cloning: A Laboratory Manual, $2^{nd}$ ed., vols. 1-3; and Current Protocols in Molecular Biology, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, cells in or from seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*. A particularly preferred plant is *Zea mays*.

As used herein, "yield" may include reference to bushels per acre of a grain crop at harvest, as adjusted for grain moisture (15% typically for maize, for example), and/or the volume of biomass generated (for forage crops such as alfalfa, and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells. The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples are promoters that preferentially initiate transcription in certain tissues, such as leaves, roots, seeds, fibres, xylem vessels, tracheids, or sclerenchyma. Such promoters are referred to as "tissue-preferred." A "cell type" specific promoter primarily drives expression in certain cell types in one or more organs, for example, vascular cells in roots or leaves. An "inducible" or "regulatable" promoter is a promoter which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

As used herein "recombinant" includes reference to a cell or vector that has been modified by the introduction of a heterologous nucleic acid, or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention; or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) Anal. Biochem., 138:267-84: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, part I, chapter 2, "Overview of principles of hybridization and the strategy of nucleic acid probe assays," Elsevier, New York (1993); and Current Protocols in Molecular Biology, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

As used herein, "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g., by measuring uptake of carbon dioxide, or by the observation of the expression level of a gene or genes, e.g., by employing Northern analysis, RT-PCR, microarray gene expression assays, or reporter gene expression systems, or by agricultural observations such as stress tolerance, yield, or pathogen tolerance.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "transgenic seed" refers to a plant seed whose genome has been altered by the incorporation of recombinant DNA, e.g., by transformation as described herein. The term "transgenic plant" is used to refer to the plant produced from an original transformation event, or progeny from later generations or crosses of a plant to a transformed plant, so long as the progeny contains the recombinant DNA in its genome.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may conduct optimal alignment of sequences for comparison; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Version 8 (available from Genetics Computer Group (GCG® programs (Accelrys, Inc., San Diego, Calif.).). The CLUSTAL program is well described by Higgins and Sharp, (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65, and Pearson, et al., (1994) Meth. Mol. Biol. 24:307-31. The preferred program to use for optimal global alignment of multiple sequences is PileUp (Feng and Doolittle, (1987) J. Mol. Evol., 25:351-60 which is similar to the method described by Higgins and Sharp, (1989) CABIOS 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of skill will recognize that these m values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides which are "substantially similar" share sequences as noted above, except that residue positions which are not identical may differ by conservative amino acid changes.

Many agronomic traits can affect "yield", including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other traits that can affect yield include, efficiency of germination (including germination in stressed conditions), growth rate (including growth rate in stressed conditions), ear number, seed number per ear, seed size, composition of seed (starch, oil, protein) and characteristics of seed fill. Also of interest is the generation of transgenic plants that demonstrate desirable phenotypic properties that may or may not confer an increase in overall plant yield. Such properties include enhanced plant morphology, plant physiology or improved components of the mature seed harvested from the transgenic plant.

As used herein, "increased yield" of a transgenic plant of the present invention may be evidenced and measured in a number of ways, including test weight, seed number per plant, seed weight, seed number per unit area (i.e., seeds, or weight of seeds, per acre), bushels per acre, tons per acre, kilo per hectare. For example, maize yield may be measured as production of shelled corn kernels per unit of production area, e.g., in bushels per acre or metric tons per hectare, often reported on a moisture adjusted basis, e.g., at 15.5% moisture. Increased yield may result from improved utilization of key biochemical compounds, such as nitrogen, phosphorous and carbohydrate, or from improved tolerance to environmental stresses, such as cold, heat, drought, salt, and attack by pests or pathogens. Trait-improving recombinant DNA may also be used to provide transgenic plants having improved growth and development, and ultimately increased yield, as the result of modified expression of plant growth regulators or modification of cell cycle or photosynthesis pathways.

Nucleic Acids

The present invention provides, inter alia, for the use of isolated nucleic acids of RNA, DNA, homologs, paralogs and orthologs and/or chimeras thereof, comprising a plant miRNA396 and plant GRF encoding polynucleotide. This includes naturally occurring as well as synthetic variants and homologs of the sequences.

Sequences homologous, i.e., that share significant sequence identity or similarity, to those provided herein derived from maize, *Arabidopsis thaliana*, rice or from other plants of choice, are also an aspect of the invention. Homologous sequences can be derived from any plant including monocots and dicots and in particular agriculturally important plant species, including but not limited to, crops such as soybean, wheat, corn (maize), potato, cotton, rice, rape, oilseed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such pine, poplar and eucalyptus, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), related to corn (maize).

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may result in two copies of a particular gene, giving rise to two or more genes with similar sequence and often similar function known as paralogs. A paralog is therefore a similar gene formed by duplication within the same species. Paralogs typically cluster together or in the same Glade (a group of similar genes) when a gene family phylogeny is analyzed using programs such as CLUSTAL (Thompson et al. (1994) Nucleic Acids Res. 22: 4673-4680; Higgins et al. (1996) Methods Enzymol. 266: 383-402). Groups of similar genes can also be identified with pair-wise BLAST analysis (Feng and Doolittle (1987) J. Mol. Evol. 25: 351-360).

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) Nucleic Acids Res. 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence). Variant Nucleotide Sequences in the non-coding regions The plant miRNA396 or GRF1/3 nucleotide sequences maybe used to generate variant nucleotide sequences having the nucleotide sequence of the 5'-untranslated region, 3'-untranslated region, or promoter region that is approximately 70%, 75%, 80%, 85%, 90% and 95% identical to the original nucleotide sequence. These variants are then associated with natural variation in the germplasm for component traits related to nematode infection. The associated variants are used as marker haplotypes to select for the desirable traits.
Variant Amino Acid Sequences of Polypeptides Variant amino acid sequences of the plant GRF polypeptides are generated. For one example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined herein is followed. Variants having about 70%, 75%, 80%, 85%, 90% and 95% nucleic acid sequence identity are generated using this method. These variants are then associated with natural variation in the germplasm for component traits related to plant pathogen infection. The associated variants are used as marker haplotypes to select for the desirable traits.

The present invention also includes polynucleotides optimized for expression in different organisms. For example, for expression of the polynucleotide in a maize plant, the sequence can be altered to account for specific codon preferences and to alter GC content as according to Murray, et al, supra. Maize codon usage for 28 genes from maize plants is listed in Table 4 of Murray, et al., supra.

The plant miRNA398 or GRF1/GRF3 nucleic acids which may be used for the present invention comprise isolated plant polynucleotides which are inclusive of:
(a) a polynucleotide encoding an plant GRF1, or GRF3 polypeptide or a micro RNA 396 and conservatively modified and polymorphic variants thereof;

(b) a polynucleotide having at least 70% sequence identity with polynucleotides of (a);
(c) complementary sequences of polynucleotides of (a) or (b).
Construction of Nucleic Acids The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMClneo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).
Synthetic Methods for Constructing Nucleic Acids The isolated nucleic acids used in the methods of the present invention can also be prepared by direct chemical synthesis by methods such as the phosphotriester method of Narang, et al., (1979) Meth. Enzymol. 68:90-9; the phosphodiester method of Brown, et al., (1979) Meth. Enzymol. 68:109-51; the diethylphosphoramidite method of Beaucage, et al., (1981) Tetra. Letts. 22(20):1859-62; the solid phase phosphoramidite triester method described by Beaucage, et al., supra, e.g., using an automated synthesizer, e.g., as described in Needham-VanDevanter, et al., (1984) Nucleic Acids Res. 12:6159-68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) Nucleic Acids Res. 15:8125) and the 5<G>7 methyl GpppG RNA cap structure (Drummond, et al., (1985) Nucleic Acids Res. 13:7375). Negative elements include stable intramolecular 5' UTR stem-loop structures (Muesing, et al., (1987) Cell 48:691) and AUG sequences or short open reading frames preceded by an appropriate AUG in the 5' UTR (Kozak, supra, Rao, et al., (1988) Mol. and Cell. Biol. 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See, Devereaux, et al., (1984) Nucleic Acids Res. 12:387-395); or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention also includes the use of sequence shuffling using polynucleotides disclosed for the methods of the present invention, and compositions resulting therefrom. Sequence shuffling is described in PCT publication No. 96/19256. See also, Zhang, et al., (1997) Proc. Natl. Acad. Sci. USA 94:4504-9; and Zhao, et al., (1998) Nature Biotech 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention provides the use of recombinant expression/transcription cassettes comprising a polynucleotide for a plant microRNA396, or a GRF useful for the methods of the present invention. A nucleic acid sequence coding for the desired polynucleotide, for example a cDNA or a genomic sequence encoding a polypeptide long enough to code for an active GRF protein, or for a desired mircor RNA can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,633,439), the Nos promoter, the rubisco promoter, the GRP1-8 promoter, the 35S promoter from cauliflower mosaic virus (CaMV), as described in Odell, et al., (1985) Nature 313:810-2; rice actin (McElroy, et al., (1990) Plant Cell 163-171); ubiquitin (Christensen, et al., (1992) Plant Mol. Biol. 12:619-632 and Christensen, et al., (1992) Plant Mol. Biol. 18:675-89); pEMU (Last, et al., (1991) Theor. Appl. Genet. 81:581-8); MAS (Velten, et al., (1984) EMBO J. 3:2723-30); and maize H3 histone (Lepetit, et al., (1992) Mol. Gen. Genet. 231:276-85; and Atanassvoa, et al., (1992) Plant Journal 2(3):291-300); ALS promoter, as described in PCT Application No. WO 96/30530; and other transcription initiation regions from various plant genes known to those of skill. For the present invention ubiquitin is the preferred promoter for expression in monocot plants.

Alternatively, the plant promoter can direct expression in a specific tissue or may be otherwise under more precise environmental or developmental control. Such promoters are referred to here as "inducible" promoters. Environmental conditions that may affect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) Nucleic Acids Res. 12:369-85); the potato proteinase inhibitor II (PINII) gene (Keil, et al., (1986) Nucleic Acids Res. 14:5641-50; and An, et al., (1989) Plant Cell 1:115-22); and the CaMV 19S gene (Mogen, et al., (1990) Plant Cell 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) Mol. Cell Biol. 8:4395-4405; Callis, et al., (1987) Genes Dev. 1:1183-200). Such intron enhancement of gene expression is typically greatest when placed near the 5' end of the transcription unit. Use of maize introns Adh1-S intron 1, 2 and 6, the Bronze-1 intron are known in the art. See generally, The Maize Handbook, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos, et al., (1989) J. Biol. Chem. 264:4896-900), such as the *Nicotiana plumbaginifolia* extension gene (DeLoose, et al., (1991) Gene 99:95-100); signal peptides which target proteins to the vacuole, such as the sweet potato sporamin gene (Matsuka, et al., (1991) Proc. Natl. Acad. Sci. USA 88:834) and the barley lectin gene (Wilkins, et al., (1990) Plant Cell, 2:301-13); signal peptides which cause proteins to be secreted, such as that of PRIb (Lind, et al., (1992) Plant Mol. Biol. 18:47-53) or the barley alpha amylase (BAA) (Rahmatullah, et al., (1989) Plant Mol. Biol. 12:119, and hereby incorporated by reference), or signal peptides which target proteins to the plastids such as that of rapeseed enoyl-Acp reductase (Verwaert, et al., (1994) Plant Mol. Biol. 26:189-202) are useful in the invention.

The vector comprising the sequences from a plant microRNA396, GRF1 or GRF3 will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al. (1987), Meth. Enzymol. 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) Gene 61:1-11, and Berger, et al., (1989) Proc. Natl. Acad. Sci. USA, 86:8402-6. Another useful vector herein is plasmid pBI101.2 that is available from CLONTECH Laboratories, Inc. (Palo Alto, Calif.).

Expression of Proteins in Host Cells

Using the methods of the present invention, one may express an miRNA396 or GRF protein in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a GRF1 or GRF3 protein or microRNA will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about $1/10,000$ transcripts to about $1/100,000$ transcripts to about $1/500,000$ transcripts. Conversely, a "strong promoter" drives expression of a coding sequence at a "high level," or about $1/10$ transcripts to about $1/100$ transcripts to about $1/1,000$ transcripts.

One of skill would recognize that modifications could be made to a GRF protein or MicroRNA without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) Nature 198: 1056), the tryptophan (trp) promoter system (Goeddel, et al., (1980) Nucleic Acids Res. 8:4057) and the lambda derived P L promoter and N-gene ribosome binding site (Shimatake, et al., (1981) Nature 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) Gene 22:229-35; Mosbach, et al., (1983) Nature 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) Methods in Yeast Genetics, Cold Spring Harbor Laboratory is a well-recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A plant protein, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding plant GRF proteins or miRNA396 can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) Immunol. Rev. 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas ($7^{th}$ ed., m 1992).

Appropriate vectors for expressing proteins of the present invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) J. Embryol. Exp. Morphol. 27:353-65).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al., J. Virol. 45:773-81 (1983)). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in DNA Cloning: A Practical Approach, vol. II, Glover, ed., IRL Press, Arlington, Va., pp. 213-38 (1985)).

In addition, the plant GRF or miRNA396 gene placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert a plant miRNA396 or GRF encoding polynucleotide into a plant host, including biological and physical plant transformation protocols. See, e.g., Miki et al., "Procedure for Introducing Foreign DNA into Plants," in Methods in Plant Molecular Biology and Biotechnology, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., Science 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in Methods in Plant Molecular Biology and Biotechnology, supra, pp. 89-119.

The isolated plant polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) Biotechniques 4:320-334; and U.S. Pat. No. 6,300,543), electroporation (Riggs, et al., (1986) Proc. Natl. Acad. Sci. USA 83:5602-5606, direct gene transfer (Paszkowski et al., (1984) EMBO J. 3:2717-2722), and ballistic particle acceleration (see, for example, Sanford, et al., U.S. Pat. No. 4,945,050; WO 91/10725; and McCabe, et al., (1988) Biotechnology 6:923-926). Also see, Tomes, et al., "Direct DNA Transfer into Intact Plant Cells Via Microprojectile Bombardment". pp. 197-213 in Plant Cell, Tissue and Organ Culture, Fundamental Methods. eds. 0. L. Gamborg & G. C. Phillips. Springer-Verlag Berlin Heidelberg New York, 1995; U.S. Pat. No. 5,736,369 (meristem); Weissinger, et al., (1988) Ann. Rev. Genet. 22:421-477; Sanford, et al., (1987) Particulate Science and Technology 5:27-37 (onion); Christou, et al., (1988) Plant Physiol. 87:671-674 (soybean); Datta, et al., (1990) Biotechnology 8:736-740 (rice); Klein, et al., (1988) Proc. Natl. Acad. Sci. USA 85:4305-4309 (maize); Klein, et al., (1988) Biotechnology 6:559-563 (maize); WO 91/10725 (maize); Klein, et al., (1988) Plant Physiol. 91:440-444 (maize); Fromm, et al., (1990) Biotechnology 8:833-839; and Gordon-Kamm, et al., (1990) Plant Cell 2:603-618 (maize); Hooydaas-Van Slogteren & Hooykaas (1984) Nature (London) 311:763-764; Bytebierm, et al., (1987) Proc. Natl. Acad. Sci. USA 84:5345-5349 (Liliaceae); De Wet, et al., (1985) In The Experimental Manipulation of Ovule Tissues, ed. G. P. Chapman, et al., pp. 197-209. Longman, N.Y. (pollen); Kaeppler, et al., (1990) Plant Cell Reports 9:415-418; and Kaeppler, et al., (1992) Theor. Appl. Genet. 84:560-566 (whisker-mediated transformation); U.S. Pat. No. 5,693,512 (sonication); D'Halluin, et al., (1992) Plant Cell 4:1495-1505 (electroporation); Li, et al., (1993) Plant Cell Reports 12:250-255; and Christou and Ford, (1995) Annals of Botany 75:407-413 (rice); Osjoda, et al., (1996) Nature Biotech. 14:745-750; *Agrobacterium* mediated maize transformation (U.S. Pat. No. 5,981,840); silicon carbide whisker methods (Frame, et al., (1994) Plant J. 6:941-948); laser methods (Guo, et al., (1995) Physiologia *Plantarum* 93:19-24); sonication methods (Bao, et al., (1997) Ultrasound in Medicine & Biology 23:953-959; Finer and Finer, (2000) Lett Appl Microbiol. 30:406-10; Amoah, et al., (2001) J Exp Bot 52:1135-42); polyethylene glycol methods (Krens, et al., (1982) Nature 296:72-77); protoplasts of monocot and dicot cells can be transformed using electroporation (Fromm, et al., (1985) Proc. Natl. Acad. Sci. USA 82:5824-5828) and microinjection (Crossway, et al., (1986) Mol. Gen. Genet. 202:179-185); all of which are herein incorporated by reference.

Agrobacterium-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) Crit. Rev. Plant Sci. 10:1. Descriptions of the *Agrobacterium* vector systems and methods for *Agrobacterium*-mediated gene transfer are provided in Gruber, et al., supra; Miki, et al., supra; and Moloney, et al., (1989) Plant Cell Reports 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) Science 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. Pat. No. 913,914, filed Oct. 1, 1986, as referenced in U.S. Pat. No. 5,262,306, issued Nov. 16, 1993; and Simpson, et al., (1986) Plant Mol. Biol. 6:403-15 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using *Agrobacterium*. European Application No. 672 752 A1 discloses a method for transforming monocots with *Agrobacterium* using the scutellum of immature embryos. Ishida, et al., discuss a method for transforming maize by exposing immature embryos to *A. tumefaciens* (Nature Biotechnology 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) Theor. Appl. Genet. 69:235-40; U.S. Pat. No. 4,658,082; Simpson, et al., supra; and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) The Plant Journal 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) Part. Sci. Technol. 5:27; Sanford, (1988) Trends Biotech 6:299; Sanford, (1990) Physiol. Plant 79:206; and Klein, et al., (1992) Biotechnology 10:268).

Another method for physical delivery of DNA to plants is sonication of target cells as described in Zang, et al., (1991) BioTechnology 9:996. Alternatively, liposome or spheroplast fusions have been used to introduce expression vectors into plants. See, e.g., Deshayes, et al., (1985) EMBO J. 4:2731; and Christou, et al., (1987) Proc. Natl. Acad. Sci. USA 84:3962. Direct uptake of DNA into protoplasts using $CaCl_2$ precipitation, polyvinyl alcohol, or poly-L-ornithine has also been reported. See, e.g., Hain, et al., (1985) Mol. Gen. Genet. 199:161; and Draper, et al., (1982) Plant Cell Physiol. 23:451. Electroporation of protoplasts and whole cells and tissues has also been described. See, e.g., Donn, et al., (1990) Abstracts of the VIIth Int'l. Congress on Plant Cell and Tissue Culture IAPTC, A2-38, p. 53; D'Halluin, et al., (1992) Plant Cell 4:1495-505; and Spencer, et al., (1994) Plant Mol. Biol. 24:51-61.

Some embodiments may involve the improvement in nematode tolerance by modulating the expression of a plant miRNA396, GRF1/GRF3 in a way that decreases the activity/expression of the protein or mircroRNA.

Reducing the Activity of a Plant GRF Polypeptide or MicroRNA

Methods are also provided to reduce or eliminate the activity of a plant GRF Polypeptide or MicroRNA by transforming a plant cell with an expression cassette that expresses a polynucleotide that inhibits the expression of the plant polypeptide or microRNA. The polynucleotide may inhibit the expression of the plant a plant GRF Polypeptide or MicroRNA directly, by preventing transcription or translation of the plant messenger RNA, or indirectly, by encoding a polypeptide that inhibits the transcription or translation of an plant a plant GRF Polypeptide or MicroRNA gene encoding an plant a plant GRF Polypeptide or MicroRNA. Methods for inhibiting or eliminating the expression of a gene in a plant are well known in the art, and any such method may be used in the present invention to inhibit the expression of the plant a plant GRF Polypeptide or MicroRNA. Many methods may be used to reduce or eliminate the activity of GRF polypeptides. In addition, more than one method may be used to reduce the activity of a plant GRF Polypeptide or MicroRNA.

1. Polynucleotide-Based Methods:

In some embodiments of the present invention, a plant is transformed with an expression cassette that is capable of expressing a polynucleotide that inhibits the expression of a plant GRF Polypeptide or MicroRNA of the invention. For example, for the purposes of the present invention, an expression cassette capable of expressing a polynucleotide that inhibits the expression of at least one a plant GRF Polypeptide or MicroRNA is an expression cassette capable of producing an RNA molecule that inhibits the transcription and/or translation of at least one plant a plant GRF Polypeptide or MicroRNA of the invention.

Examples of polynucleotides that inhibit the expression of a plant GRF Polypeptide or MicroRNA include sense suppression/cosuppresion. In cosuppression, an expression cassette is designed to express an RNA molecule corresponding to all or part of a messenger RNA encoding a plant GRF Polypeptide or MicroRNA in the "sense" orientation. Over expression of the RNA molecule can result in reduced expression of the native gene. The polynucleotide used for cosuppression may correspond to all or part of the sequence encoding the a plant GRF Polypeptide or MicroRNA, all or part of the 5' and/or 3' untranslated region of a plant GRF Polypeptide or MicroRNA transcript, or all or part of both the coding sequence and the untranslated regions of a transcript encoding a plant GRF Polypeptide or MicroRNA. In some embodiments where the polynucleotide comprises all or part of the coding region for the plant a plant GRF Polypeptide or MicroRNA, the expression cassette is designed to eliminate the start codon of the polynucleotide so that no protein product will be translated.

In some embodiments of the invention, inhibition of the expression of a plant GRF Polypeptide or MicroRNA may be obtained by antisense suppression. For antisense suppression, the expression cassette is designed to express an RNA molecule complementary to all or part of a messenger RNA encoding the a plant GRF Polypeptide or MicroRNA. Over expression of the antisense RNA molecule can result in reduced expression of the native gene. The polynucleotide for use in antisense suppression may correspond to all or part of the complement of the sequence encoding the a plant GRF Polypeptide or MicroRNA, all or part of the complement of the 5' and/or 3' untranslated region of the plant a plant GRF Polypeptide or MicroRNA transcript, or all or part of the complement of both the coding sequence and the untranslated regions of a transcript encoding the plant a plant GRF Polypeptide or MicroRNA. In addition, the antisense polynucleotide may be fully complementary (i.e., 100% identical to the complement of the target sequence) or partially complementary (i.e., less than 100% identical to the complement of the target sequence) to the target sequence.

In some embodiments of the invention, inhibition of the expression of a plant GRF Polypeptide or MicroRNA may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of plant a plant GRF Polypeptide or MicroRNA. Methods for using dsRNA interference to inhibit the expression of endogenous plant genes are described in Waterhouse, et al., (1998) Proc. Natl. Acad. Sci. USA 95:13959-13964, Liu, et al., (2002) Plant Physiol. 129:1732-1743, and WO 99/49029, WO 99/53050, WO 99/61631, and WO 00/49035; each of which is herein incorporated by reference.

In some embodiments of the invention, inhibition of the expression of a plant GRF Polypeptide or MicroRNA may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) Nat. Rev. Genet. 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) Proc. Natl. Acad. Sci. USA 97:4985-4990; Stoutjesdijk, et al., (2002) Plant Physiol. 129:1723-1731; and Waterhouse and Helliwell, (2003) Nat. Rev. Genet. 4:29-38. Methods for using hpRNA interference to inhibit or silence the expression of genes are described, for example, in Chuang and Meyerowitz, (2000) Proc. Natl. Acad. Sci. USA 97:4985-4990; Stoutjesdijk, et al., (2002) Plant Physiol. 129:1723-1731; Waterhouse and Helliwell, (2003) Nat. Rev. Genet. 4:29-38; Pandolfini et al., BMC Biotechnology 3:7, and U.S. Patent Publication No. 2003/0175965; each of which is herein incorporated by reference. A transient assay for the efficiency of hpRNA constructs to silence gene expression in vivo has been described by Panstruga, et al., (2003) Mol. Biol. Rep. 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) Nature 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) Nature 407:319-320; Wesley, et al., (2001) Plant J. 27:581-590; Wang and Waterhouse, (2001) Curr. Opin. Plant Biol. 5:146-150; Waterhouse and Helliwell, (2003) Nat. Rev. Genet. 4:29-38; Helliwell and Waterhouse, (2003) Methods 30:289-295, and U.S. Patent Publication No. 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904; Mette, et al., (2000) EMBO J 19:5194-5201; Matzke, et al., (2001) Curr. Opin. Genet. Devel. 11:221-227; Scheid, et al., (2002) Proc. Natl. Acad. Sci., USA 99:13659-13662; Aufsaftz, et al., (2002) Proc. Nat'l. Acad. Sci. 99(4):16499-16506; Sijen, et al., Curr. Biol. (2001) 11:436-440), herein incorporated by reference.

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence. Methods of using amplicons to inhibit the expression of endogenous plant genes are described, for example, in Angell and Baulcombe, (1997) EMBO J. 16:3675-3684, Angell and Baulcombe, (1999) Plant J. 20:357-362, and U.S. Pat. No. 6,635,805, each of which is herein incorporated by reference.

In some embodiments, the polynucleotide expressed by the expression cassette of the invention is catalytic RNA or has ribozyme activity specific for the messenger RNA of the plant miRNA396 or GRF polypeptide. Thus, the polynucleotide causes the degradation of the endogenous messenger RNA, resulting in reduced expression of the plant GRF polypeptide or miRNA396. This method is described, for example, in U.S. Pat. No. 4,987,071, herein incorporated by reference.

In some embodiments of the invention, inhibition of the expression of a plant GRF Polypeptide or MicroRNA activity may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) Nature 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding a plant GRF Polypeptide or MicroRNA, resulting in reduced expression of the gene. In particular embodiments, the zinc finger protein binds to a regulatory region a plant GRF Polypeptide or MicroRNA gene. In other embodiments, the zinc finger protein binds to a messenger RNA encoding a plant GRF Polypeptide or MicroRNA and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 2003/0037355; each of which is herein incorporated by reference.

3. Polypeptide-Based Inhibition of Protein Activity

In some embodiments of the invention, the polynucleotide encodes an antibody that binds to at least one a plant GRF Polypeptide or MicroRNA, and reduces the activity of the a plant GRF Polypeptide or MicroRNA. In another embodiment, the binding of the antibody results in increased turnover of the antibody-GRF Polypeptide or MicroRNA complex by cellular quality control mechanisms. The expression of antibodies in plant cells and the inhibition of molecular pathways by expression and binding of antibodies to proteins in plant cells are well known in the art. See, for example, Conrad and Sonnewald, (2003) Nature Biotech. 21:35-36, incorporated herein by reference.

4. Gene Disruption

In some embodiments of the present invention, the activity of a plant GRF Polypeptide or MicroRNA is reduced or eliminated by disrupting the gene encoding a plant GRF Polypeptide or MicroRNA. The gene encoding the plant a plant GRF Polypeptide or MicroRNA may be disrupted by any method known in the art. For example, in one embodiment, the gene is disrupted by transposon tagging. In another embodiment, the gene is disrupted by mutagenizing plants using random or targeted mutagenesis, and selecting for plants that have increased nematode tolerance.

i. Transposon Tagging

In one embodiment of the invention, transposon tagging is used to reduce or eliminate a plant GRF Polypeptide or MicroRNA activity of one or more plant GRF Polypeptides or MicroRNA polypeptides. Transposon tagging comprises inserting a transposon within an endogenous plant a plant GRF Polypeptide or MicroRNA gene to reduce or eliminate expression of the plant a plant GRF Polypeptide or MicroRNA.

In this embodiment, the expression of one or more a plant GRF Polypeptide or MicroRNA is reduced or eliminated by inserting a transposon within a regulatory region or coding region of the gene encoding a plant GRF Polypeptide or MicroRNA. A transposon that is within an exon, intron, 5' or 3' untranslated sequence, a promoter, or any other regulatory sequence of a plant GRF Polypeptide or MicroRNA gene may be used to reduce or eliminate the expression and/or activity of the encoded a plant GRF Polypeptide or MicroRNA.

Methods for the transposon tagging of specific genes in plants are well known in the art. See, for example, Maes, et al., (1999) Trends Plant Sci. 4:90-96; Dharmapuri and Sonti, (1999) FEMS Microbiol. Lett. 179:53-59; Meissner, et al., (2000) Plant J. 22:265-274; Phogat, et al., (2000) J. Biosci. 25:57-63; Walbot, (2000) Curr. Opin. Plant Biol. 2:103-107; Gai, et al., (2000) Nucleic Acids Res. 28:94-96; Fitzmaurice, et al., (1999) Genetics 153:1919-1928). In addition, the TUSC process for selecting Mu insertions in selected genes has been described in Bensen, et al., (1995) Plant Cell 7:75-84; Mena, et al., (1996) Science 274:1537-1540; and U.S. Pat. No. 5,962,764; each of which is herein incorporated by reference.

ii. Mutant Plants with Reduced Transcription/Translation/Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) Virology 243:472-481; Okubara, et al., (1994) Genetics 137:867-874; and Quesada, et al., (2000) Genetics 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) Nat. Biotechnol. 18:455-457, herein incorporated by reference.

Mutations that impact gene expression or that interfere with the function of the encoded protein are well known in the art. Insertional mutations in gene exons usually result in null-mutants. Mutations in conserved residues are particularly effective in inhibiting the activity of the encoded protein. Conserved residues of plant GRF polypeptides and/or miRNA396 suitable for mutagenesis with the goal to eliminate activity have been described. Such mutants can be isolated according to well-known procedures, and mutations in different loci can be stacked by genetic crossing. See, for example, Gruis, et al., (2002) Plant Cell 14:2863-2882.

The methods of the invention provides for improved plant tolerance to nematode infection. This performance may be demonstrated in a number of ways including the following.

Improved or Modulated Root Development in Nematode Infected Plants

Methods for improving tolerance to nematode infection and root development in a plant are provided. By "modulating root development" is intended any alteration in the development of the plant root under nematode infection when compared to a control plant. Such alterations in root development include, but are not limited to, alterations in the growth rate of the primary root, the fresh root weight, the extent of lateral and adventitious root formation, the vasculature system, meristem development, or radial expansion.

The methods comprise modulating the level and/or activity of a miRNA396, GRF1 or GRF3 and their interaction in the plant. In one method, a plant miRNA396 sequence expression construct is provided to the plant. In other methods, root development is modulated by increasing the level or activity of the GRF proteins that interact with miRNA396 in the plant. A change in plant GRF activity can result in at least one or more of the following alterations to root development, including, but not limited to, alterations in root biomass and length when the plant is grown under nematode infection.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, U.S. Application No. 2003/0074698 and Werner, et al., (2001) PNAS 18:10487-10492, both of which are herein incorporated by reference. As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass in the presence of nematode infection by increasing the activity and/or level of miRNA396 or its targets such as the GRF proteins also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. Furthermore, higher root biomass production has a direct effect on the yield and an indirect effect of production of compounds produced by root cells or transgenic root cells or cell cultures of said transgenic root cells.

Modulating Shoot and Leaf Development in Nematode Infected Plants

Methods are also provided for modulating shoot and leaf development in a plant, particularly under nematode infection. By "modulating shoot and/or leaf development" is intended any alteration in the development of the plant shoot and/or leaf in nematode infection. Such alterations in shoot and/or leaf development include, but are not limited to, alterations in shoot meristem development, in leaf number, leaf size, leaf and stem vasculature, internode length, and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) PNAS 98:10487-10492 and U.S. Application No. 2003/0074698, each of which is herein incorporated by reference.

The method for modulating shoot and/or leaf development in a plant in nematode infected conditions comprises increasing the activity and/or level of plant mrRNA396 or its target GRF proteins. In one embodiment, the plant nucleotide sequences can be provided by introducing into the plant a polynucleotide comprising an plant expression construct, expressing the same, and thereby modifying shoot and/or leaf development in nematode infected plants. In other embodiments, the plant expression nucleotide construct introduced into the plant is stably incorporated into the genome of the plant.

An increase in plant tolerance to nematode infection can result in at least one or more of the following alterations in shoot and/or leaf development under nematode infection when compared to a nonmodified plant, including, but not limited to, changes in leaf number, altered leaf surface, altered vasculature, internodes and plant growth, and alterations in leaf senescence, when compared to a control plant in the same conditions.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters, and leaf-preferred promoters. Exemplary promoters have been disclosed elsewhere herein.

Method of Use for Plant miRNA, and/or GRF Polynucleotides in Combination with Other Phenotype Changing Polynucleotides The nucleotides, expression cassettes and methods disclosed herein are useful in regulating expression of any heterologous nucleotide sequence in a host plant in order to vary the phenotype of a plant. Various other changes in phenotype are of interest including modifying the fatty acid composition in a plant, altering the amino acid content of a plant, altering a plant's stress tolerance, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

In certain embodiments the plant miRNA/GRF nucleic acid sequences of can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703, 049); barley high lysine (Williamson, et al., (1987) Eur. J. Biochem. 165:99-106; and WO 98/20122); and high methionine proteins (Pedersen, et al., (1986) J. Biol. Chem. 261: 6279; Kirihara, et al., (1988) Gene 71:359; and Musumura, et al., (1989) Plant Mol. Biol. 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,736,514; 5,723,756; 5,593,881; Geiser, et al., (1986) Gene 48:109); lectins (Van Damme, et al., (1994) Plant Mol. Biol. 24:825); fumonisin detoxification genes (U.S. Pat. No. 5,792,931); avirulence and disease resistance genes (Jones, et al., (1994) Science 266:789; Martin, et al., (1993) Science 262:1432; Mindrinos, et al., (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) J. Bacteriol. 170:5837-5847) facilitate expression of polyhydroxyalkanoates (PHAs)), the disclosures of which are herein incorporated by reference.

One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias, et al., (1996) Plant Cell 8:1533-44); AKT1, a component of the potassium uptake apparatus in *Arabidopsis*, (Spalding, et al., (1999) J Gen Physiol 113:909-18); RML genes which activate cell division cycle in the root apical cells (Cheng, et al., (1995) Plant Physiol 108:881); maize glutamine synthetase genes (Sukanya, et al., (1994) Plant Mol Biol 26:1935-46) and hemoglobin (Duff, et al., (1997) J. Biol. Chem 27:16749-16752, Arredondo-Peter, et al., (1997) Plant Physiol. 115:1259-1266; Arredondo-Peter, et al., (1997) Plant Physiol 114:493-500 and references sited therein). The sequence of interest may also be useful in expressing antisense nucleotide sequences of genes that that negatively affects root development.

Additional, agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) Eur. J. Biochem. 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) Proceedings of the World Congress on Vegetable Protein Utilization in Human Foods and Animal Feedstuffs, ed. Applewhite (American Oil Chemists Society, Champaign, Ill.), pp. 497-502; herein incorporated by reference); corn (Pedersen, et al., (1986) J. Biol. Chem. 261:6279; Kirihara, et al., (1988) Gene 71:359; both of which are herein incorporated by reference); and rice (Musumura, et al., (1989) Plant Mol. Biol. 12:123, herein incorporated by reference). Other agronomically important genes encode latex, Floury 2, growth factors, seed storage factors, and transcription factors.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) J. Bacteriol. 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on polypeptides encoded by the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use a bar-bialaphos or the EPSPS-glyphosate selective system, for example, transformed tissue can be cultured for 0-28 days on nonselective medium and subsequently transferred to medium containing from 1-3 mg/1 bialaphos or 1-3 mM glyphosate as appropriate. While ranges of 1-3 mg/1 bialaphos or 1-3 mM glyphosate may be preferred, it is proposed that ranges of 0.1-50 mg/1 bialaphos or 0.1-50 mM glyphosate will find utility.

Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 μl agarose. In embryo rescue, large embryos (defined as greater than 3 mm in length) are germinated directly on an appropriate media. Embryos smaller than that may be cultured for 1 wk on media containing the above ingredients along with $10^{-5M}$ abscisic acid and then transferred to growth regulator-free medium for germination.

Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discrete fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

Breeding Plants

In addition to direct transformation of a particular plant genotype with a construct prepared according to the current invention, transgenic plants may be made by crossing a plant having a selected DNA of the invention to a second plant lacking the construct. For example, a selected polypeptide coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

It is understood that modifications which do not substantially affect the activity the various embodiments of this invention are also provided within the definition of the invention provided herein. Accordingly, the following examples are intended to illustrate but not limit the present invention.

EXAMPLES

Example 1

Pathogens alter their hosts' biology to ensure successful infection. Such modifications range from moderate to extensive, and in the case of plant pathogens, few infections result in more dramatic changes than those of sedentary endoparasitic nematodes, which include the cyst nematodes (*Heterodera* spp.). Maybe rivaled in complexity only by plant interactions with *Agrobacterium* and *Rhizobia*, cyst nematodes are obligate parasitic roundworms that induce the formation of novel plant cell types that are associated in a unique feeding organ, the syncytium.

Cyst nematodes infect as second-stage juveniles (J2), which initiate the induction/formation of the syncytium. During this phase, J2s begin feeding on the growing syncytium and then develop into third-stage (J3) and fourth-stage juveniles (J4) followed by the adult stage. Syncytium development can be separated into an induction/formation phase followed by a maintenance phase. Induction/formation involves effector-mediated communication between the nematode and plant cells leading to cytoplasmic and nuclear changes followed by successive cell-to-cell fusions of the cells surrounding an initial feeding cell (IFC). Through continuous cell fusions, syncytium formation and enlargement continues. During the maintenance phase no additional cells are incorporated and syncytial cells have undergone their developmental changes and now are fully engaged in maintaining syncytium function.

Due to their sedentary nature of parasitism, cyst nematodes need to obtain all their nourishment from one location, in fact, through the contact with the IFC. The severity of this constraint becomes obvious when considering that the worm-shaped infective J2 nematode has a body length of approximately 500 um and then grows to a large lemon-shaped sphere that produces several hundred eggs, each containing a fully infective nematode. The sheer logistics of nutrient availability and flux appear unrivalled for an individual plant pathogen. This association is also impressive with regard to the complete dependence of nematode survival on the well-being and survival of the IFC and the syncytium. In other words, a single hypersensitive response or an interruption of the newly induced developmental programs of syncytium formation would eliminate nematode parasitism. But despite a plant's well developed ability to detect and defend against invaders, co-evolution of nematode and plant has resulted in an uncannily robust and successful pathosystem in which nematode contact with the IFC does not trigger effective defenses. Instead, syncytial cells are dedicated to nematode nourishment, and their plant defenses have been suppressed by the nematode.

Syncytium formation encompasses reprogramming of differentiated root cells, and these redifferentiations are accompanied and mediated by massive gene expression changes, which have been documented in diverse research approaches using soybean and the soybean cyst nematode *Heterodera glycines* (Alkharouf et al., 2006; Ithal et al., 2007; Klink et al., 2009) and probably most extensively in *Arabidopsis* infected by the sugar beet cyst nematode *H. schachtii* (Szakasits et al., 2009). These gene expression changes clearly require powerful mechanisms of concerted regulation, and the existence of major regulatory choke points, i.e., master switches, can be hypothesized, although none have been documented to date. Regulatory networks governing gene expression patterns in nematode-infected roots and particularly in the developing syncytium are very poorly understood.

miRNAs initially have been shown to be involved in the regulation of a variety of plant developmental processes including phase transition, hormone synthesis and signaling, pattern formation, and morphogenesis (Chen, 2009). Recent studies indicate that miRNAs and small endogenous RNAs also are involved in biotic stress responses in plants (Navarro et al. 2006; Li et al., 2010; He et al., 2008; Lu et al., 2007; Fahlgren et al. 2007; Hewezi et al., 2008a; Pandey et al., 2008; Katiyar-Agarwal et al., 2006 and 2007). Also, consistent with a role of small RNAs in the regulation of plant immune responses, *Arabidopsis* mutants deficient in siRNA or miRNA biogenesis affected plant susceptibility to bacteria (Navarro et al., 2008) and the sugar beet cyst nematode *H. schachtii* (Hewezi et al., 2008a). Collectively, these emerging data indicate that small RNA-mediated gene regulation is a fundamental mechanism in plant-pathogen interactions.

Despite these advances, little is known about the molecular mechanisms controlling cell differentiation and development in the nematode-induced syncytium. The miR396 family, miR396a and miR396b, governs the expression of seven growth regulating transcription factor genes (GRFs) (Jones-Rhoades and Bartel, 2004). The GRF gene family in *Arabidopsis* is known to act in a functionally redundant fashion to positively control cell proliferation and size in leaves (Kim et al., 2003; Kim and Kende, 2004; Horiguchi et al., 2005; Kim and Lee, 2006). Consistent with the fact that miR396 acts as a negative regulator of GRF gene expression, overexpression of miR396 negatively impacted cell proliferation in leaves and meristem size (Liu et al., 2009; Rodriguez et al., 2010). However, the roles of the miR396/GRF regulatory module in controlling developmental events during plant-pathogen interactions or in root developmental processes are completely unknown. In this study we demonstrate that miR396 is differentially expressed in the syncytium, that the miR396-GRF regulatory unit is subject to extensive feedback regulation, and that this microRNA functions as a true master switch in syncytium formation.

Results

In *Arabidopsis*, miR396 is encoded by two genes, miR396a (AT2G10606)(SEQ ID NO:1) and miR396b (AT5G35407)(SEQ ID NO:2) and regulates the expression of seven of the nine *Arabidopsis* growth regulating transcription factor genes (GRF1 through 4 and 7 through 9), which share the miR396-binding site (Jones-Rhoades and Bartel, 2004). To determine which GRF genes could be targeted by miR396 in roots, we measured the mRNA steady-state levels in root tissues of 10-d old seedlings of all 9 GRF genes by quantitative real-time RT-PCR (qPCR). GRF1 and GRF3 showed by far the highest root expression levels (FIG. 7). This observation implies that if miRNA396 is active in post-transcriptional gene regulation in *Arabidopsis* roots in general and during nematode infection in particular, GRF1 and GRF3 are its most likely targets, which is consistent with our previous findings that GRF1 and GRF3 are the genes most responsive to *H. schachtii* infection among the GRF family members (Hewezi et al., 2008a).

miR396a and miR396b have Similar Spatial Expression Patterns and Overlap with GRF1 and GRF3 Expression in Roots To examine tissue-specific expression patterns of the two miR396 genes, we generated transgenic plants expressing constructs containing the regions upstream of miRNA396 precursor sequences fused to the β-glucuronidase (GUS) reporter gene (miR396a:GUS and miR396b:GUS). GUS staining of at least four independent lines for each construct revealed that the miR396a and miR396b promoters have very similar spatial expression patterns, both in leaf and root tissues (FIG. 8). Despite the fact that miR396a and miR396b have similar spatial expression patterns, GUS staining of miR396b:GUS lines was in general much stronger than that of miR396a:GUS lines. This was confirmed by real-time RT-PCR (qPCR) analysis of miR396 precursors (pre-miR396) in roots of two-week-old Colombia-0 (Col-0) plants. We found an mRNA abundance of pre-miR396b about 70-fold higher than that of pre-miR396a. To determine whether the spatial expression of miR396 coincides with that of the GRF1 and GRF3 target genes, we generated and examined at least four transgenic lines each expressing the reporter gene fusion constructs GRF1:GUS or GRF3:GUS. Promoter activity of GRF1:GUS and GRF3:GUS (FIG. 8H) revealed that expression locations of both miR396a and miR396b spatially overlap with the expression of the target genes GRF1 and GRF3, supporting a post-transcriptional regulation of GRF1 and GRF3 by miR396 also in roots.

miRNA396 and GRF Transcription Factors Represent a Complex Regulatory Unit Governed by Multiple Mechanisms Including Feedback Regulation.

Figure 9A:
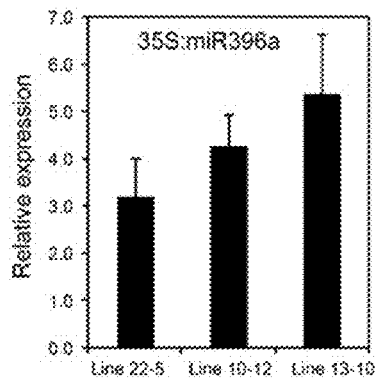
Figure 9B:
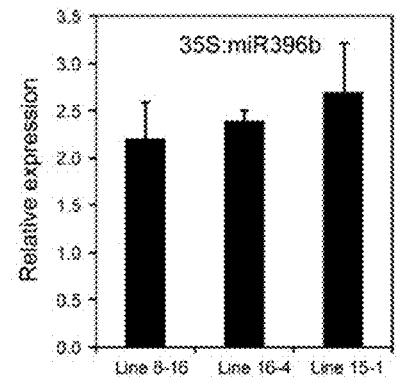
Figure 9C:
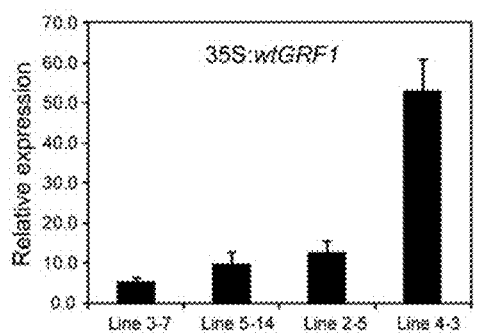
Figure 9D:
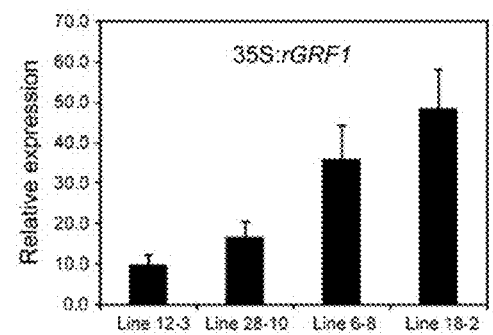
Figure 9E:
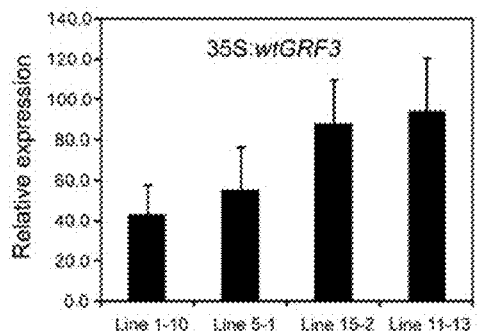
Figure 9F:
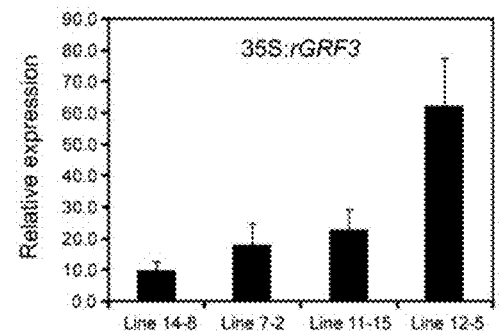

To gain insight into the effect of miR396 on GRF expression in roots, we expressed the primary miRNA sequences of both miR396a and miR396b in *Arabidopsis* under the control of the 35S promoter. Independent homozygous T3 lines expressing between 2- and 5-fold higher miRNA levels relative to the wild type were identified (FIGS. 9A and B). While we used these lines in phenotypical assessments (see below), we also determined whether miR396 overexpression resulted in the expected decreased mRNA abundance of GRF target genes by using qPCR to quantify the mRNA levels of the GRF gene family in the roots of transgenic miR396b-overexpression plants (line 16-4). All GRF gene mRNA abundances were reduced as a consequence of this manipulation (FIG. 1A). Interestingly, mRNA levels of GRF5 and GRF6 also were down regulated in the miR396 overexpression plants (1.62 and 1.68 fold, respectively), even though these genes are not directly targeted by miRNA396. These data show that miRNA396 induction results in the expected mRNA reduction of its target genes in roots but also that the GRF gene family is subject to additional concerted regulatory mechanisms that are sensitive to gene family member expression levels. Similar results in support of the latter conclusion were also obtained by Rodriguez et al. (2010) in shoots.

Having identified that miR396 is highly expressed in roots it was of interest to determine the influence of miRNA396 overexpression on root development. Interestingly, we found that overexpression of miR396 resulted in root length reductions of 12% to 49% (FIGS. 1B and C). These data suggest that GRF transcription factors are positive regulators of *Arabidopsis* root development. Given the fact that GRF1 and GRF3 are the most abundant gene family members in roots, their roles appear most prominent in this developmental pathway.

In order to further explore GRF 1 and GRF3 functions in roots, we overexpressed the coding sequences of these two genes under the control of the 35S promoter in two forms. First, we generated plants expressing the wild-type variants (35S:wtGRF1 and 35S:wtGRF3) cleavable by miRNA396 and second, we generated plants harboring miR396-resistant non-cleavable variants (35S:rGRF1 and 35S:rGRF3). While we expected that these lines would produce phenotypes opposite to those found in miR396 overexpression lines, unexpectedly, the transgenic lines overexpressing either the wild-type or the resistant versions of GRF1 and GRF3 both showed phenotypes similar to miR396 overexpression plants of shorter roots (FIGS. 1E and F). In other words, overexpression of GRF1 or GRF3 had similar effects on root morphology as the overexpression of miRNA396a or miR396b, which was counter intuitive. However, this observation was explained when we discovered that the majority of GRF genes are down regulated at the mRNA level in these GRF1 and GRF3 overexpression lines, particularly when overexpressing the variants resistant to miRNA396 (FIG. 1G). In other words, a general down regulation of GRF family members is a common feature of the rGRF1 and rGRF3 overexpression lines on one hand and the miRNA396a and miR396b overexpression lines on the other, which explains the common phenotypes. These findings illustrate again that expression levels of the GRF family members are intricately connected and that, so far unknown, mechanisms govern a mutual influence among gene family members.

Our findings that GRF1 and GRF3 overexpression resulted in a down regulation of other GRFs in theory could be reconciled by the hypothesis that GRF1 and GRF3 expression levels provide a positive feedback regulation stimulus for miRNA396 expression. I.e., elevated GRF1 and GRF3 gene expression would result in a miRNA396 induction, which would re-equilibrate the regulatory equilibrium disturbed by GRF overexpression. Similar examples of feedback regulation of miRNAs through the expression levels of their target genes recently have been identified (Gutierrez et al., 2009; Wu et al., 2009; Marin et al., 2010). We, therefore, assessed the abundances of pre-miRNA396a, pre-miRNA396b and mature miRNA396 in the 35S:wtGRF1, 35S:wtGRF3, 35S:rGRF1 and 35S:rGRF3 transgenic lines. While a miRNA396 increase in these overexpression lines would have explained the observed decreased root length as well as the decreased GRF mRNA levels, we unexpectedly measured significant decreases in abundance of miRNA396 in both of GRF1 and GRF3 overexpression lines (FIG. 1H). This observation adds additional complexity to the regulatory mechanisms not only of the GRF gene family but also the miRNA396-GRF regulatory unit. Clearly, the GRF expression changes constituted a negative feedback on the expression of miRNA396. The mutual influence of GRF family members on each other coupled with a GRF feedback on miRNA396 expression reveal a complex regulatory module for these regulatory genes.

As a final step towards understanding the regulatory mechanisms of the miRNA396-GRF system, further insight could be expected from GRF mutants. We identified two independent T-DNA insertional alleles each for GRF1

(Salk_069339C and Salk_0785 47C) and GRF3 (Salk_116709 and Salk_026786) (FIGS. 10A and B) and obtained the grf1/grf2/grf3 triple knockout mutant of Kim et al. (2003). Also here we observed counter-intuitive effects of GRF expression on miRNA396 abundance. While a simple model would imply that knocking out a miRNA target gene would result in a down-regulation of the miRNA, we observed in all mutants significant increases in miRNA abundance (FIG. 10C), which is consistent with our results obtained with the rGRF1 and rGRF3 overexpression plants showing significant decrease in miR396 expression. In summary, the miRNA396-GRF gene family system constitutes a non-trivial and complex, multi-dimensional regulatory network.

miR396a/b and GRF1 and GRF3 are Expressed in Syncytia of *Heterodera schachtii*.

We previously observed marked RNA abundance changes for miR396a/b as well as GRF1 and GRF3 following root infections by *H. schachtii* (Hewezi et al. 2008a) and, thus, it was of highest interest to identify the location of these altered expressions. We explored this question by analyzing the promoter activities of miR396a, miR396b and of the target genes GRF1 and GRF3 at different time points after *H. schachtii* infection using our transgenic *Arabidopsis* GUS lines. Most remarkably, the activities of the promoters of both miRNA396a and miR396b were strongly down-regulated in developing syncytia at early time points of *H. schachtii* infection (i.e., the parasitic J2 and early J3 stages) (FIGS. 2 A-B and E-F). At the same time, the GRF1 and GRF3 promoters became very active at the same locations (FIGS. 2 I-J and M-N). In other words, these observations of transcriptional miRNA396 down-regulation with simultaneous target gene up-regulation should result in a very pronounced peak of GRF1 and GRF3 mRNA abundance in the syncytium at the time of syncytium induction and formation.

Maybe more interestingly, after this initial early phase, the promoters of both miRNA396a and miR396b became very active in the syncytia of late J3 and J4 nematodes (FIGS. 2 C-D and G-H), thus delineating the two distinct phases of syncytium induction/formation versus syncytium maintenance. At the same time, GRF1 and GRF3 promoters remained highly active in late J3 syncytia, with only GRF3 becoming less active at the J4 stage (FIGS. 2 K-L and O-P). In other words, following the initial phase of syncytium induction/formation, GRF1 and GRF3 mRNA abundance should markedly decrease in syncytia during the maintenance phase as a function of miRNA396-mediated post-transcriptional transcript degradation.

Because the GRF gene family in *Arabidopsis* is known to act in a functionally redundant manner (Kim et al., 2003) and because GRF2 shares highest sequence similarity with GRF1, we also tested whether the GRF2 promoter is active in the syncytium. Transgenic plants expressing the reporter gene fusion GRF2:rGRF2-GUS (Rodriguez et al., 2010) were inoculated with *H. schachtii*. No GUS activity was detected in early syncytia during the J2 and early J3 infective stages (FIG. 11), while at late J3 and J4 stages very weak syncytial GUS activity was observed (FIG. 11). These observations indicate that GRF2 does not work in concert with GRF1 and GRF3 during the early induction/formation period of the syncytium. Given the overall low expression of other GRF genes in roots, similar conclusions can be drawn for the remaining GRF genes.

GRF1 and GRF3 are Post-Transcriptionally Regulated by miR396 During Nematode Infection Our promoter analyses clearly show a co-expression of miRNA396 with its GRF1 and GRF3 target genes in the syncytium, which indicates a posttranscriptional GRF expression regulation following nematode infection. To investigate any such posttranscriptional regulation of GRF1 and GRF3 by miR396, we quantified the abundances of miR396 precursors (pre-miR396a and pre-miR396b) and mature micro RNAs (miR396) along with GRF1 and GRF3 mRNA steady state levels in response to *H. schachtii* infection over time using qPCR. Ten-day-old wild-type *Arabidopsis* seedlings were inoculated with *H. schachtii*, and root tissues were collected from inoculated and non-inoculated control plants at 1, 3, 8, and 14 days post inoculation (dpi) for RNA isolation and cDNA synthesis. Data from three independent experiments revealed that the accumulation of pre-miR396a, pre-miR396b and mature miR396 was down regulated in *H. schachtii*—inoculated roots at 1 and 3 dpi time points when compared with non-inoculated roots (FIG. 3), confirming the down regulation of the miR396a/b promoters in the developing syncytium (FIG. 2). Consistent with a posttranscriptional regulation of GRF1 and GRF3, this down regulation was accompanied by elevated mRNA abundance for both GRF1 and GRF3 (FIG. 3), most probably as a result of decreased cleavage of GRF1 and GRF3 mRNA by miR396. In contrast, at 8 and 14 dpi, pre-miRNAs and mature miR396 were elevated more than 2-fold in inoculated roots (FIG. 3). Again consistent with a posttranscriptional regulation of GRF1 and GRF3, this miR396 increase was correlated with low transcript abundance of GRF1 and GRF3 (FIG. 3). In other words, despite the nematode-induced increased GRF promoter activities in syncytia (FIG. 2), GRF1 and GRF3 steady-state mRNA levels decrease in the syncytia of late J3 (8 dpi) and J4 (14 dpi) nematodes.

Overexpression of miR396 and Altered GRF Expression Modulate Nematode Susceptibility Our finding that miR396 and GRF1 and GRF3 are differentially expressed in syncytia strongly suggests that miR396-mediated regulation of GRFs is of importance in the plant-nematode interaction, and the timing of these expression changes implies a possible function in the early events of syncytium induction/formation and even a delineation of the transition from a period of syncytium initiation/formation to the period of syncytium maintenance. To test this hypothesis, we determined the effect of miR396 overexpression on nematode susceptibility using our homozygous T3 lines overexpressing miR396a or miR396b. Ten-day-old plants were inoculated with *H. schachtii* J2, and the number of adult females was counted 3 weeks after inoculation for both the transgenic lines and the wild-type control and used to quantify plant susceptibility. A remarkable effect of miR396 overexpression on nematode susceptibility was observed. All transgenic lines overexpressing miR396a (FIG. 4A) or miR396b (FIG. 4B) were dramatically less susceptible than the wild-type control, as shown by the statistically significant reduction in number of females per root system.

It appeared most logic that this reduction of susceptibility in miRNA396 overexpression lines is mediated through a resultant down-regulation of GRFs, particularly GRF1 and GRF3. Therefore, we hypothesized that mutants of GRF1 and GRF3 will phenocopy the decreased nematode susceptibility of miRNA396 overexpression lines. The single knockdown mutants of GRF1 and GRF3 exhibited small or no effects on nematode susceptibility (FIG. 4C), confirming the previously reported results of Kim et al. (2003) that GRF gene family members are functionally redundant. However, the grf1/grf2/grf3 triple knockout mutant (Kim et al., 2003) showed a statistically significant decrease in susceptibility to

*H. schachtii* relative to the wild-type control (FIG. 4D), supporting our hypothesis that the low susceptibility phenotypes of miR396a/b overexpression lines are mediated by a post-transcriptional down-regulation of GRF1 and GRF3 in the syncytium.

In order to take this analysis one step further, we also assessed the susceptibility of the *Arabidopsis* lines overexpressing the wild type or the resistant versions of GRF1 and GRF3. As we have shown above, these lines unexpectedly phenocopied the miRNA396 overexpression lines by showing reduced root length and down regulation of other GRFs. Therefore, it was interesting to determine if also nematode susceptibility would follow the same direction. We therefore tested 35S:wtGRF1, 35S:rGRF1, 35S:wtGRF3, and 35S:rGRF3 homozygous T3 lines in nematode susceptibility assays. All tested lines exhibited significantly reduced susceptibility relative to wild-type plants (FIG. 4E-H). These results again firmly connect GRF transcription factors, particularly GRF1 and GRF3, to determining the outcome of the cyst nematode—*Arabidopsis* interaction.
miR396 and its Target Genes GRF1 and GRF3 Control Syncytium Size and Nematode Development.

In addition to merely determining the number of females that mature on the different *Arabidopsis* genotypes, it is of particular interest to elucidate when and how altered susceptibility phenotypes are established. For this purpose, we measured syncytium sizes and quantified different nematode developmental stages at different assessment times. Two weeks post-inoculation, we measured the size of fully formed syncytia in transgenic plants overexpressing miR396b or the resistant versions of GRF1 or GRF3 as well as in wild-type *Arabidopsis*. Interestingly, the syncytia formed in the transgenic lines were significantly smaller than those in the wild-type control (FIG. 5A). The average reduction in syncytium size was up to 33% in miR396-overexpression plants and 19% and 14% in the transgenic plants expressing rGRF1 and rGRF3, respectively. These results indicate that the mode of action responsible for the reduced susceptibility in the transgenic lines overexpressing miR396 or the target genes GRF1 and GRF3 is manifested during the formation phase of the syncytium, i.e., at early stages of parasitism.

To investigate whether the activity of miR396 and its target genes GRF1 and GRF3 are associated with arrested nematode development at a specific stage of parasitism, we counted the number of parasitic J2/J3 at 7 dpi in the transgenic lines overexpressing miR396 or the target genes rGRF1 and rGRF3. The number of developing (i.e., already swollen) J2 and J3 was significantly reduced in these transgenic plants relative to the wild-type control (FIG. 5B), and the reduction ranged between 42% for miR396 overexpressing plants and 20% and 39% for the transgenic plants expressing rGRF1 and rGRF3, respectively. These reductions in nematode numbers were also evident when the number of J4 was counted at 21 dpi in the same plants (FIG. 5C). In fact, the percentages of nematode reduction were not significantly changed from the 7 dpi assessment. These data indicate that the reduced susceptibility of these transgenic lines is associated with early arrested nematode development during the J2/J3 stages, which again points to a mode of action during the early stages of parasitism when the syncytium is being formed.
Identification of Potential Targets of GRF1 and GRF3 Using Microarray Analysis Because both GRF1 and GRF3 function as transcription factors, identifying their direct or indirect target genes will elucidate the pathways in which these transcription factors function. To this end, we used *Arabidopsis* Affymetrix ATH1 GeneChips to compare the mRNA profiles of root tissues of the grf1/grf2/grf3 triple mutant and transgenic plants expressing rGRF1 or rGRF3 with those of the corresponding wild-type (Col-0 or Ws). We identified 3,944, 2,293 and 2,410 genes as differentially expressed in the grf1/grf2/grf3 triple mutant, rGRF1 and rGRF3 plants, respectively, at a false discovery rate (FDR) of <5% and a P value of <0.05 (Table S1A-C). In order to mine these expression data for the most likely GRF-dependent target gene candidates, we hypothesized that bona fide target genes of GRF1 and GRF3 likely would exhibit opposite expression patterns in the grf1/grf2/grf3 triple mutant and rGRF1 or rGRF3 overexpression plants. We first compared the differentially expressed genes in grf1/grf2/grf3 triple mutant (3,944 genes) with those identified as differentially expressed in rGRF1 (2,293 genes) (FIG. 6A). We identified 1,135 overlapping genes of which 1,098 had opposite expression patterns in both lines (FIG. 6B). Of these 1,098 genes, 507 genes were found to be up regulated in rGRF1 and down regulated in grf1/grf2/grf3 triple mutant, and 591 genes were up regulated in the grf1/grf2/grf3 mutant and down regulated in rGRF1 (FIG. 6B and Table S1D). Similarly, we compared the differentially expressed genes of the grf1/grf2/grf3 triple mutant (3,944 genes) with those identified as differentially expressed in rGRF3 (2,410 genes) (FIG. 6A). We identified 796 overlapping genes of which 600 have opposite expression patterns in rGRF3 and grf1/grf2/grf3 triple mutant, and of these, 299 genes were found to be up regulated in rGRF3 and down regulated in grf1/grf2/grf3 triple mutant, and 301 genes were up regulated in the grf1/grf2/grf3 triple mutant and down regulated in rGRF3 (FIG. 6C). We considered these 1,098 and 600 genes as candidate targets of GRF1 and GRF3, respectively.

GRFs in *Arabidopsis* function redundantly in controlling various aspects of plant development (Kim et al., 2003; Kim and Kende, 2004; Horiguchi et al., 2005; Kim and lee, 2006). To address the potential redundant function of GRF1 and GRF3 in regulating gene expression, we compared the 1,098 candidate target genes of GRF1 with the 600 candidate target genes of GRF3 to identify genes that are common to both. Interestingly, we discovered 264 genes as overlapping targets between GRF1 and GRF3 reducing the total number of targets to 1,434 unique putative target genes of GRF1 and GRF3. Interestingly, the 264 overlapping target genes all showed the same trend of expression in the rGRF1 and rGRF3 overexpression lines, in which 124 genes were up regulated and 140 genes were down regulated in both lines, indicating that GRF1 and GRF3 activate and inhibit gene expression in a similar manner.

In addition to apparently targeting identical genes, careful examination of the putative function/annotation of the GRF1 and GRF3 target genes revealed that both transcription factors regulate genes with similar function or different members belonging to the same gene family. When classifying candidate target genes into different groups by molecular function using the gene ontology categorization from The *Arabidopsis* Information Resource world wide web at *Arabidopsis*.org, we discovered a high proportion of genes associated with other enzyme activity, binding activity, transferase activity, hydrolase activity, and transcription factor activity (FIG. 6D) for both GRF1 and GRF3. When these genes were grouped by associated biological processes, the most abundant groups corresponded to metabolism and other cellular processes while response to stress, response to abiotic or biotic stimuli, and protein metabolism also represented significant groups (FIG. 6E). These data provide strong evidence for the functional overlap between GRF1 and GRF3 in the regulation of gene expression both during normal development and in response to nematode infection. Furthermore, these data provide valuable insight into the molecular functions of GRF1 and GRF3 as transcriptional regulators.

A Master Switch for Gene Expression in the Syncytium

If in fact the candidate GRF1 and GRF3 target genes are regulated by these transcription factors and have a role in mediating syncytium induction/formation, these genes should exhibit differential regulation in the syncytium when compared with other root tissues because we have documented differential regulation of GRF1 and GRF3 in the syncytium. Therefore, we next compared the candidate targets of GRF1 and GRF3 with the 7,225 genes differentially expressed in *Arabidopsis* syncytia reported by Szakasits et al. (2009). Intriguingly, out of the 1,098 genes identified as potential targets of GRF1, we found 610 genes (55.6%, $\chi^2$=289.91, p-value=5.19E-65) that are differentially expressed in the syncytium. Also, out of the 600 genes identified as candidate targets of GRF3, we found 324 genes (54%, $\chi^2$=134.45, p-value=4.35E-31) that are differentially expressed in the syncytium. In cumulo, when comparing the 1,434 unigenes of GRF1/GRF3 candidate target genes, we found that 796 (55.5%, $\chi^2$=383.49, p-value=2.16E-85) are differentially expressed in the syncytium. These data provide strong support for the validity of these genes as candidate target genes of GRF1 and GRF3.

More interestingly, analyses of our microarray comparisons were also extended to determine the percentage of the 7,225 syncytium-regulated genes (Szakasits et al., 2009) that could be explained by the GRF modulations performed by us, i.e., by comparing all genes identified as differentially expressed in the rGRF1-overexpressing (2,293 genes) and rGRF3-overexpressing (2,410 genes) plants as well as in the grf1/grf2/grf3 mutant (3,944 genes), i.e., not just the putative target genes. We found 1,131 (49.32%, $\chi^2$=346.13, p-value=2.95E-77) and 1,165 (48.34%, $\chi^2$=325.27, p-value=1.03E-72) genes as overlapping between the 7,224 syncytium-regulated genes and those of rGRF1 and rGRF3, respectively (FIG. 6F). After eliminating duplicates between both cohorts, the resultant 1,965 unique genes were found to account for 27.2% ($\chi^2$=605.47, p-value=1.08E-133) of the total number of syncytium-regulated genes (FIG. 6F). Furthermore, 2,073 genes overlapped between syncytium-regulated genes and those found to be differentially regulated in the grf1/grf2/grf3 triple mutant (FIG. 6F), which means that 28.7% ($\chi^2$=916.26, p-value=2.87E-201) of the total number of syncytium-regulated genes change expression in the triple mutant. The 1,965 unique syncytial genes identified in rGRF1 and rGRF3 overexpression lines along with the 2,073 syncytial genes identified in the triple mutant make up a unigene set of 3,160 syncytial genes (FIG. 6F). This number represents an astonishing 44% ($\chi^2$=1234.13, p-value=2.33E-270) of all syncytial genes reported by Szakasits et al. (2009). In other words, the modulations of GRFs performed by us account for almost half of the reported syncytial gene expression changes in *Arabidopsis*. GRFs, thus, play tremendously important roles in syncytium induction/formation. Considering that GRF1 and GRF3 change expression in the syncytium as a function of miRNA396, as we have shown above, this miRNA, thus, represents a bona fide master switch of syncytial gene expression changes.

DISCUSSION

Formation of functional syncytia requires a tightly fine-tuned coordination of multiple developmental and cellular processes to achieve the redifferentiation of hundreds of fused root cells into a functional new organ. The mechanisms and underlying regulatory networks that control the integration of these processes remain poorly understood. In this paper, we report on the biological role of miR396 in syncytium formation and function. In response to *H. schachtii*, miR396, GRF1 and GRF3 are regulated transcriptionally. miR396 and its target genes GRF1 and GRF3 showed opposite expression patterns in the early developing syncytium at the parasitic J2 and early J3 stages when miR396 was down regulated and GRF1 and GRF3 showed up regulation. At later stages, we established that up regulation of miR396 at 8 and 14 dpi is accompanied by a posttranscriptional down regulation of GRF1 and GRF3 (FIG. 3). miR396, therefore, has a stage-specific function in the spatial activation/restriction of GRF1 and GRF3 expression in the syncytium. The fact that miRNA396 up regulation and GRF modulations lead to smaller syncytia and reduced susceptibilities shows that the coordinated regulation of miR396 and GRF1 and GRF3 is required for correct cell fate specification and differentiation in the developing syncytium.

Recent studies have shown examples of miRNA expression being positively or negatively regulated by the transcription factors they target through negative or positive feedback loops (Gutierrez et al., 2009; Wu et al., 2009; Wang et al, 2009; Yant et al., 2010; Marin et al., 2010). Similarly, the miR396/GRF1 and GRF3 regulatory module is under a tightly fine-tuned regulation to ensure adequate expression of GRF1 and GRF3 and their negative regulator miR396. Our data suggest that maintenance of the homeostasis of miR396 and the target genes at specific threshold levels is critical for syncytium development. This suggestion is supported by our finding that down regulation of GRFs through overexpression of miR396a/b, or overexpression of wild-type or miR396-resistant versions of GRF1/GRF3 resulted in reduced nematode susceptibility.

Our results further show that the homeostasis between miR396 and the target genes GRF1 and GRF3 is established through a reciprocal feedback regulation, in which the expression of GRF1/GRF3 and miR396 negatively regulate each other's expression. The complexity of the miR396/ GRF regulatory module was further demonstrated by our data showing that constitutive expression of GRF1 or GRF3 lowers the mRNA abundance of other GRFs as well as their own endogenous transcripts. Cross-regulation among transcription factor gene family members targeted by miRNAs also has been reported by others (Gutierrez et al., 2009). It is most likely that GRF1 and GRF3 are part of a highly interconnected network of GRF transcription factors that fine tune downstream signaling pathways in the syncytium, and that disturbance of this interconnected network impacts normal differentiation and developmental processes in the syncytium.

We propose that during the early stage of syncytium development inactivation of miR396 activity in the syncytium increases GRF1 and GRF3 expression to a defined threshold that enables these transcription factors to regulate gene expression reprogramming events that direct the differentiation and formation of the nematode feeding site. Once the syncytium is established, miR396 expression is induced to high levels in the feeding site, which posttranscriptionally reduces the expression of GRF1 and GRF3, thereby ending the induction/formation phase of the syncytium and leading syncytial cells to enter the maintenance phase after the differentiation events have been completed. The opposite expression patterns of miR396 during syncytium initiation/formation and maintenance stages are similar to those of *Arabidopsis* miR156 and miR172 during the juvenile-to-adult phase transition where miR156 is expressed at high levels during shoot development and then decreases with time, while miR172 has an inverse expression pattern (Aukerman and Sakai, 2003; Jung et al., 2007; Wu and Poethig, 2006).

The Role of GRF1 and GRF3 in Mediating Gene Expression in the Syncytium

Despite ongoing efforts to identify the biological processes regulated by GRFs during plant development, only a very limited number of target genes has been identified and characterized to date (Kim and Kende, 2004), thus our microarray study addresses an important need. We retained only genes showing opposite expression between grf1/grf2/grf3 triple mutant and rGRF1 or rGRF3 in order to identify the most likely target gene candidates that are directly or indirectly regulated by GRF1 or GRF3. Among these target candidates, genes coding for transcription factors or proteins with binding activity represent 39% and 35% of the putative GRF1 or GRF3 target genes, respectively (FIG. 6D), which documents a continuous amplification of the GRF response by targeting regulatory genes. I.e., the enrichment of transcription factors belonging to zinc finger, Myb, WRKY, bHLH, AP2 domain-containing, CCAAT-binding, or NAC domain transcription factor families among the GRF1 or GRF3 target genes represents a powerful mechanism to trigger a massive signaling response to GRF1 or GRF3 expression. As a point in case, syncytium formation has to be associated with a modulation of host defense responses (Davis et al., 2004; Gheysen and Fenoll 2002; Williamson and Kumar 2006) and we found a number of genes involved in different aspects of plant defenses among the putative targets of GRF1 or GRF3. Similarly, plant hormones, including auxin, have been implicated in syncytium development (Grunewald et al., 2009), and GRF1 or GRF3 appear to regulate a set of genes involved in hormone biosynthesis or signaling pathways of auxin, brassinosteroids, cytokinins, ethylene, gibberellins, and jasmonates. Furthermore, cell wall modifications are obvious mechanisms of syncytium formation and a high proportion of genes with cell wall related functions also are enriched among the putative GRF target genes. In other words, GRF1 and GRF3 likely are impacting a very wide spectrum of physiological processes associated with syncytium formation. This assessment becomes even more concrete when considering our finding that almost half of the putative GRF1 and GRF3 target genes were previously identified as changing expression in the syncytium (Szakasits et al., 2009). This phenomenon provides the mechanistic basis for GRF1 and GRF3 to directly influence a variety of signaling and developmental pathways required to govern the redifferentiation of nematode-parasitized root cells into a functional new organ. While it is fascinating to consider that half of the putative GRF1 and GRF3 targets are involved in syncytial functions, as we would have surmised from the syncytium-specific GRF expression characteristics uncovered in this paper, the truly fascinating discovery is made when performing this analysis in the opposite direction. Not only are more than 55% of the GRF target genes implicated in syncytium events, more importantly, the expression of 44% of the 7,225 genes reported by Szkasits et al. (2009) to change expression in the *Arabidopsis* syncytium, is altered by GRF1 and GRF3 and, thus, by miRNA396. Consequently, almost half of the known syncytial gene expression events in *Arabidopsis* can be modulated by miRNA396 as a single molecular master switch. No other known mechanism is able to exert the same powerful control over syncytial events.

EXPERIMENTAL PROCEDURES

Plant Materials and Growth Conditions

*Arabidopsis thaliana* Wild type Columbia-0 (Col-0) was used in all experiments except for the grf1/grf2/grf3 triple knockout mutant, which is in the Wassilewskija (Ws) background (Kim et al., 2003). Plants were grown in long days (16 h light/8 h dark) at 23° C.

Plasmid Construction and Generation of Transgenic *Arabidopsis* Plants

Procedures for plasmid construction and primer sequences used for PCR amplification are provided in Supplemental Experimental Procedures.

Identification of T-DNA Mutants of GRF1 and GRF3

Two independent T-DNA insertional alleles of GRF1 (Salk_069339C and Salk_078547C) or GRF3 (Salk_026786 and Salk_116709) in the Col-0 background were obtained from the Salk T-DNA insertional mutant collection (Alonso et al., 2003).

Histochemical Analysis of GUS Activities

The histochemical staining of GUS enzyme activity was performed according to Jefferson et al. (1987). Tissue samples were viewed using a Zeiss SV-11 microscope and the images were captured using a Zeiss AxioCam MRc5 digital camera and then processed using Zeiss Axiovision software (release 4.8).

Nematode Infection Assay

Ten-day-old seedlings were inoculated with approximately 200 surface-sterilized J2 *H. schachtii* nematodes per plant (see Supplemental Experimental Procedures for details).

Nematode Development Assay

Plants were grown on modified Knop's medium in 12-well culture plates. At 10 days, each plant was inoculated with 200 surface-sterilized J2 of *H. schachtii*, and plants were assessed at 5 and 21 days post infection for parasitic-stage juveniles and females, respectively. Average numbers of developing nematodes were calculated for each time point, and statistically significant differences were determined in a modified test using the statistical software package SAS.

Root Length Measurements

*Arabidopsis* plants were grown vertically on modified Knop's medium for ten days and then the root length of at least 30 plants per line was measured as the distance between the crown and the tip of the main root in three independent experiments. Statistically significant differences between lines were determined by unadjusted paired t test ($P<0.01$).

Syncytial Measurements

*Arabidopsis* seeds were planted on modified Knop's medium and 10-day-old seedlings were inoculated with ~200 surface-sterilized J2 *H. schachtii*. For each line, at least 20 single-female syncytia were randomly selected, photographed and measured as previously described by Hewezi et al. (2008b).

RNA Isolation and qPCR

Total RNA was extracted from root tissues using the TRIzol reagent (Invitrogen, Carlsbad, Calif., U.S.A.) following the manufacturer's instructions. DNase treatment of total RNA was carried out using Deoxyribonuclease I (Invitrogen). The treated total RNA (5 µg) was polyadenylated and reverse transcribed using "Mir-X miRNA First-Strand Synthesis Kit" (Clontech, Mountain View, Calif., USA)

following the manufacturer's instructions. The synthesized cDNAs then were diluted to a concentration equivalent to 10 ng total RNA/µL and used as a template in real-time RT-PCR reactions to quantify both miRNA and GRF expression levels using the two-step RT-PCR kit (Bio-Rad) according to the manufacturer's protocol. PCR conditions and primer sequences are provided in the Supplemental Experimental Procedures.

Microarray Analysis

Arabidopsis plants were grown vertically on modified Knop's medium for 2 weeks and then root tissues were collected for RNA extraction. Affymetrix Arabidopsis gene chips (ATH1) were used to compare the gene expression in the wild type to gene expression in the triple mutant and the rGRF1 or rGRF3 plants. Probe preparation was performed as described in the GeneChip® 3' IVT Express Kit (Affymetrix, part number 901229) technical manual. Hybridization and washes were performed as described by Affymetrix in the GeneChip facility at Iowa State University. Statistical analyses of gene expression levels are detailed in the Supplemental Experimental Procedures. Testing for the significance of gene list overlaps was determined using Chi-square tests. See Supplemental Experimental Procedures for details.

Accession Numbers

Sequence data from this article can be found in the Arabidopsis Genome Initiative or GenBank/EMBL databases under the following accession numbers:
miR396a (AT2G10606)(SEQ ID NO:1),
miR396b (AT5G35407))(SEQ ID NO:2),
GRF1 (At2g22840) (SEQ ID NO:3),
GRF2 (At4g37740))(SEQ ID NO:4),
GRF3 (At2g36400))(SEQ ID NO:5),
GRF4 (At3g52910))(SEQ ID NO:6),
GRF5 (At3g13960))(SEQ ID NO:7),
GRF6 (At2g06200))(SEQ ID NO:8),
GRF7 (At5g53660)(SEQ ID NO:9),
GRF8 (At4g24150)(SEQ ID NO:10),
GRF9 (At2g45480))(SEQ ID NO:11),
and Actin8 (AT1G49240),

REFERENCES

Alkharouf, N. W., Klink, V. P., Chouikha, I. B., Beard, H. S., MacDonald, M. H., Meyer, S., Knap, H. T., Khan, R., and Matthews, B. F. (2006). Time course microarray analyses reveal global changes in gene expression of susceptible Glycine max (soybean) roots during infection by Heterodera glycines (soybean cyst nematode). Planta 224, 838-852.

Alonso, J. M., et al. (2003). Genome-wide insertional mutagenesis of Arabidopsis thaliana. Science 301, 653-657.

Aukerman, M. J., and Sakai, H. (2003). Regulation of flowering time and floral organ identity by a microRNA and its APETALA2-like target genes, Plant Cell 15, 2730-2741

Chen, X. (2009). Small RNAs and their roles in plant development. Annu. Rev. Cell Dev. Biol. 25, 21-44.

Davis, E. L., Hussey, R. S., and Baum, T. J. (2004). Getting to the roots of parasitism by nematodes. Trends Parasitol. 20, 134-141

Fahlgren, N., Howell, M. D., Kasschau, K. D., Chapman, E. J., Sullivan, C. M., Cumbie, J. S., Givan, S. A., Law, T. F., Grant, S. R., Dangl, J. L., and Carrington, J. C. (2007). High-throughput sequencing of Arabidopsis microRNAs: Evidence for frequent birth and death of MIRNA genes. PLoS ONE 14, e219.

Gheysen, G. and Fenoll, C. (2002). Gene expression in nematode feeding sites. Annu. Rev. Phytopathol. 40, 191-219.

Grunewald, W., van Noorden, G., Van Isterdael, G., Beeckman, T., Gheysen, G., and Mathesius, U. (2009). Manipulation of auxin transport in plant roots during Rhizobium symbiosis and nematode parasitism. Plant Cell 21, 2553-2562.

Gutierrez, L., Bussell, J. D., Pacurar, D. I., Schwambach, J., Pacurar, M., and Bellini, C. (2009). Phenotypic plasticity of adventitious rooting in Arabidopsis is controlled by complex regulation of AUXIN RESPONSE FACTOR transcripts and microRNA abundance. Plant Cell 21, 3119-3132.

He, X. F., Fanga, Y. Y., Fenga, L., and Guoa, H. S. (2008). Characterization of conserved and novel microRNAs and their targets, including a TuMV-induced TIR-NBS-LRR class R gene-derived novel miRNA in Brassica. FEBS Lett. 582, 2445-2452.

Hewezi, T., Howe, P., Maier, T. R., and Baum, T. J. (2008a). Arabidopsis small RNAs and their targets during cyst nematode parasitism. Mol. Plant Microbe Interact. 21, 1622-1634.

Hewezi, T., Howe, P., Maier, T. R., Hussey, R. S., Mitchum, M. G., Davis, E. L., and Baum, T. J. (2008b). Cellulose binding protein from the parasitic nematode Heterodera schachtii interacts with Arabidopsis pectin methylesterase: cooperative cell wall modification during parasitism. Plant Cell 20, 3080-3093.

Horiguchi, G., Kim, G. T., and Tsukaya, H. (2005). The transcription factor AtGRF5 and the transcription coactivator AN3 regulate cell proliferation in leaf primordia of Arabidopsis thaliana. Plant J. 43, 68-78.

Ithal, N., Recknor, J., Nettleton, D., Maier, T., Baum, T. J., and Melissa, M. G. (2007). Developmental transcript profiling of cyst nematode feeding cells in soybean roots. Mol. Plant Microbe Interact. 20, 510-525.

Jefferson, R. A., Kavanagh, T. A., and Bevan, M. W. (1987). GUS fusions: β-glucuronidase as a sensitive and versatile gene fusion marker in higher plants. EMBO J. 6, 3901-3907.

Jones-Rhoades, M. W., and Bartel, D. P. (2004). Computational identification of plant microRNAs and their targets, including a stress-induced miRNA. Mol. Cell 14, 787-799.

Jung, J. H., Seo, Y. H., Seo, P. J., Reyes, J. L., Yun, J., Chua, N. H., and Park, C. M. (2007). The GIGANTEA-regulated microRNA172 mediates photoperiodic flowering independent of CONSTANS in Arabidopsis, Plant Cell, 19, 2736-2748.

Katiyar-Agarwal, S., Gao, S., Vivian-Smith, A., and Jin, H. L. (2007). A novel class of bacteria-induced small RNAs in Arabidopsis. Genes Dev. 21, 3123-3134.

Katiyar-Agarwal, S., Morgan, R., Dahlbeck, D., Borsani, O., Jr, A. V., Zhu, J. K., Staskawicz, B. J., and Jin, H. L. (2006). A pathogen-inducible endogenous siRNA in plant immunity. Proc. Natl. Acad. Sci. USA 103, 18002-18007.

Kim, J. H., Choi, D., and Kende, H. (2003). The AtGRF family of putative transcription factors is involved in leaf and cotyledon growth in Arabidopsis. Plant J. 36, 94-104.

Kim, J. H., and Kende, H. (2004). A transcriptional coactivator, AtGIF1, is involved in regulating leaf growth and morphology in Arabidopsis. Proc. Natl. Acad. Sci. USA 101, 13374-13379.

Kim, J. H., and Lee, B. H. (2006). GROWTH-REGULATING FACTOR4 of Arabidopsis thaliana is required for development of leaves, cotyledons, and shoot apical meristem. J. Plant Biol. 49, 463-468.

Klink, V. P., Hosseini, P., Matsye, P., Alkharouf, N. W., and Matthews, B. F. (2009). A gene expression analysis of syncytia laser microdissected from the roots of the *Glycine max* (soybean) genotype PI 548402 (Peking) undergoing a resistant reaction after infection by *Heterodera glycines* (soybean cyst nematode). Plant Mol. Biol. 71, 525-567.

Li, Y., Zhang, Q., Zhang, J., Wu, L., Qi, Y., and Zhou, J-M. (2010). Identification of MicroRNAs Involved in Pathogen-Associated Molecular Pattern-Triggered Plant Innate Immunity. Plant Physiol. 152, 2222-2231.

Liu, D., Song, Y., Chen, Z., and Yu, D. (2009). Ectopic expression of miR396 suppresses GRF target gene expression and alters leaf growth in *Arabidopsis*. Physiol. Plant 136, 223-236.

Lu, S., Sun, Y-H., Amerson, H., and Chiang, V. L. (2007). MicroRNAs in loblolly pine (*Pinus taeda* L.) and their association with fusiform rust gall development. Plant J. 51, 1077-1098.

Marin, E., Jouannet, V., Herz, A., Lokerse, A. S., Weijers, D., Vaucheret, H., Nussaume, L., Crespi, M. D., and Maizel, A. (2010). miR390, *Arabidopsis* TAS3 tasiRNAs, and their AUXIN RESPONSE FACTOR targets define an autoregulatory network quantitatively regulating lateral root growth. Plant Cell 22:1104-1117.

Navarro, L., Dunoyer, P., Jay, F., Arnold, B., Dharmasiri, N., Estelle, M., Voinnet, O., and Jones, J. D. G. (2006). A plant miRNA contributes to antibacterial resistance by repressing auxin signaling. Science 312, 436-439.

Navarro, L., Jay, F., Nomura, K., He, S. Y., and Voinnet, O. (2008). Suppression of the microRNA pathway by bacterial effector proteins. Science 321, 964-967.

Pandey, S. P., Shahi, P., Gase, K., and Baldwin, I. T. (2008). Herbivory-induced changes in the small-RNA transcriptome and phytohormone signaling in *Nicotiana attenuata*. Proc. Natl. Acad. Sci. USA 105, 4559-4564.

Rodriguez, R. E., Mecchia, M. A., Debernardi, J. M., Schommer, C., Weigel D., and Palatnik, J. F. (2010). Control of cell proliferation in *Arabidopsis thaliana* by microRNA miR396. Development 137, 103-112.

Szakasits, D., Heinen, P., Wieczorek, K., Hofmann, J., Wagner, F., Kreil, D. P., Sykacek, P., Grundler, F. M., and Bohlmann, H. (2009). The transcriptome of syncytia induced by the cyst nematode *Heterodera schachtii* in *Arabidopsis* roots. Plant J. 57, 771-784.

Wang, J. W., Czech, B., and Weigel, D. (2009). miR156-regulated SPL transcription factors define an endogenous flowering pathway in *Arabidopsis thaliana*. Cell 138, 738-749.

Williamson, V. M., and Kumar, A. (2006). Nematode resistance in plants: the battle underground, Trends Genet. 22, 396-403.

Wu, G., and Poethig, R. S. (2006). Temporal regulation of shoot development in *Arabidopsis thaliana* by miR156 and its target SPL3. Development, 133, 3539-3547.

Wu, G., Park, M. Y., Conway, S. R., Wang, J. W., Weigel, D., and Poethig, R. S. (2009). The sequential action of miR156 and miR172 regulates developmental timing in *Arabidopsis*. Cell 138, 750-759.

Yant, L., Mathieu, J., Dinh, T. T., Ott, F., Lanz, C., Wollmann, H., Chen, X., and Schmid, M. (2010). Orchestration of the floral transition and floral development in *Arabidopsis* by the bifunctional transcription factor APETALA2. Plant Cell 22, 2156-2170.

| Construct or Gene | Name | | Primer Sequence 5'-3' |
|---|---|---|---|
| Primer sequences for overexpression and promoter constructs | | | |
| Overexpression miR396a | miR396a-BamHI F (SEQ ID NO: 29) | | TATAGGATCCTAGGGTTTCGTCTGCTCTACATGACCC |
| | miR396a-SacI R (SEQ ID NO: 30) | | ATGATGAGCTCCGAAATTTAGAAAATCATTTGACTCT |
| overexpression miR396b | miR396b-BamHI F (SEQ ID NO: 31) | | TATAGGATCCTCAGAAGAAGGAGAAGATGAAGATCC |
| | miR396b-SacI R (SEQ ID NO: 32) | | ATGATGAGCTCGTGAATCAATGGAGTAAAACCCTGAAT |
| Overexpression wtGRF1 | GRF1-XbaI F1 (SEQ ID NO: 33) | | TATATCTAGAATGGATCTTGGAGTTCGTGTTTCTGG |
| | GRF1-SacI R2 (SEQ ID NO: 34) | | ATGATGAGCTCTCACAGAGAAGGAGCAGTAGCAGAAG |
| Overexpression rGRF1 | GRF1 F2 (SEQ ID NO: 35) | | GAGGCCGCCATAGAAGCAGGAAACCGGTAGAGGGCCAAAATG |
| | GRF1 R1 (SEQ ID NO: 36) | | CATTTTGGCCCTCTACCGGTTTCCTGCTTCTATGGCGGCCTC |
| Overexpression wtGRF3 | GRF3-XbaI F1 (SEQ ID NO: 37) | | TATATCTAGAATGGATTTGCAACTGAAACAATGGAG |
| | GRF3-SalI R2 (SEQ ID NO: 38) | | ATGATGTCGACTCAATGAAAGGCTTGTGTCAGACAC |
| Overexpression rGRF3 | GRF3 F2 (SEQ ID NO: 39) | | GTGGCCGCAACAGGAGCCGTAAACCGGTCGAGACTCCAACCA |
| | GRF3 R1 (SEQ ID NO: 40) | | TGGTTGGAGTCTCGACCGGTTTACGGCTCCTGTTGCGGCCAC |
| Promoter miR396a:GUS | pmiR396a-XbaI F (SEQ ID NO: 41) | | TATATCTAGACTTGATTGTTTATTTTATCGTTTTGTG |
| | pmiR396a-BamHI R (SEQ ID NO: 42) | | ATGATGGATCCAGGGTCATGTAGAGCAGACGAAACCCTA |
| Promoter miR396b:GUS | pmiR396b-XbaI F (SEQ ID NO: 43) | | TATATCTAGAACCGCAACTTTCTGTTATGATATTGATGG |
| | pmiR396b-BamHI R (SEQ ID NO: 44) | | ATGATGGATCCAGGATCTTCATCTTCTCCTTCTTCTGAAA |
| Promoter GRF1:GUS | pGRF1-HindIII F (SEQ ID NO: 45) | | TATAAAGCTTTGTTAATTTTATCAAATGTATATTCTT |
| | pGRF1-SalI R (SEQ ID NO: 46) | | ATCATGTCGACAAAAAATGGATTCAGAAGGAGACAAAG |
| Promoter GRF3:GUS | pGRF3-SalI F (SEQ ID NO: 47) | | TATAGTCGACGCTGAGACTCTGTGGAAGCCGTTCGC |
| | pGRF3-BamHI R (SEQ ID NO: 48) | | ATGATGGATCCTGAAGAAAGAGAGAGAAGTGTTGG |
| Gene-specific primer sequences used for qPCR | | | |
| Pri-miR396a | Pri-miR396a F (SEQ ID NO: 49) | | CAGCTTTCTTGAACTGCAAAAC |
| Pri-miR396b | Pri-miR396b F (SEQ ID NO: 50) | | GGTCATACTTTTCCACAGCTTTC |

-continued

| Construct or Gene Name | | Primer Sequence 5'-3' |
|---|---|---|
| Mature miR396 | Mature miR396 F (SEQ ID NO: 51) | TTCCACAGCTTTCTTGAACTGAA |
| wtGRF1 | wtGRF1 F (SEQ ID NO: 52) | TCGTTCAAGAAAGCCTGTGGAAGG |
| | wtGRF1 R (SEQ ID NO: 53) | GTTCCAACAGCAGCGGCAAGGC |
| rGRF1 | rGRF1 F (SEQ ID NO: 54) | AGAAGCAGGAAACCGGTAGAGGG |
| GRF2 | GRF2 F (SEQ ID NO: 55) | CCCGAATACCGCAAAGACCT |
| | GRF2 R (SEQ ID NO: 56) | GTTGTGTGTGGAGGAAGGGGA |
| wtGRF3 | wtGRF3 F (SEQ ID NO: 57) | CCGTTCAAGAAAGCCTGTGGAAAC |
| | wtGRF3 R (SEQ ID NO: 58) | TCCTCCTTGACCAACCACTTCCT |
| rGRF3 | rGRF3 F (SEQ ID NO: 59) | CAGGAGCCGTAAACCGGTCGAG |
| GRF4 | GRF4 F (SEQ ID NO: 60) | ACCGCCACAACCACCATCACA |
| | GRF4 R (SEQ ID NO: 61) | TCCATTGCTGAATCCACTGTTAGCT |
| GRF5 | GRF5 F (SEQ ID NO: 62) | TGGAGGAGTTGGGGAGAGAACG |
| | GRF5 R (SEQ ID NO: 63) | GTTGAACATGTCGGCGCCCAA |
| GRF6 | GRF6 F (SEQ ID NO: 64) | CGAGGAGAAGCAGCCGGATCGAC |
| | GRF6 R (SEQ ID NO: 65) | CCTCTTGCTTCCTTGCTCTTCTTC |
| GRF7 | GRF7 F (SEQ ID NO: 66) | GGGCCAAGACGAAATGGGCCT |
| | GRF7 R (SEQ ID NO: 67) | CCGCTAATGGTCCACCAGGTG |
| GRF8 | GRF8 F (SEQ ID NO: 68) | GGCTGGAGGAGGCATGGAGG |
| | GRF8 R (SEQ ID NO: 69) | GGAGACACCGAGACACAGTGC |
| GRF9 | GRF9 F (SEQ ID NO: 70) | CGGCACATGCATAGAGGTCGT |
| | GRF9 R (SEQ ID NO: 71) | CAGGATCTGGCACTAGGCAGTG |
| Actin8, | Actin8 F (SEQ ID NO: 72) | AGTGGTCGTACAACCGGTATTGT |
| | Actin8 R (SEQ ID NO: 73) | GAGGATAGCATGTGGAACTGAGAA |

Example 2 miR396 in Soybean During Cyst Nematode Infection

In order to understand the role that miR396 plays during soybean infection by the soybean cyst nematode (*Heterodera glycines*; SCN), expression analyses were performed on primary and mature sequences for all miR396 paralogs (miR396a, miR396b, miR396c and miR396e) and seven of its predicted target Growth Regulating Transcription Factors (GRF8, GRF9, GRF12, GRF13, GRF15, GRF16 and GRF19) using quantitative real-time PCR (qRT-PCR). Soybean seedlings were infected with SCN three days after germination and RNA was extracted 2, 4, 8 and 14 days post inoculation (dpi). RNA from both SCN infected and mock inoculated soybean seedlings was reverse-transcribed into cDNA for qRT-PCR.

Data were analyzed using the comparative Ct method with U6 snRNA as the reference gene for microRNA quantification and ubiquitin for GRFs. Significance tests were performed using the Student's t-test (p-value<0.05) and significant values are indicated on the graph with asterisks. Error bars represent the standard error. Three to four biological replicates were used for each sequence at each time point as well as three technical replicates during qRT-PCR.

In summary, steady-state RNA levels for miR396 and its target genes in soybean during SCN infection very closely resembled the observations made in *Arabidopsis*: an early downregulation of mature miR396 with a simultaneous increase in GRF mRNA at the time of syncytium formation. At later time points, likely coinciding with the end of syncytium formation, abundance of mature miR396 increases and GRF target gene expression is turned off. Consequently, there is a high probability that the manipulations we performed in *Arabidopsis* and that resulted in decreased plant susceptibility will have similar effects on susceptibility of soybean to SCN. Results are shown in FIG. 12.

Sequence Information

Some sequences have not yet been submitted to NCBI and thus do not have accession numbers; locus IDs obtained from Soybase.
gma-precursor-miR396a
Accession #: MI0001785 (SEQ ID NO:12)
gma-mature-miR396a
Accession #: MIMAT0001687 (SEQ ID NO:13)
gma-precursor-miR396b
Accession #: MI0001786 (SEQ ID NO:14)
gma-mature-miR396b
Accession #: MIMAT0001688 (SEQ ID NO:15)
gma-precursor-miR396c
Accession #: MI0010572 (SEQ ID NO:16)
gma-mature-miR396c
Accession #: MIMAT0010079 (SEQ ID NO:17)
gma-precursor-miR396e (SEQ ID NO:18)
Accession #: MI0016586
gma-mature-miR396e
Accession #: MIMAT0018345 (SEQ ID NO:19)
GmGRF8
Accession #: n/a
Locus ID: Glyma10g07790 (SEQ ID NO:20)
GmGRF9
Accession #: XM_003537618 (SEQ ID NO:21)
GmGRF12

Accession #: n/a
Locus ID: Glyma13g16920 (SEQ ID NO:22)
GmGRF13
Accession #: n/a
Locus ID: Glyma13g21630 (SEQ ID NO:23)
GmGRF15
Accession #: XM_003547454 (SEQ ID NO:24)
GmGRF16
Accession #: n/a
Locus ID: Glyma16g00970 (SEQ ID NO:25)
GmGRF19
Accession #: XM_003553541 (SEQ ID NO:26)

Other Sequences

Sequences for soybean miRNA396 may be found at miRBase dot org at world wide web including accession numbers MIMAT0020922 (gma-miR3961-3p), MIMAT0001688 (gma-miR396B-5p), MIMAT0020923 (gma-miR396b-3p). MIMAT0010079 (gma-miR396c), MIMAT0018262 (gma-miR396d). Other miR396 sequences available from different plant species include but are not limited to:

"miR396a"

| Accession | ID |
| --- | --- |
| MI0001013 | ath-MIR396a |
| MI0001046 | osa-MIR396a |
| MI0001539 | sbi-MIR396a |
| MI0001785 | gma-MIR396a |
| MI0001801 | zma-MIR396a |
| MI0002325 | ptc-MIR396a |
| MI0005621 | mtr-MIR396a |
| MI0005650 | ghr-MIR396a |
| MI0005773 | bna-MIR396a |
| MI0006569 | vvi-MIR396a |
| MI0012094 | aqc-MIR396a |
| MI0014581 | aly-MIR396a |
| MI0016122 | pab-MIR396a |
| MI0016706 | csi-MIR396a |
| MI0016983 | bgy-MIR396a |
| MI0016987 | bcy-MIR396a |
| MI0017511 | tcc-MIR396a |
| MI0018111 | bdi-MIR396a |
| MIMAT0001687 | gma-MIR396a-5p |

"miR396b"

| Accession | ID |
| --- | --- |
| MI0001014 | ath-MIR396b |
| MI0001047 | osa-MIR396b |
| MI0001538 | sbi-MIR396b |
| MI0001786 | gma-MIR396b |
| MI0001800 | zma-MIR396b |
| MI0002326 | ptc-MIR396b |
| MI0005622 | mtr-MIR396b |
| MI0005651 | ghr-MIR396b |
| MI0006570 | vvi-MIR396b |
| MI0012095 | aqc-MIR396b |
| MI10014582 | aly-MIR396b |
| MI0016123 | pab-MIR396b |
| MI0016707 | csi-MIR396b |
| MI0016984 | bgy-MIR396b |
| MI0016988 | bcy-MIR396b |
| MI0017512 | tcc-MIR396b |
| MI10018125 | bdi-MIR396b |
| MIMAT0001688 | gma-MIR396b-5p |

"miR396c"

| Accession | ID |
| --- | --- |
| MI0001048 | osa-MIR396c |
| MI0001540 | sbi-MIR396c |
| MI0002327 | ptc-MIR396c |
| MI0007955 | vvi-MIR396c |
| MI0010569 | zma-MIR396c |
| MI0010572 | gma-MIR396c |
| MI0016124 | pab-MIR396c |
| MI0016735 | csi-MIR396c |
| MI0017513 | tcc-MIR396c |
| MI0018101 | bdi-MIR396c |

"miR396d"

| Accession | ID |
| --- | --- |
| MI0001702 | osa-MIR396d |
| MI0002328 | ptc-MIR396d |
| MI0006571 | vvi-MIR396d |
| MI0010570 | zma-MIR396d |
| MI0010897 | sbi-MIR396d |
| MI0016503 | gma-MIR396d |
| MI0017514 | tcc-MIR396c |
| MI0018096 | bdi-MIR396d |
| MI0001013 | ath-MIR396a |
| MI0001014 | ath-MIR396b |
| MI0001046 | Osa-MIR396a |
| MI0001047 | osa-MIR396b |
| MI0001048 | osa-MIR396c |

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention as described in the appended claims.

What is claimed is:

1. A method for improving nematode tolerance in plants comprising:
    expressing in a plant cell a heterologous promoter functional in said plant cell and operably linked to a recombinant polynucleotide sequence encoding a plant GRF protein with a miRNA396 binding site, wherein said plant GRF protein is selected from the group consisting of: GRF1 and GRF3;
    regenerating a transgenic plant from the plant cell; and
    selecting for a transgenic plant with improved nematode tolerance compared to a plant not expressing said recombinant polynucleotide.

2. The method of claim 1, wherein the plant cell is from a plant selected from the group consisting of: Potato, tomato, *Phaseolus* spp., sugarbeet, peas, *Vicia faba*, sugar cane, eggplant, peppers, tobacco, wheat, rice, sorghum, barley, oat, lawn grass, rye, soybean, canola, *Brassica*, sunflower, maize, sorghum, alfalfa, cotton, millet, peanut and cacao.

3. The method of claim 1 wherein said GRF is from *Arabidopsis*.

4. The method of claim 1 wherein said GRF is from *Glycine max*.

5. A plant made by the method of claim 1.

6. Seed of the plant of claim 5.

* * * * *

SEQUENCE LISTING

```
<160> NUMBER OF SEQ ID NOS: 28

<210> SEQ ID NO 1
<211> LENGTH: 151
<212> TYPE: DNA
<213> ORGANISM: Arabidopsis thaliana

<400> SEQUENCE: 1
ctctgtattc ttccacagct ttcttgaact gcaaaacttc ttcagatttt tttttttttc     60
ttttgatatc tcttacgcat aaaatagtga ttttcttcat atctctgctc gattgatttg    120
cggttcaata aagctgtggg aagatacaga c                                   151

<210> SEQ ID NO 2
<211> LENGTH: 135
<212> TYPE: DNA
<213> ORGANISM: Arabidopsis thaliana

<400> SEQUENCE: 2
ggtcatactt ttccacagct ttcttgaact ttcttttttca tttccattgt tttttttctta    60 aacaaaagta agaagaaaaa aaactttaag attaagcatt ttggaagctc aagaaagctg    120
tgggaaaaca tgaca                                                     135

<210> SEQ ID NO 3
<211> LENGTH: 1593
<212> TYPE: DNA
<213> ORGANISM: Arabidopsis thaliana

<400> SEQUENCE: 3
atggatcttg gagttcgtgt ttctggtcat gaaaccgttt cttctccggg tcaaactgaa     60
ctcggatctg gtttcagtaa caagcaagaa agatccggtt tcgatggtga agattgctgg    120
agaagttcaa agctctcacg aacatcaact gatggattct cttcttcccc tgcctctgct    180
aaaacgctgt cgtttcatca aggcatccct ttactgagat ctaccactat taatgatcct    240
cgtaaaggac aagaacacat gcttagcttc tcttctgctt caggcaaatc agatgtctca    300
ccttatcttc agtactgtag aaactcagga tatggtttag gaggaatgat gaacacaagc    360
aacatgcatg gaaacttgtt gacaggagta aaaggaccct tttcattgac tcagtgggca    420
gagctagagc aacaggcgtt gatctataag tatatcacag ccaatgtccc tgttccatct    480
agtttacttc tctctctcaa gaaatctttt ttcccttatg gttccttgcc tcctaattct    540
tttggatggg gctcttttca tctgggcttt tccggtggta acatggatcc cgagccaggg    600
agatgtcgcc ggacagatgg aaagaaatgg cggtgctcga gggacgctgt tcccgatcaa    660
aagtactgtg aacgacatat taacagaggc cgccatcgtt caagaaagcc tgtggaaggc    720
caaaatggcc acaatactaa tgctgccgcc gctgcttctg ctgctgccgc ttctaccgct    780
gctgctgtgt ccaaagcggc agcggggact tcagctgttg cgatgcgtgg atcagataat    840
aacaatagcc ttgccgctgc tgttggaaca caacatcata ccaataatca atctacagat    900
tctttggcta acagagttca aaattctcga ggggcttcgg ttttttcctgc cacgatgaac    960 ttacagtcga aggaaactca tccgaaacaa agcaataatc cctttgaatt cggactcatc   1020
tcttctgatt cgttacttaa tccgtcgcat aaacaagcct cgtatgcaac ctcttccaaa   1080
```

-continued

```
ggctttggat cgtatcttga cttcggcaac caagccaagc acgcgggaa tcacaacaat    1140 gtcgattctt ggcccgaaga gctgaaatcg gattggactc agctctcaat gtcaatccct    1200
atggctccat cttccctgt tcaagataaa cttgcactct caccttta ag gttatcgcgt    1260 gagtttgacc ccgcgatcca catgggatta ggcgtcaaca ccgagtttct tgaccccggg    1320
aaaaagacga taactggat accaatctcc tggggtaata caactccat gggaggtcca    1380 ctcggcgagg tactaaacag cacgaccaat agtcccaagt ttggttcctc tccaacaggc    1440
gtcttgcaaa agtcgacatt tggttctctt tctaacagca gctcggcaag cagcaccatc    1500
attggcgata caacaataa gaacggtgat ggaaaagatc cgcttggccc gaccacgctg    1560
atgaatactt ctgctactgc tccttctctg tga                                1593

<210> SEQ ID NO 4
<211> LENGTH: 1608
<212> TYPE: DNA
<213> ORGANISM: Arabidopsis thaliana

<400> SEQUENCE: 4
atggatattg gtgttcatgt tcttgggtcg gttactagta atgaaaatga gtcacttggt      60
ctaaaagagc ttataggaac taaacaagat agatccggat tcatcggtga ggattgcttg    120
caacgaagct tgaagctagc aagaacgaca actagagcgg aagaagaaga aaacttgtct    180
tcttctgttg cagctgctta ttgcaaaacg atgtcgtttc accaaggcat tcctctcatg    240
agatctgctt ctcctctttc ctctgattct cgccgtcaag aacaaatgct tagcttctca    300
gataaaccag acgctcttga tttcagtaaa tatgtcggtt tggataatag cagtaataac    360
aagaactctc tctcgccgtt tcttcaccag attcctccac cttcttactt tagaagctca    420
ggaggatatg gttctggtgg aatgatgatg aacatgagca tgcaagggaa cttcacaggt    480
gttaaaggac ttttacatt gactcaatgg gctgagttag agcaacaggc gttgatctat    540
aagtacatca cagccaatgt ccctgttcct tctagtttgc tcatctctat caagaagtct    600
tttatccctt acggatcttt gcctcctagt tccttcggat ggggaacttt ccatctcggt    660
ttcgcaggcg gtaacatgga ccctgagcca gggagatgcc gcagaacaga tgggaagaaa    720
tggcggtgct caagagacgc cgttcctgat cagaaatact gtgaaagaca catcaacaga    780
ggccgtcatc gttcaagaaa gcctgtgaa gtccaatctg ccaaaaccaa aaccgccgct    840
gctgcatcca aagcggttac tacaccacaa cagcctgttg tcgctggtaa tactaacaga    900
agcaatgccc gtgcatcaag caaccgcagc ctcgccattg aagtcaata tatcaatcct    960 tctacagaat ctttacctaa caacagagga gtttcgatat atccttccac cgtcaactta   1020
caacccaagg aatctccggt tattcatcag aaacacagaa acaacaacaa ccctttttgag  1080 tttggacaca tatcctctga ttcgttactc aacccgaata ccgcaaagac ctatggatca   1140
tcgttcttgg atttcagcag caaccaagag aagcattcag ggaatcacaa tcacaattct   1200
tggcctgaag agctgacatc agattggaca cagctctcaa tgtcaattcc aatagcatca   1260 tcatccccctt cctccacaca caacaacaac aatgctcaag aaaaaacaac actctcgcct   1320
ctcaggctat cccgcgagct tgacctatcg atccaaaccg atgaaacaac aatcgagcct   1380
actgtgaaaa aggtgaatac ttggatacca atctcatggg aaactccctt aggaggtcct   1440
ctaggtgaag tactaaacag tacaacgaat agtccaacat ttggatcttc tcctacaggg   1500
gttttgcaaa agtccacatt tgttcactc tctaacaaca gctccgtgag cagccccatt   1560
```

| gcagagaaca acagacacaa tggcgattac tttcattaca caacctga | 1608 |

<210> SEQ ID NO 5
<211> LENGTH: 1197
<212> TYPE: DNA
<213> ORGANISM: Arabidopsis thaliana

<400> SEQUENCE: 5

| atggatttgc aactgaaaca atggagaagc cagcagcagc aacaacatca gacagagtca | 60 |
| gaagaacaac cttctgcagc taagatacca aaacatgtct ttgaccagat tcattctcac | 120 |
| actgcaactt ctactgctct cctctctttt accctgagc ctacttcttc taaactctcc | 180 |
| tctttgtctc ctgattcttc ctccaggttc cccaagatgg ggagcttctt tagctgggca | 240 |
| cagtggcaag aacttgaact acaagctctg atctacaggt acatgttggc tggtgctgct | 300 |
| gttcctcagg agctcctttt accaatcaag aaaagccttc tccatctatc tccttcctac | 360 |
| tttcttcacc atcctcttca cacctacct cattaccaac ctgcttggta tttgggaagg | 420 |
| gcagcgatgg atcctgagcc aggcagatgc aggaaacgg atggtaagaa gtggagatgt | 480 |
| tcaagagacg tcttcgctgg ccacaagtat tgcgagcgcc acatgcaccg tggccgcaac | 540 |
| cgttcaagaa agcctgtgga aactccaacc accgtcaatg caactgccac gtccatggct | 600 |
| tcatcagtag cagccgcagc caccactaca acagcaacaa caacatctac gtttgctttt | 660 |
| ggtggtggtg gtgtagtga ggaagtggtt ggtcaaggag gatctttctt cttctctggc | 720 |
| tcttctaact cttcatctga acttctccac cttagtcaaa gttgttcgga gatgaagcaa | 780 |
| gaaagcaaca acatgaacaa caagaggcca tacgagtccc acatcggatt cagtaacaac | 840 |
| agatcagatg gaggacacat cctgaggccc ttctttgacg attggcctcg ttcttcgctc | 900 |
| caagaagctg acaatagttc aagccccatg agctcagcca cttgtctctc catctccatg | 960 |
| cccgggaact cttcctcaga cgtctctctg aagctgtcca caggcaacga gagggagcc | 1020 |
| cggagcaaca caatgggag agatcagcaa acatgagct ggtggagcgg tggaggttcc | 1080 |
| aaccaccatc atcacaacat gggcggacca ttggccgaag ccctgagatc ttcttcctca | 1140 |
| tcttccccaa ccagtgttct ccatcagctt ggtgtctcga cacaagcctt tcattga | 1197 |

<210> SEQ ID NO 6
<211> LENGTH: 1143
<212> TYPE: DNA
<213> ORGANISM: Arabidopsis thaliana

<400> SEQUENCE: 6

| atggacttgc aactgaaaca atggagaagt cagcagcaga atgagtcaga agaacaaggc | 60 |
| tctgctgcaa ctaagatatc aaacttttc tttgatcaga ttcagtccca aactgctact | 120 |
| tctgctgctg cggctcctct tcctctcttt gtccctgaac ccacttcttc ctcttctttc | 180 |
| tcttgcttct ctcctgactc ttctaattct tcttcttctt ccaggttcct caagatggga | 240 |
| aacttcttca gctgggcaca gtggcaagaa cttgagctac aagcactgat ctatagatac | 300 |
| atgttggctg gtgcttctgt tcctcaagag cttctcttac ctattaagaa aagtctcctc | 360 |
| catcaatctc ctatgcattt ccttcaccat cctcttcaac atagttttcc tcatcaccaa | 420 |
| ccttcttggt attggggaag aggagcaatg gatcctgagc cagggaggtg taagagaact | 480 |
| gacggcaaga aatggagatg ttcaagggat gttgtagcgg ccacaagta ttgtgaccgc | 540 |
| cacattcacc gtggaagaaa ccgttcaaga aagcctgtgg aaaccgccac aaccaccatc | 600 |
| acaacgacag ccacaacaac cgcatcttct tttgtcttag gtgaggagct tggtcatgga | 660 |

```
ccaaacaaca accacttctt ctcctctggt tcatctcaac ctctccacct tagtcatcaa    720
caaagttgtt cttcagagat gaaacaagaa agcaacaaca acaagaggcc atatgaagct    780
aacagtggat tcagcaatgg aagatcagac gatggtcaca tcttgaggca tttctttgac    840
gattggccac gatcatcaga ctctacctcc agtccaatga gctcatccac ttgtcatctt    900
tcaatctcca tgcccggtaa caacacgtcc tcagatgttt ctctaaaact ttccacaggc    960
aatgaagaag aagaagagaa catgagaaat aacaacaatg agagggagca atgaattgg    1020 tggagcaatg gagggaatca ccacaacaat atgggaggac cattagctga ggctttgagg   1080
tcagcttctt cgacgtcaag tgttcttcat cagatgggaa tctctactca agttttcat   1140 taa                                                                  1143
```

<210> SEQ ID NO 7
<211> LENGTH: 1194
<212> TYPE: DNA
<213> ORGANISM: Arabidopsis thaliana

<400> SEQUENCE: 7

```
atgatgagtc taagtggaag tagcgggaga acaataggaa ggcctccatt tacaccaaca     60
caatgggaag aactggaaca tcaagcccta atctacaagt catggtctc tggtgttcct    120 gtcccacctg agctcatctt ctccattaga agaagcttgg acacttcctt ggtctctaga    180
ctccttcctc accaatccct tggatggggg tgttaccaga tgggatttgg gagaaaacca    240
gatccagagc caggaagatg cagaagaaca gatggtaaga aatggagatg ctcaagagaa    300
gcttacccag attcgaagta ctgtgaaaaa cacatgcaca gaggaagaaa ccgtgccaga    360
aaatctcttg atcagaatca gacaacaaca actcctttaa catcaccatc tctctcattc    420
accaacaaca acaacccaag tcccaccttg tcttcttctt cttcctctaa ttcctcttct    480
actacttatt ctgcttcttc ttcttcaatg gatgcctaca gtaacagtaa taggtttggg    540
cttggtggaa gtagtagtaa cactagaggt tatttcaaca gccattctct tgattatcct    600
tatccttcta cttcacccaa acaacaacaa caaactcttc atcatgcttc cgctttgtca    660
cttcatcaaa atactaattc tacttctcag ttcaatgtct tagcctctgc tactgaccac    720
aaagacttca ggtactttca agggattggg gagagagttg gaggagttgg ggagagaacg    780
ttctttccag aagcatctag aagctttcaa gattctccat accatcatca ccaacaaccg    840
ttagcaacag tgatgaatga tccgtaccac cactgtagta ctgatcataa taagattgat    900
catcatcaca catactcatc ctcatcatca tctcaacatc ttcatcatga tcatgatcat    960
agacagcaac agtgttttgt tttgggcgcc gacatgttca acaaacctac aagaagtgtc   1020
cttgcaaact catcaagaca agatcaaaat caagaagaag atgagaaaga ttcatcagag   1080
tcgtccaaga agtctctaca tcacttcttt ggtgaggact gggcacagaa caagaacagt   1140
tcagattctt ggcttgacct ttcttcccac tcaagactcg acactggtag ctaa           1194
```

<210> SEQ ID NO 8
<211> LENGTH: 735
<212> TYPE: DNA
<213> ORGANISM: Arabidopsis thaliana

<400> SEQUENCE: 8

```
atggctacaa ggattccatt cacagaatca caatgggaag aacttgaaaa ccaagctctt     60
gtgttcaagt acttagctgc aaatatgcct gttccacctc atcttctctt cctcatcaaa    120
```

-continued

| | |
|---|---|
| agaccctttc tcttctcttc ttcttcttct tcatcttctt cttcaagctt cttctctccc | 180 |
| actctttctc cacactttgg gtggaatgtg tatgagatgg gaatgggaag aaagatagat | 240 |
| gcagagccag gaagatgtag aagaactgat ggcaagaaat ggagatgctc taaagaagct | 300 |
| taccctgact ctaagtactg tgagagacat atgcatagag gcaagaaccg ttcttcctca | 360 |
| agaaagcctc ctcctactca attcactcca aatctctttc tcgactcttc ttccagaaga | 420 |
| agaagaagtg gatacatgga tgatttcttc tccatagaac cttccgggtc aatcaaaagc | 480 |
| tgctctggct cagcaatgga agataatgat gatggctcat gtagaggcat caacaacgag | 540 |
| gagaagcagc cggatcgaca ttgcttcatc cttggtactg acttgaggac acgtgagagg | 600 |
| ccattgatgt tagaggagaa gctgaaacaa agagatcatg ataatgaaga gagcaagga | 660 |
| agcaagaggt tttataggtt tcttgatgaa tggccttctt ctaaatcttc tgtttctact | 720 |
| tcactcttca tttga | 735 |

<210> SEQ ID NO 9
<211> LENGTH: 1098
<212> TYPE: DNA
<213> ORGANISM: Arabidopsis thaliana

<400> SEQUENCE: 9

| | |
|---|---|
| atggactttc tcaaagtttc agacaagaca acaattccat atagaagtga ttctttgttt | 60 |
| agtttgaatc agcaacaata caaagagtct tcttttggat tcagagacat ggagattcat | 120 |
| ccgcatccta ctccatatgc aggaaatgga cttttgggtt gttattacta ttaccctttc | 180 |
| acaaacgcac aattgaagga gcttgagaga caagcaatga tctacaagta catgatcgca | 240 |
| tctattcctg ttcctttcga tctacttgtt tcttcaccat cctctgcctc tccttgtaac | 300 |
| aataaaaaca tcgccggaga tttagagccg ggaagatgcc ggagaacaga cggaaagaaa | 360 |
| tggagatgcg cgaaagaagt cgtctctaat cacaaatact gtgagaaaca cttacacaga | 420 |
| ggtcgtcctc gttcaagaaa gcatgtggaa cctccttatt ctcgccctaa caacaatggt | 480 |
| ggttctgtga aaacagaga tctcaaaaag cttcctcaaa agttatctag tagttccatc | 540 |
| aaagacaaaa cacttgagcc aatggaggtt tcatcatcaa tctcaaacta tagagactcc | 600 |
| agaggaagtg agaaatttac tgtattggca acaacagagc aagagaacaa gtatctgaat | 660 |
| ttcatagatg tatggtccga tggagtaaga tcatctgaaa aacagagtac aacttcaaca | 720 |
| cctgtttctt cttccaatgg caatctctct ctttactcgc ttgatctctc aatgggagga | 780 |
| aacaacttaa tgggccaaga cgaaatgggc ctgatacaaa tgggcttagg tgtaatcggg | 840 |
| tcgggtagtg aggatcatca cgggtatggt ccttatggtg tgacttcttc actagaggag | 900 |
| atgtcaagct ggcttgctcc gatgtctacc acacctggtg gaccattagc ggagatactg | 960 |
| aggccgagta cgaatttggc gatctctggt gatatcgaat cgtatagctt gatggagact | 1020 |
| cccactccaa gctcgtcccc gtctagagtg atgaagaaga tgactagttc agtgtccgac | 1080 |
| gaaagcagcc aggtttag | 1098 |

<210> SEQ ID NO 10
<211> LENGTH: 1482
<212> TYPE: DNA
<213> ORGANISM: Arabidopsis thaliana

<400> SEQUENCE: 10

| | |
|---|---|
| atgaggatgc ttcttgggat tccttacgta gacaagtcgg ttctttccaa ctctgttctt | 60 |
| gagagaggca agcaggataa aagcaaacta ttgttagtcg acaaatgcca ttatgagctt | 120 |

```
gatgttgaag aacgcaagga agattttgtt ggtgggtttg gatttggtgt tgtagaaaat        180
tcgcataaag acgttatggt gctacctcat catcactatt atccatcata ttcatcacct        240
tcctcttctt ctttgtgtta ctgttctgct ggtgttagcg atcccatgtt ctctgtttct        300
agcaatcagg cttacacttc ttctcacagt ggtatgttca cacccgccgg ttctggttct        360
gctgctgtga ctgtagcaga tccttttttc tccttgagct cttcagggga aatgagaaga        420
agtatgaacg aagatgctgg tgcagctttc agcgaagctc aatggcatga gcttgagagg        480
cagaggaata tatacaagta catgatggct tctgttcctg ttcctccaga gcttctcaca        540
cccttcccca agaaccacca atcaaacact aacccgatg tggatacata taggagtgga        600
atgtttagta tttatgctga ttacaagaat ctgccgttgt ctatgtggat gacagtaact        660
gtggcagtgg cgacaggagg ctcattgcag ctggggattg cttcaagcgc aagcaataac        720
acggctgatc tggagccatg gaggtgcaag agaacagatg ggaagaaatg gaggtgctct        780
agaaacgtga ttcctgatca gaaatactgt gagagacaca cacacaagag ccgtcctcgt        840
tcaagaaagc atgtggaatc atctccaccaa tcatctcacc acaatgacat tcgtacggct        900
aagaatgata ctagccagct tgtgagaact tatcctcagt tttacggaca acctataagc        960
cagatccctg tgctttctac tcttccgtct gcctcctctc catatgatca ccacagagga       1020
ctgaggtggt ttacgaaaga agatgatgcc attggaacct aaacccggga gactcaagaa       1080
gctgtccagc tgaaagttgg atcaagcaga gagctcaaac ggggattcga ttatgatctg       1140
aatttcaggc agaaagagcc aatagtagac cagagctttg gagcattgca gggtctatta       1200
agtctaaacc agacaccaca acataaccaa gaaacaagac agtttgttgt agaaggaaag       1260
caagatgaag cgatgggaag ctctctgaca ctctcaatgg ctggaggagg catggaggaa       1320
acagagggaa caaaccagca tcagtgggtt agccatgaag gtccatcatg gctctattca       1380
acaacaccag gtggaccatt ggctgaagca ctgtgtctcg gtgtctccaa caacccaagt       1440
tctagtacta ctactagtag ctgcagcaga agctcaagct aa                         1482

<210> SEQ ID NO 11
<211> LENGTH: 1290
<212> TYPE: DNA
<213> ORGANISM: Arabidopsis thaliana

<400> SEQUENCE: 11
atgcagagcc ctaaaatgga gcaggaggag gttgaggagg agaggatgag gaataagtgg         60
ccgtggatga aggcggcgca gttaatggag tttcggatgc aagctttggt gtatagatac        120
atagaggctg gtctccgtgt gcctcatcat ctcgtggtgc ctatttggaa cagtcttgct        180
ctctcttctt cctccaatta caactatcac tcttcttctc tgttgagtaa caagggagta        240
acccatatcg acacgttgga aactgaacca actaggtgca ggagaacaga tgggaagaaa        300
tggcgctgta gcaacacggt ccttctattc gagaagtact gtgaacggca catgcataga        360
ggtcgtaaac gttcaagaaa gcttgtggaa tcttcttctg aggttgcttc atcatcaacc        420
aaatacgaca cacactatgg tttggatagg tataacgaga gtcagagtca tcttcatggg        480
acaatctcgg gttctagtaa tgcgcaggta gttaccattg cttcactgcc tagtgccaga        540
tcctgtgaaa atgtcattcg tccgtcttta gtgatctctg aattcacaaa caaaagtgtg        600
agtcacggca gaaagaacat ggagatgagt tatgatgact ttattaatga aaagaggcg         660 agtatgtgtg ttggagttgt tcctcttcaa ggtgatgaga gcaaaccttc ggttcaaaag        720
```

```
ttcttccctg aggtatctga taaatgctta gaagctgcaa aattctcaag caacaggaag    780
aatgatataa ttgcaagaag cagagaatgg aagaatatga atgttaatgg tggttttgttt   840 catggtatcc acttttctcc agacactgtt cttcaagaac gtggttgttt tcgtttacaa    900
ggagttgaaa cagacaatga accaggaagg tgccgaagaa cagatgggaa gaagtggaga    960
tgcagcaaag atgttttgtc tggtcagaag tactgcgata agcacatgca tagaggtatg   1020
aagaagaagc atccagttga tactactaac tcacatgaga atgccgggtt tagcccgtta   1080
accgtggaaa cagctgttag atcggttgtg ccttgcaaag atggagatga ccagaagcat   1140
tctgtttcag tcatgggaat tacactgccc cgagtttctg atgagaagag cactagcagt   1200
tgcagtaccg acactaccat tactgacaca gctttaaggg gtgaagacga cgatgaggag   1260
tacttgtctt tgttttcacc aggtgtttag                                    1290
```

```
<210> SEQ ID NO 12
<211> LENGTH: 140
<212> TYPE: RNA
<213> ORGANISM: Glycine max

<400> SEQUENCE: 12
ucauggcucu cuuuguauuc uuccacagcu uucuugaacu gcauccaaag aguuccuuug     60
caugcaugcc auggcacucu uacucccaaa ucuuguuuug cgguucaaua aagcugucggg   120 aagauacaga uagggucaac                                                140

<210> SEQ ID NO 13
<211> LENGTH: 21
<212> TYPE: RNA
<213> ORGANISM: Glycine max

<400> SEQUENCE: 13
uuccacagcu uucuugaacu g                                               21

<210> SEQ ID NO 14
<211> LENGTH: 126
<212> TYPE: RNA
<213> ORGANISM: Glycine max

<400> SEQUENCE: 14
cucaaguccu ggucaugcuu uuccacagcu uucuugaacu ucuuaugcau cuuauaucuc     60
uccaccucca ggauuuuaag cccuagaagc ucaagaaagc ugugggagaa uauggcaauu    120
caggcu                                                               126

<210> SEQ ID NO 15
<211> LENGTH: 21
<212> TYPE: RNA
<213> ORGANISM: Glycine max

<400> SEQUENCE: 15
uuccacagcu uucuugaacu u                                               21

<210> SEQ ID NO 16
<211> LENGTH: 117
<212> TYPE: RNA
<213> ORGANISM: Glycine max

<400> SEQUENCE: 16
caacaagucc uguuaugcuu uuccacagcu uucuugaacu ucuuaugccu agugcaauua     60 uugaugguggc auagaaguuu aagaaaaaug uggaaaaaca ugucaaaucu aggacuu      117
```

<210> SEQ ID NO 17
<211> LENGTH: 21
<212> TYPE: RNA
<213> ORGANISM: Glycine max

<400> SEQUENCE: 17
uuccacagcu uucuugaacu u                                              21

<210> SEQ ID NO 18
<211> LENGTH: 114
<212> TYPE: RNA
<213> ORGANISM: Glycine max

<400> SEQUENCE: 18
gugaucuucc acagcuuucu ugaacugugu gugaggcuuu cucuccaaug aagguuuaua    60
cccuaugcaa agaaauucu augagcacaa ucaagauag cuggaaaa ucac             114

<210> SEQ ID NO 19
<211> LENGTH: 22
<212> TYPE: RNA
<213> ORGANISM: Glycine max

<400> SEQUENCE: 19
uuccacagcu uucuugaacu gu                                             22

<210> SEQ ID NO 20
<211> LENGTH: 1200
<212> TYPE: DNA
<213> ORGANISM: Glycine max

<400> SEQUENCE: 20
atggacttgc agttgaagca atggagaaac cagcatgagt cagagcaaga acaagaacat    60
tattccccaa acatggcaaa atttctatct caacaacaac acccaccacc atttccctct   120
gcactccctc tctttgtacc tgaacaaccc aacaccaaag tcagcacctt gtcagcattt   180
tctgattcca cattaccctc ttctcccaga tttcccagaa tggagagttg cttcagcttt   240
gcacaatggc aagagcttga gttgcaggct ctgatattca ggtacatgct ggccggtgct   300
cctgttcctc ctgagctcct tctaccaatc aagaaaagct tccttcaact ttatcaccct   360
cctaattgta aatttctaac cccatttttc tacttcctaa ttatttggta ctactggcga   420
agagaagcac tggatccgga gccggggcgg tgccggagga ccgacggcaa gaagtggcgg   480
tgctcgaagg acacggtggc aggtcagaag tactgcgacc gccacatgca ccgtggccgg   540
aaccgttcaa gaaagcctgt ggaacaacgt gaaggatctc tttctgctat agactctgtt   600
tcttcttcac actctgcttc attcaatctc cttcacctcg gtcaaagaga atggcttgga   660
aaaggtttaa ggctcaagtc ctctatttca tcatatcctt tgaggttgtg ctgttccgct   720
gtggccaaga gtgacagcaa gagcttgtct agaaaccgtg atcatgtgga tggggatggc   780
aaatcaaatg ccatgtcttt gaggcatttc tttgatgatt ggccaaggac actgcaagag   840
cctgacaatg tgaaagcaa tggaagccag aacaacaact caggaaaatg tctttctatg   900
tcaacaccag gaatcgatcc ctcggatgtg tcgttgaaat tgaccactgg ctatggagag   960
gacgcgtgcc aggcagcttc ggtgggagga ccacttgcag aggcattgag atcatccacc  1020
accagctcca cttcttcacc aaccataaat aggaaacaaa catttccgga taatgaacaa  1080
gttgagtttg tagttagcaa ttgttggcat ggtcttgttt ctttaaccaa atccatactt  1140

```
tactgccaag cacatgcaca cattacagat agagttctga aaagtcacat gaggaggtga    1200
```

<210> SEQ ID NO 21
<211> LENGTH: 1016
<212> TYPE: DNA
<213> ORGANISM: Glycine max

<400> SEQUENCE: 21

```
actcaactaa actaaactaa agaaaagaat aataaaaagg agaagatggt ttagaattgg      60
tttgagaaga gaagagtggg ggaggagaga tgagtaagtg gcctttcaca atatctcagt     120
ggcaggaact ggaacatcaa gctttaattt acaaatacat ggtggctggt cttcctgtgc     180
ctcctgatct agtcattccc attcagaaca gcttccactc catttcccaa accttcttgc     240
accatccctc taccaccatg agttattgtt ccttctatgg gaagaaggtg gacccggagc     300
caggacgatg caggaggact gatgggaaaa agtggaggtg ctccaaggaa gcctacccag     360
actccaagta ctgtgagcga cacatgcacc gtggccgcaa ccgttcaaga aagcctgtgg     420
aatcacaaac tatgacacag tcatcatcca atgtgtcatc attgactgta actgctggca     480
gcagcaccag tgcaactgga aatttccaga acctttccac cacaaatgca tatggtaatc     540
cccaagggac tgcttctgga acagaccaaa cccactatca catggattcc attccctatg     600
ggatcccaag taaagaatac aggtattttc aaggatctaa atctgaggaa catagtttct     660
tgtccaaaac tttaggaagc aacagggttc tacacatgga gccacagatg gacaacactt     720
tgatgccaac cggtggagtt gcctcattct ctacattgag atcaaataat aattccatgt     780
tgcagggtga ttatctgcag ccttctttct tatctagtga atatgcctcg gcagaaactg     840
tgaagcaaga gggtcagtcc cttcgaccgt tctttgatga atggcctaaa agcagggact     900
catggtctgg tctggaagat gagagatcca atcacactca actctcaata tccattccta     960
tgtcatcgtc aaatttctct gcaactagct ctcattcccc acatggtgag atttaa        1016
```

<210> SEQ ID NO 22
<211> LENGTH: 1242
<212> TYPE: DNA
<213> ORGANISM: Glycine max

<400> SEQUENCE: 22

```
atgaatggaa ggaacgttaa cacaaacagg ttccctttca ctccttccca gtggcaagag      60
cttgaacacc aagctctcat ctacaaatac atggcttcag gtatctccat ccccctgac     120
cttctcttca ccatcaaaag aacaacccac ttggactcct caagactatt gcctcaccac     180
cctcaacact ttggatggaa ctatttgcca atggggttgg ggaggaaaat agaccggag     240
ccagggaggt gtagaagaac agatggaaag aaatggaggt gctcaaagga ggcgtatcca     300
gattcaaagt actgtgagag gcacatgcac agagggaaaa atcgttcaag aaagcctgtg     360
gaagttttga aaacaacacc aacgacagca gcagtggcaa caaacacaga tgcctcaacc     420
ccaacaacaa tcttatcaat caccaaaaac agtcctgcac atgcactctc cccaaccact     480
cattctctct tcatgacaca ttaccatcat catcatcatc ccctcacccc tcagcaacat     540
tcctcccact ccttcctcta tcatcattct tcgaggccct cttccgtatt tattgagaag     600
tttatactaa caagcctgct tggcttgatg aagtatgtgt atggactgaa ggaggaggtg     660
gacgagcatg cctcttcac agaaccttct ggaactatga gaagcttctc tgcttcctca     720
atggaagatt catggcaact cacaccactg actataagct cctcttcctc ttcgaaacag     780
aggaactgct ctggtttatc caatgacaac aacgagtact cctacttgca acttcagagc     840
```

```
ctcaatggca acaactcaaa acagccacaa caagatcaag gttgctacat atcaggcagt      900
gatgtcaagt gcgaaacatt catgaaactt gggaaagaag aacctcagaa aaccgttcat      960
cgcttcttcg atgaatggcc ccctaaaagc agaggatcgt ggcttgattt ggatgataaa     1020
tcatccacca cccagctttc aatttccatt ccaacttcta ctcatgattt tgcaactttc     1080
aattcaacaa cccaacgagt agctagggaa ttgtttatga cttgcatttt ttgttttgc      1140 agatggttga gtttagcttt caacagtggg gtccttcagt ccttgtactt gaatcaaagg     1200
ccaaaaatgt acttacatgg tggggttcac atcatgttgt ga                        1242
```

<210> SEQ ID NO 23
<211> LENGTH: 1266
<212> TYPE: DNA
<213> ORGANISM: Glycine max

<400> SEQUENCE: 23

```
atggacttgc agttgaagca atggagtaac cggcatgagt cagaacaaga acattattcc       60
ccaaacatgc caaaatttct ccctcaacac cacccaccac catctccctc tgcactccct      120
ctctttgtac ctgaacaacc caacaccaaa gtctgcaccc taaacaaaca aaggatggag      180
agttgcttca gctttgcaca gtggcaagag cttgagttgc aggctctgat attcaggtac      240
atgctggccg gtgctcctgt tcctcctgag ctccttctac caatcaagaa aagcttcctt      300
caactttata accctccttg tgaaactcta tttctggttg aaaactgtgt aaaagcagct      360
ataaaactgt atttaagttt tatgctattt atagttgatt tgtctagttt tgagttactc      420
cattttggtg agaaaattgt gatgaaagtt ttgatcttgg gcatgtgttt gaggcatcag      480
tgttggaatc agggtactac tggggaagag cagcgctgga tccggagccg ggcggtgcc       540 ggaggaccga cggcaagaag tggcggtgct cgaaggacgc ggtggcgggt cagaagtact      600
gcgaccgcca catgcatcgt ggccgaaacc gttcaagaaa gcctgtggaa caacgaaacc      660
ctgatcctac ctagctgtta tgtctcatat atacttggaa aagatttaaa aactttattg      720
tgcataaata ggccccaaac tttcttgtta agttgctgtt ttggtgcatt agaatgcatt      780
tcctctgggg ccaagagtga caacaagagc ttctttgaaa accatgatca tgtggatggg      840
gatggaaatt cagccaaatc tgatggccat gtcttgaggc atttctttga tgattggcca      900
aggacactgc aagagcctga caatggtgaa agcaatggtt gccagaacaa caactcagga      960
acatgtcttt ctatgtcaac accaggaatc acttcctcgg atgtgtcgtt gaaattgtcc     1020
actggccatg gagaggatgc gtgccacgcg gcctcaatgg gaggaccact tgcagaggca     1080
ttaagatcat ccaccaccag ctccacttct tcaccaacca gtcaactatt tattgcattg     1140
tctttactat tcatcccaaa gtgggaattg ttatttccac tctcactttc tgccaccaat     1200
acactcccct tgcttggtt ttattcaaaa ataccactga caaatacact tcccatctgt     1260
cactga                                                               1266
```

<210> SEQ ID NO 24
<211> LENGTH: 1396
<212> TYPE: DNA
<213> ORGANISM: Glycine max

<400> SEQUENCE: 24

```
atgaatggaa ggaacaggtt cccctttacc ccatcacagt ggcaagagct tgaacaccaa       60
gctctcatct acaagtacat ggcttcaggc atttccattc cacctgatct tctcttcacc      120
```

```
ataaaaagga gctattttga ttcccctctg tcctcaaggc ttttgcctaa ccagccacag      180
cactttggat ggaactacct tcagatgggt ttgggaagaa aaatagaccc tgagccaggt      240
aggtgtagaa gaactgatgg caagaaatgg agatgctcca agaagcata cccagattca      300 aagtactgtg agaggcacat gcacagaggg aagaatcgtt caagaaagcc tgtggaagtt      360
ttaaaatcaa caacaacacc atcatcatca acaacaaact caaatgcttc ttctacacaa      420
caagcaatct catcaatcac caaaattaat agcactctct cacctcttgc atcatctgag      480
actcaccaac accaccacta tcctcaacac tatggctcct ttctctatca tcatcccct      540 ccttcaaggt cctctggcat tggcttgtct tttgaagaca cagtgctcc cttgtttctt      600 gacactggct catgctctca gtccaacaca gactgcagga gtaggtatgt ttatggagag      660
aaagaggagg tggatgagca tgctttcttc acagaacctt gtggtgttat gaaaagcttc      720
tctgcttcct ctatggatga ctcatggcaa ctcacaccat tgactatgag ctcctcatct      780
tcatcttcca gcagaggag ttcctttggc ttgtccagtg attactcttg cttgcaactt      840
cagagccact caaagcagca gcagcaagag catcatcaag atcaggggtg ctacatgttt      900
ggtgctggtc aagttgtgaa agaagaacct cagaaaacgg ttcatcgctt ctttgatgaa      960
tggccacaca aaggaagaga aggctcttgg cttgatttgg atgacaaatc ttccacaacc     1020
caactttcaa tttccatccc cacatcttct catgattttt caactttcag ttccagaacc     1080
caccatgatg gttgagtgta ggtttccaat aatgggtcct ctgtacggaa atcaaaggcc     1140
aaaaatgtac ctataagggt ggggtttaag atgctttggg gtcttatttc caaccacacc     1200
ctcttctttt ttcttctgcc ataaaggcac ttgaaaggga tttctgtctc catggagaga     1260
tctaatgtgt aatgctatat gatgctaatg ctttcttagt tataagtgct tccttccaaa     1320
catagtataa aaaattctct gtgacaaagc ctgaactgtt taatatttga gctaacattc     1380
aattgcacat ctatgt                                                     1396

<210> SEQ ID NO 25
<211> LENGTH: 1122
<212> TYPE: DNA
<213> ORGANISM: Glycine max

<400> SEQUENCE: 25
atgatgagtg caagtgcagg tgcaagaaat aggtctccgt tcacacaaat tcagtggcaa       60
gagcttgagc aacaagctct tgtttttaag tacatggtta caggaacacc tatcccacca      120
gatctcatct actctattaa aagaagtcta gacacttcaa tttcttcaag gctcttccca      180
catcatccaa ttgggtgggg atgttttgaa atgggatttg gcagaaaagt agacccagag      240
ccagggaggt gcagaagaac agatggcaag aaatggagat gttcaaagga ggcatatcca      300
gactcaaagt actgtgaaag acacatgcac agaggcagaa accgttcaag aaagcctgtg      360
gaagtttctt cagcaacaag caccgccaca aacacctccc aaacaatccc atcatcttat      420
accagaaacc tttccttgac caataacagt aaccccaaca taacaccacc accacccc      480 tcttctttcc ctttctctca tttgccctct tctatgccta ttgatcagtc ccaacccttt      540
tcccaatcct accaaaactc ttctctcaat cccttcttct actccaatc aacctcctct      600 agaccccag atgctgattt tccaccccaa gatgccacca cccaccacct attcatggac      660
tctgctggct cttattctca tgatgaaaag aattataggc atgttcatgg aataagggaa      720
gatgtggatg agagagcttt cttcccagaa gcatcaggat cagctaggag ctatacagac      780
tcgtaccaac aactatcaat gagctcctac aagtcctatt caaactccaa ctttcagaac      840
```

```
attaataatg atgccaccac caacccaaga cagcaagagc agcaactaca acaacaacaa      900
cactgttttg ttttagggac agacttcaaa tcaacaaggc caagcaaaga gaaagaagct      960
gagacaacaa caggtcagag accccttcac cgtttctttg gggagtggcc accaaagaac     1020
acaacaacag attcctggct agatcttgct tccaactcca gaatccaaac cggtgatgat     1080
cctgcttctt cttccctact ctcattatca cacccttttt aa                       1122
```

<210> SEQ ID NO 26
<211> LENGTH: 1298
<212> TYPE: DNA
<213> ORGANISM: Glycine max

<400> SEQUENCE: 26

```
atggacttcc atctgaagga atggagaaac cagcatgagt cagaggaaca acaacattct       60
acaaagatgc caaaacttct ccctgaatcc catcatcaac agccatctgc cactgcactc      120
cctttgtttg tacctgaacc caacagcagc agcaaagtca gcaccctgtc agattcaaca      180
ttagcagctg aaactgaaac aatgaccact acaaccacta acagattatt cccaggatg      240
gggagctact tcagcttgtc tcagtggcag gagcttgagt tgcaggcttt gatattcagg      300
tacatgttgg ctggtgctgc tgttcctcct gaactccttc aaccaatcaa gaaaagcctt      360
cttcattccc ctcactattt cctccatcac cctctccaac attaccaacc tgctgctttg      420
ttgcaatcag ggtattgggg tagaggagcg atggatccgg agccagggcg gtgccggaga      480
accgacggca gaaatggcg tgctcgagg gacgtggtgg ctgggcaaaa gtactgtgag       540
cgccacatgc atcgtggaag aaaccgttca agaaagcctg tggaactacc cacaccaact      600
agtgctaata attgtgatgg tggatctcta ggactaggtg cttcttcatc ttccatttct      660
tcaccacccc tagcttctgc ttcactcaaa tccccatttg atcttcttcg tcttaatgaa      720
cgttcctctg ggaccaagaa tgaagacgaa gaccatgtgg gtggggatgg cagatcaggt      780
ggagggggtg gccatatgct gaggcatttc ttcgatgatt ggccacgatc actgcaagac      840
tctgacaacg ttgaaaacaa tgctgctggc cctagcctct ctatttcaat gcccggaaat      900
gctgctgctg cttcctcgga tgtgtcattg aaattgtcca cgggctatgg agaggaccca      960
ggcccaagaa atgagaatgt gggcctcgtg gcagagcagc tgcagttgaa ttgggccgga     1020
ggatgggcct cgtctaatca agtggcttcc atgggaggac cactggccga ggcactcaga     1080
tcatctattt caacttcatc tcccactagt gttttgcatc acttgcctcg tggttctgga     1140
tctgagacca gcattattag cacctgaact tagtttgtag gtgcccccaa ttaattttct     1200
ctttttttgtt ttgaggttaa gttccacttt tagagcattc ttggacaacg gttatgttca     1260
tatcaaacct ctggactact tttgtttcta agtgggcg                            1298
```

<210> SEQ ID NO 27
<211> LENGTH: 20
<212> TYPE: RNA
<213> ORGANISM: Arabdipsis thaliana
<220> FEATURE:
<221> NAME/KEY: misc_feature
<222> LOCATION: (13)..(13)
<223> OTHER INFORMATION: n is a, c, g, or u

<400> SEQUENCE: 27

```
caaguucuuu cgnacaccuu                                                    20
```

<210> SEQ ID NO 28

```
<211> LENGTH: 21
<212> TYPE: RNA
<213> ORGANISM: Arabisopsis thaliana
<220> FEATURE:
<221> NAME/KEY: misc_feature
<222> LOCATION: (8)..(8)
<223> OTHER INFORMATION: n is a, c, g, or u

<400> SEQUENCE: 28
aagguguncg aaagaacuug c                                        21
```